United States Patent [19]

Ebetino et al.

[11] Patent Number: 5,760,021

[45] Date of Patent: Jun. 2, 1998

[54] PHOSPHONOCARBOXYLATE COMPOUNDS PHARMACEUTICAL COMPOSITIONS, AND METHODS FOR TREATING ABNORMAL CALCIUM AND PHOSPHATE METABOLISM

[75] Inventors: Frank Hallock Ebetino; Allan Vincent Bayless, both of Cincinnati, Ohio; Susan Mary Dansereau, Sherburne, N.Y.

[73] Assignee: The Procter & Gamble Company, Cincinnati, Ohio

[21] Appl. No.: 55,810

[22] Filed: May 7, 1993

Related U.S. Application Data

[63] Continuation-in-part of Ser. No. 891,355, May 29, 1992, abandoned, Ser. No. 891,490, May 29, 1992, abandoned, Ser. No. 891,309, May 29, 1992, abandoned, Ser. No. 52,695, Apr. 30, 1993, Pat. No. 5,391,743, Ser. No. 52,694, Apr. 30, 1993, Pat. No. 5,753,634, and Ser. No. 52,696, Apr. 30, 1993, Pat. No. 5,763,611, which is a continuation-in-part of Ser. No. 890,886, May 29, 1992, abandoned, said Ser. No. 52,695, is a continuation-in-part of Ser. No. 890,885, May 29, 1992, abandoned, said Ser. No. 52,694, is a continuation-in-part of Ser. No. 891,487, May 29, 1992, abandoned.

[51] Int. Cl.$^6$ .................................................. A01N 57/00
[52] U.S. Cl. ............................ 514/80; 562/10; 562/17; 514/75
[58] Field of Search .................. 514/80, 75; 562/10, 562/17

[56] References Cited

U.S. PATENT DOCUMENTS

| | | | |
|---|---|---|---|
| 3,584,124 | 6/1971 | Francis | 424/204 |
| 3,657,282 | 4/1972 | Christensen et al. | 260/348 A |
| 3,683,080 | 8/1972 | Francis | 424/204 |
| 3,962,433 | 6/1976 | Worms et al. | 424/212 |
| 4,086,334 | 4/1978 | Schmidt-Dunker et al. | 424/177 |
| 4,133,872 | 1/1979 | Schmidt-Dunker et al. | 424/1 |
| 4,340,599 | 7/1982 | Lieb et al. | 424/212 |
| 4,806,532 | 2/1989 | Dousa | 514/120 |
| 4,959,360 | 9/1990 | Lafferty et al. | 514/217 |
| 4,960,684 | 10/1990 | Ishikawa et al. | 430/467 |
| 5,013,850 | 5/1991 | Lee | 549/222 |
| 5,034,552 | 7/1991 | Keppler et al. | 556/137 |
| 5,182,388 | 1/1993 | Cipolli et al. | 544/195 |
| 5,190,822 | 3/1993 | Nishikawa et al. | 428/402.2 |

FOREIGN PATENT DOCUMENTS

| | | |
|---|---|---|
| 65960/80 | 6/1981 | Australia ............ A61K 31/675 |
| 0 186 405 | 7/1986 | European Pat. Off. |
| 0 283 191 | 9/1988 | European Pat. Off. |
| 290987 A | 11/1988 | European Pat. Off. |
| 0 298 553 | 1/1989 | European Pat. Off. |
| 0 367 714 | 5/1990 | European Pat. Off. |
| 389 338 A1 | 9/1990 | European Pat. Off. |
| 0 477 454 A1 | 4/1992 | European Pat. Off. |
| 0 508 687 A1 | 10/1992 | European Pat. Off. |
| 2310-450 | 9/1974 | Germany. |
| 259 154 | 8/1988 | Germany. |
| 38 04 686 A1 | 8/1989 | Germany. |
| 284155 A | 11/1990 | Germany. |
| 2 019 499 | 6/1991 | Spain. |
| WO 88/09171 | 12/1988 | WIPO. |
| WO 93/121222 | 6/1993 | WIPO. |

OTHER PUBLICATIONS

Schwarz, A. and G. Kloss, "Beziehungen Zwischen chemischer Struktur und Skelettfixierung verschiedener Tc–99m–Phosphonsäuren", Radiochemisches Labor, Hoechst A–G, Frankfurt (M) 80, BR Deutschland, pp. 120–124 (no month identified, 1981).
CA: 102 12372 1984.
CA 96: 48329 1981.
CA 87: 73378 1987.

*Primary Examiner*—Paul J. Killos
*Attorney, Agent, or Firm*—Richard A. Hake; David L. Suter; Carl J. Roof

[57] ABSTRACT

The present invention relates to compositions comprising pharmaceutically-acceptable carriers and a phosphonocarboxylate, or a pharmaceutically-acceptable salt thereof, having a structure according to formula (I):

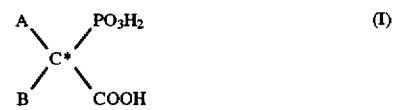

42 Claims, No Drawings

PHOSPHONOCARBOXYLATE COMPOUNDS PHARMACEUTICAL COMPOSITIONS, AND METHODS FOR TREATING ABNORMAL CALCIUM AND PHOSPHATE METABOLISM

This is a continuation-in-part of the following: U.S. patent application Ser. No. 08/052,695, filed Apr. 30, 1993, U.S. Pat. No. 5,391,743, which is a continuation-in-part of U.S. patent application Ser. No. 07/890,885, filed May 29, 1992 (now abandoned); U.S. patent application Ser. No. 08/052,694, filed Apr. 30, 1993, U.S. Pat. No. 5,753,634, which is a continuation-in-part of U.S. patent application Ser. No. 07/891,487, filed May 29, 1992 (now abandoned); U.S. patent application Ser. No. 08/052,696, filed Apr. 30, 1993, U.S. Pat. No. 5,763,611, which is a continuation-in-part of U.S. patent application Ser. No. 07/890,886, filed May 29, 1992 (now abandoned); U.S. patent application Ser. No. 07/891,355, filed May 29, 1992; abandoned, U.S. patent application Ser. No. 07/891,490, filed May 29, 1992; abandoned and U.S. patent application Ser. No. 07/891,309, filed May 29, 1992, abandoned.

BACKGROUND OF THE INVENTION

This invention relates to novel phosphonocarboxylate compounds. This invention further relates to pharmaceutical compositions containing phosphonocarboxylate compounds, as well as to methods for treating or preventing metabolic bone disorders characterized by abnormal calcium and phosphate metabolism by utilizing a compound or pharmaceutical composition of the present invention. Specifically, this invention relates to methods for treating or preventing osteoporosis, or arthritis, especially rheumatoid arthritis and osteoarthritis, by utilizing a compound or pharmaceutical composition of the present invention.

A number of pathological conditions which can afflict humans and warm blooded animals involve abnormal calcium and phosphate metabolism. Such conditions may be divided into two broad categories:

(1) Conditions which are characterized by anomalous mobilization of calcium and phosphate leading to general or specific bone loss, such as osteoporosis and Paget's disease, or excessively high calcium and phosphate levels in the fluids of the body, such as hypercalcemia of tumor origin. Such conditions are sometimes referred to herein as pathological hard tissue demineralizations.

(2) Conditions which cause or result from deposition of calcium and phosphate anomalously in the body, such as arthritis, including rheumatoid arthritis and osteoarthritis. These conditions are sometimes referred to herein as pathological calcifications.

The first category includes the most common metabolic bone disorder, osteoporosis; osteoporosis is a condition in which bone hard tissue is lost disproportionately to the development of new hard tissue. Osteoporosis can be generally defined as the reduction in the quantity of bone, or the atrophy of skeletal tissue. Marrow and bone spaces become larger, fibrous binding decreases, and compact bone becomes fragile. Osteoporosis can be subclassified as menopausal, senile, drug-induced (e.g. adrenocorticoid, as can occur in steroid therapy); disease-induced (arthritic and tumor), etc.; however, the manifestations are essentially the same.

In general, there are two types of osteoporosis: primary and secondary. "Secondary osteoporosis" is the result of a separate disease process or agent. However, approximately 90% of all osteoporosis cases are "primary osteoporosis". Such primary osteoporosis includes postmenopausal osteoporosis, disuse osteoporosis, age-associated osteoporosis (affecting a majority of individuals over the age of 70 to 80), and idiopathic osteoporosis affecting middle-aged and younger men and women.

For some osteoporotic individuals, the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone.

This remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by an osteoblast.

Normally, in adults, the remodeling cycle results in a small deficit in bone, due to incomplete filling of the resorption cavity. Thus, even in healthy adults, age-related bone loss occurs. However, in osteoporotics, there may be an increase in the number of BMLJs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Current osteoporosis treatment consists primarily of calcium and estrogen administration.

In addition to osteoporosis, bone loss can result from arthritis, including rheumatoid arthritis and osteoarthritis. Rheumatoid arthritis is a chronic, systemic and articular inflammatory disorder characterized by weakening of the joint capsules and ligaments, followed by destruction of cartilage, ligaments, tendon and bone, and a decrease in viscosity and other alterations in the synovial fluid. Rheumatoid arthritis symptoms include systemic weakness, fatigue, localized pain, stiffness and weakness and swelling and deformation of the joints of the body. Rheumatoid arthritis is most common in women in the fourth to sixth decade of life.

Osteoarthritis is an inherently non-inflammatory disorder of the movable joints characterized by deterioration and abrasion of articular cartilage, as well as by formation of new bone at the joint surface. As osteoarthritis progresses, the surface of the articular cartilage is disrupted and wear particles gain access to the synovial fluid which in turn stimulates phagocytosis by macrophage cells. Thus, an inflammatory response is eventually induced in osteoarthritis. Common clinical symptoms of osteoarthritis include cartilaginous and bony enlargements of the finger joints and stiffness on awakening and painful movement.

A variety of polyphosphonic acid derivatives have been proposed for use in the treatment and prophylaxis of diseases involving abnormal calcium and phosphate metabolism. For example, numerous references all incorporated by reference herein, disclose compositions containing polyphosphonates, in particular bisphosphonates, such as ethane-1-hydroxy-1,1-diphosphonic acid ("EHDP"), and their use in inhibiting anomalous deposition and mobilization of calcium and phosphate in animal tissue: U.S. Pat. Nos., 3,683,080, issued Aug. 8, 1972 and U.S. Pat. No. 4,230,700, issued Oct. 28, 1980, both to Francis, and U.S. Pat. No. 4,868,164 to Ebetino, issued Sep. 19, 1989. Numerous other references describe substituted phosphonic acids useful for the treatment of osteoporosis and/or arthritis, and are hereby incorporated by reference herein: U.S. Pat. Nos. 5,071,840 to Ebetino, et al, issued Dec. 10, 1991, U.S. Pat. No. 4,868,164, to Ebetino, et al., issued Sep. 19, 1989; U.S. Pat. No. 5,104,863, to Benedict, et al., issued Apr. 14, 1992; U.S. Pat. No. 4,267,108, to Blum et al., issued May 12, 1981; U.S. Patent to Breliere, et al., issued May 24, 1988; U.S. Pat. No. 4,876,247 to Barbier, et al., issued Oct. 24, 1989; European Patent Application Publication No. 100,718, of Breliere S.A., published Feb. 15, 1984; European Patent Application Publication No. 170,228, of Boehringer Mannheim GmbH, published Feb. 5, 1986; European Patent Application Publication No. 186,405, of Benedict and Perkins, published Jul. 2, 1986; European Patent Application Publication No. 298,553, of Ebetino, published Jan. 11, 1989; U.S. Pat. No. 4,754,993, to Bosies, et al., issued Nov. 15, 1988; U.S. Pat. No. 4,939,130 to Jaeggi, et al., issued Jul. 3, 1990; U.S. Pat. No. 4,971,958 to Bosies, et al., issued Nov. 20, 1990; WO 90/12017 to Dunn, et al., published Oct. 18, 1990; WO 91/10646 to Youssefyeh, R., et al., published Jul. 25, 1991; AU-A-26738/88 to Jaeggi, K. A., publication date Jun. 15, 1989; AU-A45467/89 of Ciba-Geigy, publication date May 31, 1990.

A limited number of phosphonocarboxylate containing moieties are described in the literature. However, none of these references disclose nor suggest the utility of phosphonocarboxylate compounds of the present invention, useful in preventing and treating bone metabolism.

It has been surprisingly discovered that the compounds of the present invention, having a phosphonocarboxylate moiety, may have potent bone antiresorptive activity and therapeutic utility in treating osteoporosis and arthritis. Moreover, these compounds have reduced bone affinity compared with bisphosphonates. This reduced bone affinity may decrease side effects generally associated with the high bone affinity bisphosphonates. Such side effects include inhibition of bone formation and inhibition of bone remodeling activation frequency.

Certain compounds of the present invention contain a quaternary nitrogen moiety. These compounds exhibit unusual solubility properties. Thus, the quaternary nitrogen-containing phosphonocarboxylate compounds of the present invention may be more readily orally absorbed. Increased oral absorbtion allows for improved therapeutic effect at lower doses. Lower doses are generally preferable because undesirable side effects are decreased.

It is therefore an object of the present invention to provide a new potent class of compounds which are potent bone resorption inhibiting agents useful in osteoporosis therapy and anti-arthritic agents useful in the treatment of arthritis, especially osteoarthritis and rheumatoid arthritis. It is a further object of the present invention to provide pharmaceutical compositions useful for the treatment and prophylaxis of abnormal calcium and phosphate metabolism. In addition, it is an object of the present invention to provide methods for treating or preventing diseases characterized by abnormal calcium and phosphate metabolism in humans or other mammals.

These and other objects of the present invention will become apparent from the detailed disclosure of the present invention provided hereinafter.

SUMMARY OF THE INVENTION

The present invention relates to pharmaceutical compositions comprising a safe and effective amount of a phosphonocarboxylate, or a pharmaceutically-acceptable salt thereof, having a structure according to formula (I):

wherein
(A)
(1) A is selected from the group consisting of hydrogen; halogen; $SR^1$; $R^2SR^1$; amino; hydroxy; and substituted or unsubstituted $C_1$–$C_8$ alkyl;
(2) B is
  (a) $NH_2$;
  (b) a saturated or unsaturated $C_1$–$C_{15}$ alkyl chain substituted with one or more substituents selected from the group consisting of —$R^3N(R^4)_2$; $R^3[$—$N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$;
  (c) a substituted or unsubstituted, saturated or unsaturated heteroalkyl chain having from 2 to 15 chain atoms, where one or more of said chain atoms is nitrogen;
  (d) a substituted or unsubstituted, saturated or unsaturated heteroalkyl chain having from 2 to 15 chain atoms, where one or more of said chain atoms is selected from S and O; and where said heteroalkyl chain is substituted with one or more substituents selected from the group consisting of —$R^3N(R^4)_2$; —$R^3[$—$N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$; or
  (e) $R^6$—L— where
    (i) L is selected from the group consisting of nil; N; —$N(R^5)_3^+$; S; O; a substituted or unsubstituted, saturated or unsaturated $C_1$–$C_{15}$ alkyl chain; and a substituted or unsubstituted, saturated or unsaturated heteroalkyl chain having from 2 to 15 chain atoms, where one or more of said chain atoms is N, S, or O; and
    (ii) $R^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein $R^6$ may be substituted with one or more substituents independently selected from the group consisting of hydrogen; -$R^3SR^1$; substituted or unsubstituted $C_1$–$C_8$ alkyl; —$R^3OR^4$; —$R^3CO_2R^4$; —$R^3O_2CR^4$; —$R^3N(R^4)_2$; $R^3[$—$N(R^5)_3]^+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; substituted or unsubstituted aryl; and hydroxy; and
(3)
  (a) $R^1$ is independently selected from the group consisting of hydrogen; —$C(O)R^7$; —$C(S)R^7$; —$C(O)N(R^7)_2$; —$C(O)OR^7$; —$C(S)N(R^7)_2$; and —$C(S)OR^7$; where $R^7$ is hydrogen or substituted or unsubstituted $C_1$–$C_8$ alkyl;
  (b) $R^2$ is substituted or unsubstituted $C_1$–$C_8$ alkyl;
  (c) $R^3$ is selected from the group consisting of nil and substituted or unsubstituted $C_1$–$C_8$ alkyl;

(d) R⁴ is independently selected from the group consisting of hydrogen; substituted or unsubstituted $C_1$–$C_8$ alkyl; and —$R^2SR^1$; and (e) R⁵ is independently selected from the group consisting of substituted or unsubstituted $C_1$–$C_{15}$ alkyl; substituted or unsubstituted phenyl; benzyl; and -$R^2SR^1$;

or (B) A and B are covalently linked together with C* to form a monocyclic or bicyclic ring having the following structure:

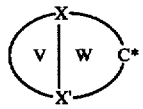

where (1) W is a substituted or unsubstituted, saturated or unsaturated carbocyclic ring comprising C*, X, and X', said carbocyclic ring having a total of from 3 to 6 ring carbon atoms; or a substituted or unsubstituted, saturated or unsaturated heterocyclic ring comprising C*, X and X', said heterocyclic ring having a total of from 4 to 6 ring atoms, where one or more of said ring atoms is N, O, or S;

(2) V is nil; a substituted or unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and (3) X and X' are independently N or C;

except that if neither V nor W is a nitrogen containing heterocycle, then at least one of V or W is substituted with one or more substituents selected from the group consisting of —$R^3N(R^4)_2$; —$R^3[—N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$.

The present invention further relates to phosphonocarboxylate compounds and the pharmaceutically-acceptable salts thereof. The novel compounds of the present invention are further defined according to formula (I) as having A selected from hydrogen, halogen, $SR^1$, $R^2SR^1$, amino, hydroxy, or substituted or unsubstituted $C_1$–$C_8$ alkyl when B is a pyridyl containing moiety, a quaternary nitrogen containing moiety, or a sulfur containing moiety. When B is other than a pyridyl containing moiety, a quaternary nitrogen containing moiety, or a sulfur containing moiety, A is selected from halogen, $SR^1$, $R^2SR^1$, amino, or hydroxy.

Finally, the present invention relates to methods for treating or preventing pathological conditions characterized by abnormal calcium and phosphate metabolism in humans or other mammals. These methods comprise administering to a human or other mammal in need of such treatment a safe and effective amount of a compound or a composition of the present invention.

DETAILED DESCRIPTION OF THE INVENTION

Pharmaceutical Compositions Comprising a Phosphonocarboxylate Compound

The compositions of the present invention comprise a phosphonocarboxylate, or the pharmaceutically-acceptable salt thereof. The methods of the present invention comprise administering a phosphonocarboxylate, or a composition containing a phosphonocarboxylate. The compounds useful in the compositions and methods of the present invention have a structure according to formula (1):

wherein (A)

(1) A is selected from the group consisting of hydrogen; halogen; $SR^1$; $R^2SR^1$; amino; hydroxy; and substituted or unsubstituted $C_1$–$C_8$ alkyl;

(2) B is (a) $NH_2$;

(b) a saturated or unsaturated $C_1$–$C_{15}$ alkyl chain substituted with one or more substituents selected from the group consisting of —$R^3N(R^4)_2$; $R^3[—N(^5)_3]^+$; —$R^3N(R^4)C(O)R^4$; —$R^3N(R^4)C(S)R^4$; —$R^3N(R^4)C(N)R^4$; and —$R^3C(O)N(R^4)_2$;

(c) a substituted or unsubstituted, saturated or unsaturated heteroalkyl chain having from 2 to 15 chain atoms, where one or more of said chain atoms is nitrogen;

(d) a substituted or unsubstituted, saturated or unsaturated heteroalkyl chain having from 2 to 15 chain atoms, where one or more of said chain atoms is selected from S and O; and where said heteroalkyl chain is substituted with one or more substituents selected from the group consisting of —$R^3N(R^4)_2$; —$R^3[—N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$; or (e) $R^6$—L— where (i) L is selected from the group consisting of nil; N; —$N(R^5)_3^+$; S; O; a substituted or unsubstituted, saturated or unsaturated $C_1$–$C_{15}$ alkyl chain; and a substituted or unsubstituted, saturated or unsaturated heteroalkyl chain having from 2 to 15 chain atoms, where one or more of said chain atoms is N, S, or O; and (ii) $R^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein $R^6$ may be substituted with one or more substituents independently selected from the group consisting of hydrogen; —$R^3SR^1$; substituted or unsubstituted $C_1$–$C_8$ alkyl; —$R^3OR^4$; —$R^3CO_2R^4$; —$R^3O_2CR^4$; —$R^3N(R^4)_2$; —$R^3[—N(R^5)_3]^+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; substituted or unsubstituted aryl; and hydroxy; and (3)

(a) R¹ is independently selected from the group consisting of hydrogen; —$C(O)R^7$; —$C(S)R^7$; —$C(O)N(R^7)_2$; —$C(O)OR^7$; —$C(S)N(R^7)_2$; and —$C(S)OR^7$; where $R^7$ is hydrogen or substituted or unsubstituted $C_1$–$C_8$ alkyl;

(b) R² is substituted or unsubstituted $C_1$–$C_8$ alkyl;

(c) R³ is selected from the group consisting of nil and substituted or unsubstituted $C_1$–$C_8$ alkyl;

(d) R⁴ is independently selected from the group consisting of hydrogen; substituted or unsubstituted $C_1$–$C_8$ alkyl; and —$R^2SR^1$; and (e) $R^5$ is independently selected from the group consisting of substituted or unsubstituted $C_1$-$C_{15}$ alkyl; substituted or unsubstituted phenyl; benzyl; and —$R^2SR^1$;

or (B) A and B are covalently linked together with C* to form a monocyclic or bicyclic ring having the following structure:

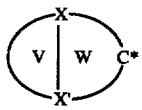

where (1) W is a substituted or unsubstituted, saturated or unsaturated carbocyclic ring comprising C*, X, and X', said carbocyclic ring having a total of from 3 to 6 ring carbon atoms; or a substituted or unsubstituted, saturated or unsaturated heterocyclic ring comprising C*, X, and X', said heterocyclic ring having a total of from 4 to 6 ring atoms, where one or more of said ring atoms is N, O, or S;

(2) V is nil; a substituted o r unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and (3) X and X' are independently N or C;

except that if neither V nor W is other than a nitrogen containing heterocycle, then at least one of V or W is substituted with one or more substituents selected from the group consisting of —$R^3N(R^4)_2$; $R^3[N(R^5)_3]^+$; —$R^3N(R^4)C(O)R^4$; $R^3N(R^4)C(S)R^4$; —$R^3N(R^4)C(N)R^4$; and —$R^3C(O)N(R^4)_2$.

Definitions and Usage of Terms

The following is a list of definitions for terms used herein.

"Heteroatom" is a nitrogen, sulfur, or oxygen atom. Groups containing one or more heteroatoms may contain different heteroatoms. "Alkyl" is an unsubstituted or substituted, straight-chain or branched, saturated or unsaturated hydrocarbon c hain, s ai d hydrocarbon chain may be saturated, having 1 to 15 carbon atoms, and preferably, unless otherwise stated, from 1 to 4 carbon atoms; said hydrocarbon chain may be unsaturated, having 2 to 8 carbon atoms, and preferably, unless otherwise stated, 2 to 4 carbon atoms. Accordingly, the term "alkyl", a s used herein, encompasses alkenyl hydrocarbon unsaturated chains having at least one olefinic double bond and alkynyl hydrocarbon unsaturated chains having at least one triple bond. Preferred alkyl groups include, but are not limited to, methyl, ethyl, propyl, isopropyl, and butyl.

"Heteroalkyl" is an unsubstituted or substituted, saturated or unsaturated, straight-chain or branched heteroalkyl chain, said chain having from 2 to 15, preferably 2 to 8 members, and comprising at least one carbon atom and at least one heteroatom. The term "heteroalkyl", as used herein, encompasses alkenyl heteroalkyl unsaturated chains having at least one olefinic double bond and alkynyl heteroalkyl unsaturated chains having at least one triple bond. "Carbocyclic ring" or "Carbocycle" as used herein is an unsubstituted or substituted, saturated, unsaturated or aromatic, hydrocarbon ring. Carbocycles may be monocyclic or polycyclic: Monocyclic rings generally contain from 3 to 8 atoms, preferably 5 to 7 (or 8) atoms. Polycyclic rings containing two rings contain 6–16, preferably 10 to 12, atoms and those with three rings generally contain 13 to 17, preferably 14 to 15, atoms. "Heterocyclic ring" or "Heterocycle" as used herein is an unsubstituted or substituted, saturated, unsaturated or aromatic ring comprised of carbon atoms and one or more heteroatoms in the ring. Heterocyclic rings may be monocyclic or polycyclic. Monocyclic rings generally contain from 3 to 8 atoms, preferably 5 to 7 atoms. Polycyclic ring systems consisting of two rings generally contain 6 to 16, preferably from 10 to 12 atoms. Polycyclic ring systems consisting of three rings generally contain 13 to 17 atoms, preferably 14 to 15 atoms. Unless otherwise stated the heteroatoms may be independently chosen from nitrogen, sulfur, and oxygen. Unsaturated, non-aromatic heterocycles include, but are not limited to, substituted or unsubstituted thiophene, substituted or unsubstituted oxathiazole, substituted or unsubstituted pyranes, and substituted or unsubstituted furans.

"Aryl" is an aromatic carbocyclic ring. Preferred aryl groups include, but are not limited to, phenyl, tolyl, xylyl, cumenyl, and naphthyl.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" is an oxygen atom having a hydrocarbon chain substituent, where the hydrocarbon chain is an alkyl or alkenyl (e.g., —O-alkyl or —O-alkenyl). Preferred alkoxy groups include, but are not limited to, methoxy, ethoxy, propoxy, and alkyloxy.

"Hydroxyalkyl" is a substituted hydrocarbon chain which has a hydroxy substituent (e.g., —OH), and may have other substituents. Preferred hydroxyalkyl groups include, but are not limited to, hydroxyethyl and hydroxypropyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Aminoalkyl" is a hydrocarbon chain (e.g. alkyl) substituted with an amine moiety (e.g., NH-alkyl—), such as aminomethyl alkyl.

"Alkylamino" is an amino moiety having one or two alkyl substituents (e.g., —N-alkyl), such as dimethylamino.

"Alkenylamino" is an amino moiety having one or two alkenyl substituents (e.g., —N-alkenyl).

"Alkynylamino" is an amino moiety having one or two alkynyl substituents (e.g., —N-alkynyl).

"Alkylimino" is an imino moiety having one or two alkyl substituents (e.g., —N-alkyl—).

"Arylalkyl" is an alkyl moiety substituted with an aryl group. Preferred arylalkyl groups include benzyl and phenylethyl.

"Arylamino" is an amine moiety substituted with an aryl group (e.g., —NH-aryl).

"Aryloxy" is an oxygen atom having an aryl substituent (e.g., —O-aryl).

"Acyl" or "carbonyl" is a carbon to oxygen double bond, e.g. R—C(=O). Preferred acyl groups include, but are not limited to, acetyl, propionyl, is butanoyl and benzoyl.

"Acyloxy" is an oxygen atom having an acyl substituent (e.g., —O-acyl); for example, —O—C(=O)-alkyl.

"Acylamino" is an amino moiety having an acyl substituent (e.g., —N-acyl); for example, —NH—(C═O)-alkyl.

"Halo", "halogen", or "halide" is a chloro, bromo, fluoro, or iodo atom radical. Chloro, bromo, and fluoro are preferred halides.

Also, as referred to herein, a "lower" hydrocarbon moiety (e.g., "lower" alkyl) is a hydrocarbon chain comprised of from, unless otherwise stated, 1 to 6, preferably from 1 to 4, carbon atoms.

As used herein the term "thio-substituent" ($SR^1$ or $R^2SR^1$) includes thiols [—SH] where $R^1$=H; thioesters [—SC(O)$R^7$] where $R^1$=C(O)$R^7$; dithioesters [—SC(S)$R^7$] where $R^1$=C(S)$R^7$; thiocarbamates [—SC(O)N($R^7$)$_2$] where $R^1$=C(O)N($R^7$)$_2$; dithiocarbamates [—SC(S)N($R^7$)$_2$] where $R^1$=C(S)N($R^7$)$_2$; thiocarbonates [—SC(O)O$R^7$] where $R^1$=C(O)O$R^7$; and dithiocarbonates [—SC(S)O$R^7$] where $R^1$=C(S)O$R^7$. $R^7$ is a hydrogen or $C_1$–$C_8$ alkyl. Any of the $SR^1$ substituents may themselves be substituted with an $R^2$ moiety, where $R^2$ is a substituted or unsubstituted $C_1$–$C_8$ alkyl.

Accordingly, additional thio-substituents denoted by $R^2SR^1$ are alkylthiols, alkylthioesters, alkyldithioesters, alkylthiocarbamates, alkyldithiocarbamates, alkylthiocarbonates and alkyl dithiocarbonates.

The term "phosphonocarboxylate", as used herein, relates to compounds that have a phosphonate group ($PO_3H_2$) and a carboxyl group ($CO_2H$) attached to the same carbon atom.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Preferred anionic salts include the halides (such as chloride), acetate and phosphate salts.

A "biohydrolyzable ester" is an ester of the phosphonocarboxylate compounds that does not interfere with the therapeutic activity of the compounds, or that is readily metabolized by a human or other mammal. Many such esters are known in the art, as described in World Patent Publication 87/05297, Johnston et al., published Sep. 11, 1987, and hereby incorporated by reference herein. Such esters include lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters).

As defined above and as used herein, substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, thioxo (—C(═S)—); amino, aminoalkyl (e.g. aminomethyl, etc.), cyano, quaternary amino, quaternary aminoalkyl, amidino, amidinoalkyl, halo, carboxy, alkoxyacetyl (e.g. carboethoxy, etc.), thio, thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, alkynyl and combinations thereof. Particularly preferred substituents include, but are not limited to, amino, aminoalkyl, quaternary amino, amidino, quaternary aminoalkyl, and amidinoalkyl.

Also, as used in defining the structure of the compounds of this invention, a particular radical may be defined for use as a substitutent in multiple locations. As used herein, such a radical is independently selected each time it is used.

With the compositions comprising a compound of formula (I), when A is a sulfur containing moiety, the preferred moity is $SR^1$, where $R^1$ is preferably hydrogen, or acyl. Particularly preferred is where $R^1$ is hydrogen. Preferred A moieties are amino and hydroxy. Particularly preferred is where A is hydroxy. As indicated, other than the further definition of A, preferred embodiments of the compounds useful in the compositions and methods of the present invention are also preferred embodiments of the novel compounds of the present invention.

When B is saturated or unsaturated $C_1$–$C_{15}$ alkyl, the alkyl chain must be substituted with one or more substituents selected from the group consisting of —$R^3N(R^4)_2$; —$R^3$[—N($R^5$)$_3$]$^+$; —$R^3N(R^4)C(O)R^4$; —$R^3N(R^4)C(S)R^4$; —$R^3N(R^4)C(N)R^4$; and —$R^3C(O)N(R^4)_2$. Preferably the required substituent is selected from —$R^3N(R^4)_2$; —$R^3$[—N($R^5$)$_3$]$^+$; —$R^3N(R^4)C(O)R^4$; —$R^3N(R^4)C(S)R^4$; and —$R^3N(R^4)C(N)R^4$. Most preferred is where the required substituent is selected from —$R^3N(R^4)_2$; —$R^3$[—N($R^5$)$_3$]$^+$; and —$R^3N(R^4)C(O)R^4$. The alkyl chain may also be substituted with one or more substituents selected from the group consisting of nil; —$R^3SR^1$; hydrogen; substituted or unsubstituted $C_1$–$C_8$ alkyl; —$R^3OR^4$; —$R^3CO_2R^4$; —$R^3O_2CR^4$; halogen; —$R^3C(O)R^4$; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings. Preferred are $C_1$–$C_8$ alkyl chains.

When B is saturated or unsaturated heteroalkyl having from 2 to 15 atoms, where one of said atoms is a nitrogen, the heteroalkyl chain may be substituted with one or more substituents selected from the group consisting of —$R^3SR^1$; hydrogen; substituted or unsubstituted $C_1$–$C_8$ alkyl; —$R^3OR^4$; —$R^3CO_2R^4$; —$R^3O_2CR^4$; —$R^3N(R^4)_2$; —$R^3$[N($R^5$)$_3$]$^+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings. Preferred nitrogen-containing heteroalkyl chains have from 2 to 8 chain atoms.

When B is saturated or unsaturated heteroalkyl having from 2 to 15 atoms, where one of said atoms is a sulfur or oxygen, and where a no nitrogen atom is in the heteroalkyl chain, then the heteroalkyl chain must be substituted with one or more substituents selected from the group consisting of —$R^3N(R^4)_2$; —$R^3$[—N($R^5$)$_3$]$^+$; —$R^3N(R^4)C(O)R^4$; —$R^3N(R^4)C(S)R^4$; —$R^3N(R^4)C(N)R^4$; and —$R^3C(O)N(R^4)_2$. The required substituent is preferably one of —$R^3N(R^4)_2$; —$R^3$[—N($R^5$)$_3$]$^+$; —$R^3N(R^4)C(O)R^4$; —$R^3N(R^4)C(S)R^4$; or —$R^3N(R^4)C(N)R^4$. Most preferred is where the required substituent is —R³N(R⁴)₂; —R³[—N(R⁵)₃]⁺; or —R³N(R⁴)C(O)R⁴. The heteroalkyl chain may also be substituted with one or more substituents selected from the group consisting of nil; —R³SR¹; hydrogen; substituted or unsubstituted C₁-C₈ alkyl; —R³OR⁴; —R³CO₂R⁴; —R³O₂CR⁴; halogen; —R³C(O)R⁴; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings. Preferred non-nitrogen containing heteroalkyl chains have from 2 to 8 chain atoms.

When B is R⁶—L—, the L moiety may be substituted with one or more substituents selected from the group consisting of —R³SR¹; hydrogen; substituted or unsubstituted C₁-C₈ alkyl; —R³OR⁴; —R³CO₂R⁴; —R³O₂CR⁴; —R³N(R⁴)₂; —R³[N(R⁵)₃]⁺; —R³N(R⁴)C(O)R⁴; —R³N(R⁴)C(S)R⁴; —R³N(R⁴)C(N)R⁴; —R³C(O)N(R⁴)₂; halogen; —R³C(O)R⁴; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings. The L moiety is preferably a nitrogen atom (including quaternary nitrogen), a nitrogen containing heteroalkyl, or alkyl. Where L is a heteroalkyl chain or an alkyl chain, the chain preferably has 2 to 3 chain atoms. A preferred substituent on the L moiety is hydrogen.

The R⁶ moiety may be a saturated or unsaturated, monocyclic or polycyclic carbocycle or heterocycle. Where R⁶ is a monocyclic carbocycle, it is preferably cycloheptyl and cyclohexyl. When R⁶ is a monocyclic heterocycle, preferred are six-membered nitrogen containings rings including pyridine, pyrimidine, piperidine. Also preferred are those six-membered heterocycles having a quaternary nitrogen ring atom, including pyridinium, pyrimidinium, piperidinium pyrazolium. Preferred monocyclic heterocycles also include five-membered nitrogen containing heterocycles, including imidazol, pyrrole, and pyrrolidine. Also preferred are five-membered heterocycles having a quaternary nitrogen ring atom, including imidazolium, pyrrolium, and pyrrolidinium. Where R⁶ is a polycycle, preferred are polycyclic heterocycles having a six-membered ring fused to another six-membered ring and those having a six-membered ring fused to a five-membered ring. Preferred polycyclic heterocycles include those having a quaternary ring nitrogen atom. Particularly preferred R⁶ moieties include cycloheptyl or cyclohexyl.

When B is R⁶—L, preferred compounds are those where one or both of R⁶ and L is a nitrogen-containing moiety.

The R³ moiety is preferably nil.

The R⁴ moiety is preferably hydrogen.

The R⁵ moiety comprises a nitrogen atom bound to three carbon-containing moieties. The R⁵ moiety is substituted on a carbon atom of another moiety, thus providing a quaternary nitrogen group. As indicated in the general structure, the quaternary nitrogen moiety may be a substituent on any of the chain or cyclic moieties described above.

B is preferably a heteroalkyl chain having at least one nitrogen chain atom, or R⁶—L—. Particularly preferred B moieties are R⁶—L—.

According to formula (I), A and B may, together with C*, X and X', form a cyclic structure. Preferred cyclic structures are those where V is a heterocyle having at least one ring nitrogen atom. This ring nitrogen atom may be a secondary, tertiary or quaternary amine. Where neither V nor W are nitrogen-containing heterocycles, then at least one of V or W must be substituted with one or more moieties selected from the group consisting of —R³N(R⁴)₂; R³[—N(R⁵)₃]⁺; —R³N(R⁴)C(O)R⁴; —R³N(R⁴)C(S)R⁴; —R³N(R⁴)C(N)R⁴; and —R³C(O)N(R⁴)₂. In addition to the above requirement, each of V and W may be substituted with one or more substituents selected from the group consisting of —R³SR¹; hydrogen; substituted or unsubstituted C₁-C₈ alkyl; —R³OR⁴; —R³CO₂R⁴; —R³O₂CR⁴; halogen; —R³C(O)R⁴; hydroxy; substituted or unsubstituted arylalkyl; nitro; and unsubstituted or substituted aryl.

Preferred compounds useful in the compositions and methods of the present invention are phosphonocarboxylates, and the pharmaceutically-acceptable salts thereof, having a general structure according to formula (II):

(II)

wherein
(A)
(1) A is hydroxy; and
(2) B is

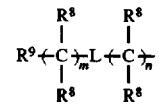

wherein
(a) m is an integer from 0 to 10; n is an integer from 0 to 10; and m+n is an integer from 0 to 10;
(b) R⁸ is independently selected from the group consisting of nil; —R³SR¹; hydrogen; substituted or unsubstituted C₁-C₈ alkyl; —R³OR⁴; —R³CO₂R⁴; —R³O₂CR⁴; —R³N(R⁴)₂; —R³[N(R⁵)₃]⁺; —R³N(R⁴)C(O)R⁴; —R³N(R⁴)C(S)R⁴; —R³N(R⁴)C(N)R⁴; —R³C(O)N(R⁴)₂; halogen; —R³C(O)R⁴; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings;
(c) R¹ is independently selected from the group consisting of hydrogen; —C(O)R⁷; —C(S)R⁷; —C(O)N(R⁷)₂; —C(O)OR⁷; —C(S)N(R⁷)₂; and —C(S)OR⁷; where R⁷ is hydrogen or substituted or unsubstituted C₁-C₈ alkyl;
(d) R³ is nil;
(e) R⁴ is independently selected from the group consisting of hydrogen; substituted or unsubstituted C₁-C₈ alkyl; and —R²SR¹;
(f) R⁵ is independently selected from the group consisting of substituted or unsubstituted C₁-C₁₅ alkyl; substituted or unsubstituted phenyl; benzyl; and —R²SR¹;
(g) L is selected from the group consisting of nil; —N(R⁸)—; [—N(R⁵)₂—]⁺; —S—; —O—; and —D—C(=E)—S—, where D is selected from the group consisting of covalent bond, O, or S, and E is O or S; and wherein (i) when L is —N(R$^8$)—, or when L is [—N(R$^5$)$_2$—]$^+$ and m is an integer from 1 to 10, R$^9$ is independently selected from the group consisting of nil; hydrogen; substituted or unsubstituted C$_1$–C$_{35}$ alkyl; R$^2$SR$^1$; and R$^{10}$;

(ii) when L is [—N(R$^5$)$_2$—]$^+$ and m=0, R$^9$ is selected from the group consisting of substituted or unsubstituted C$_1$–C$_{35}$ alkyl; R$^2$SR$^1$; and R$^{10}$; or (iii) when L is nil, —S—, —O—, or —D—C(=E)—S, R$^9$ is R$^{10}$;

(h) R$^{10}$ is a saturated, unsaturated, or aromatic monocyclic or polycylic carbocycle, or a saturated, unsaturated, or aromatic monocyclic or polycyclic and containing one or more heteroatoms; where said carbocycle or heterocycle is substituted with one or more R$^{11}$ substituents; and (i) each R$^{11}$ is independently selected from the group consisting of —R$^3$SR$^1$; hydrogen; substituted or unsubstituted C$_1$–C$_8$ alkyl; —R$^3$OR$^4$; —R$^3$CO$_2$R$^4$; —R$^3$O$_2$CR$^4$; —R$^3$N(R$^4$)$_2$; —R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; —R$^3$C(O)N(R$^4$)$_2$; halogen; —R$^3$C(O)R$^4$; hydroxy; substituted or unsubstituted arylalkyl; nitro; and unsubstituted or substituted aryl;

or (B) A and B are covalently linked together with C* to form a monocyclic or bicyclic ring having the following structure:

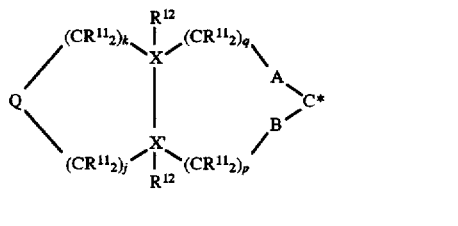

wherein (a) A and B are independently selected from the group consisting of nil, —O—, —S—, and —NR$^{12}$—;

(b) Q is selected from the group consisting of nil; —NR$^{12}$—; and [—N(R$^1$3)$_2$—]$^+$;

(c) X and X' are independently selected from C or N;

(d) R$^{12}$ is independently selected from the group consisting of nil; —R$^3$SR$^1$; hydrogen; substituted or unsubstituted C$_1$–C$_8$ alkyl; —R$^3$OR$^4$; —R$^3$CO2R$^4$; —R$^{302}$CR$^4$; —R$^3$N(R$^4$)$_2$; R$^3$[—N(R$^5$)$_3$]$^+$; —R$^3$N(R$^4$)C(O)R$^4$; —R$^3$C(O)N(R$^4$)$_2$; halogen; —R$^3$C(O)R$^4$; hydroxy; substituted or unsubstituted arylalkyl; nitro; and unsubstituted or substituted aryl;

(e) R$^{13}$ is selected from the group consisting of nil; substituted or unsubstituted C$_1$–C$_{15}$ alkyl; substituted or unsubstituted phenyl; benzyl; and —R$^2$SR$^1$;

(f) when Q is other than nil, k and j and k+j are integers from 0 to 5; when Q is nil, k and j and k+j are integers from 0 to 6; and (g) p and q and p+q are independently integers from 0 to 3; except that if Q is nil, then at least one of R$^{11}$ or R$^{12}$ is selected from the group consisting of —R$^3$N(R$^4$)$_2$; —R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; and —R$^3$C(O)N(R$^4$)$_2$.

Preferred phosphonocarboxylate compounds of formulas (I) and (II) have a nitrogen containing heterocycle linked to the phosphonocarboxylate geminal carbon via a linking chain. Included are phosphonocarboxylate compounds having the following general structures:

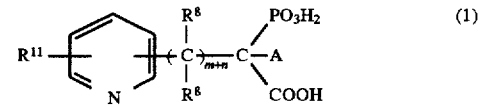
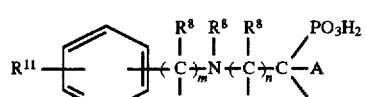
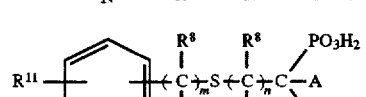
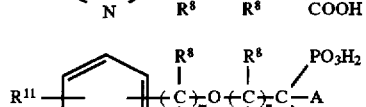
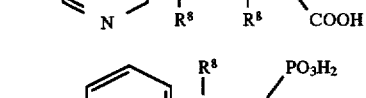
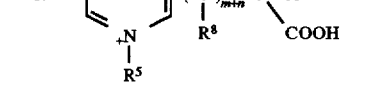
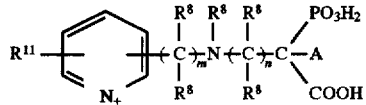
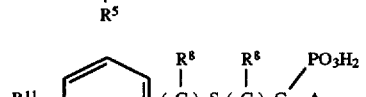
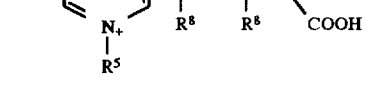
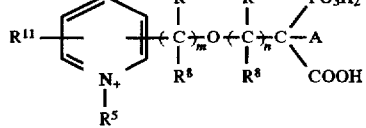

where the nitrogen containing heterocyle is a pyridine or pyridinium;

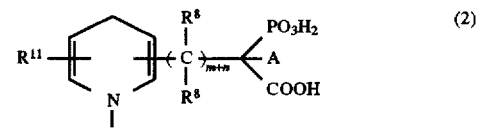
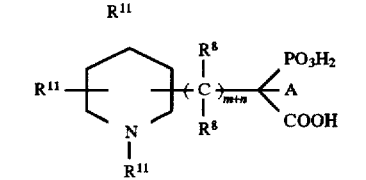

-continued

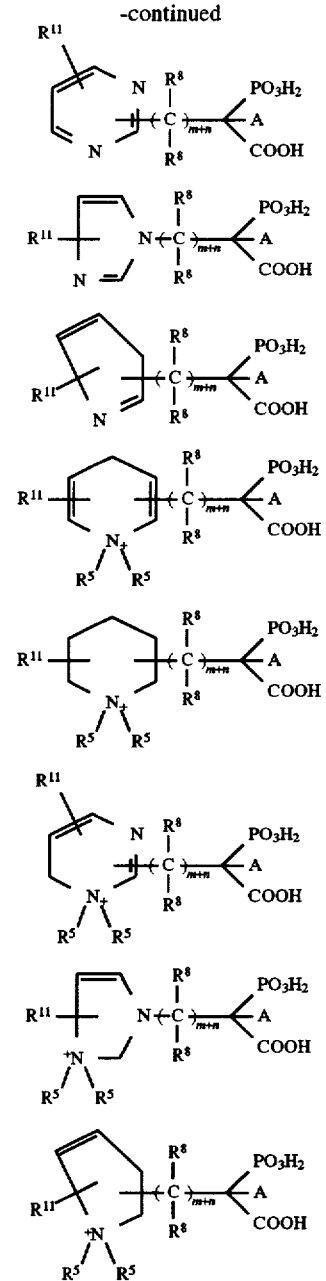

where the nitrogen containing heterocycle is a monocycle other than pyridine or pyridinium;

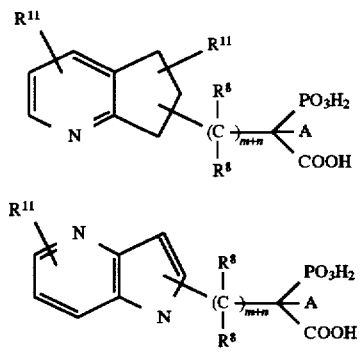

-continued

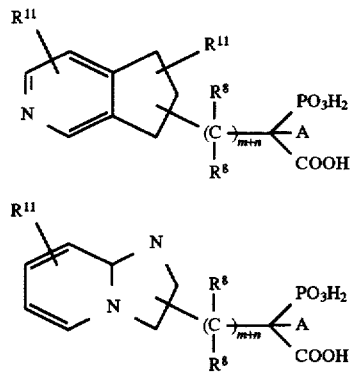

where the nitrogen containing heterocycle is a polycycle.

Also preferred are those phosphonocarboxylate compounds having a nitrogen containing heteroalkyl moiety linked to the phosphonate containing geminal carbon. Such compounds include those having the following structure, where $R^8$ and $R^9$ are non-cyclic substituents:

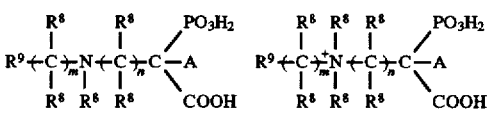

Also preferred are those compounds having the following structure, where $R^9$ is a cycloheptyl ring:

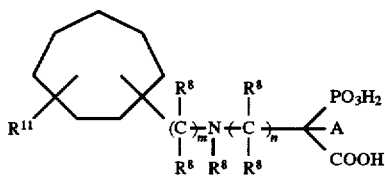

Also preferred are substituted or unsubstituted octahydro phosphonocarboxyl pyrindines, having the general structures:

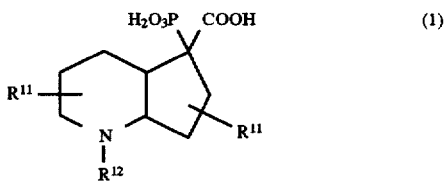

referred to herein as "unsubstituted or substituted octahydro-5-phosphono-5-carboxyl-1-pyrindines";

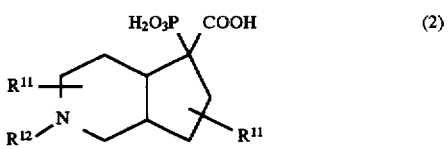

referred to herein as "unsubstituted or substituted octahydro-5-phosphono-5-carboxyl-2-pyrindines";

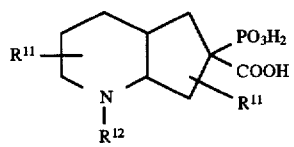
(3)

referred to herein as "unsubstituted or substituted octahydro-6-phosphono-6-carboxyl-1-pyrindines";

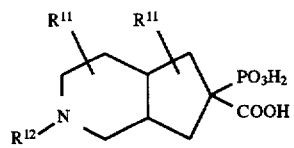
(4)

referred to herein as "unsubstituted or substituted octahydro-6-phosphono-6-carboxyl-2-pyrindines";

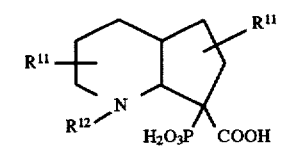
(5)

referred to herein as "octahydro-7-phosphono-7-carboxyl-1-pyrindines";

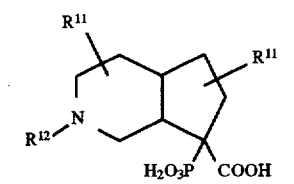
(6)

referred to herein as "octahydro-7-phosphono-7-carboxyl-2-pyrindines";

Also preferred are substituted or unsubstituted octahydro phosphonocarboxylate pyrindiniums having the general structures:

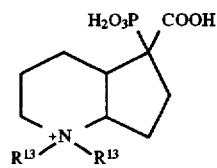
(1)

referred to herein as octahydro-5-phosphono-5-carboxyl-1-pyrindiniums";

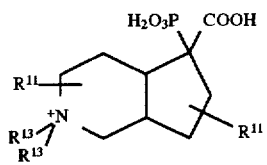
(2)

referred to herein as octahydro-5-phosphono-5-carboxyl-2-pyrindiniums";

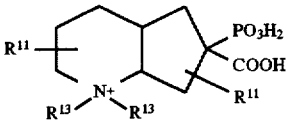
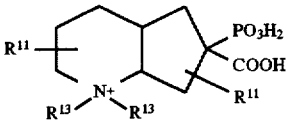
(3)

referred to herein as octahydro-6-phosphono-6-carboxyl-1-pyrindiniums";

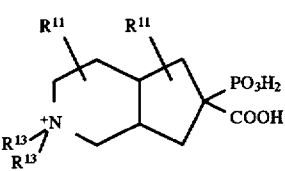
(4)

referred to herein as octahydro-6-phosphono-6-carboxyl-2-pyrindiniums";

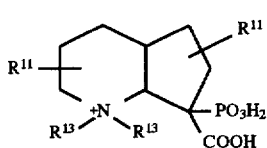
(5)

referred to herein as octahydro-7-phosphono-7-carboxyl-1-pyrindiniums";

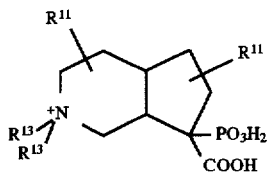
(6)

referred to herein as octahydro-7-phosphono-7-carboxyl-2-pyrindiniums";

Specific examples of compounds of the present invention are:

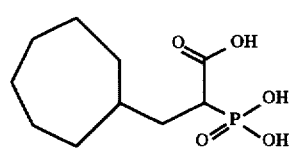
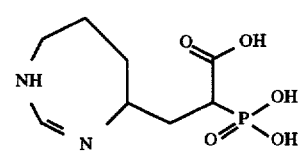
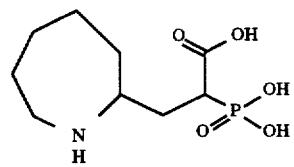

-continued
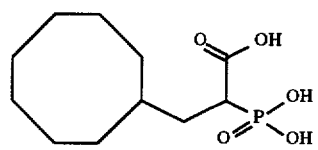
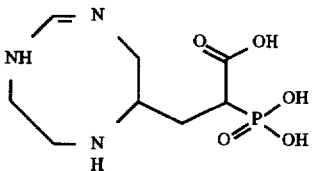
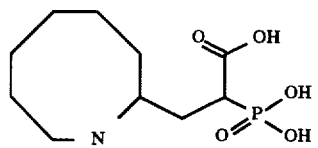
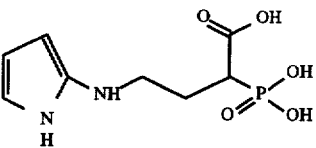
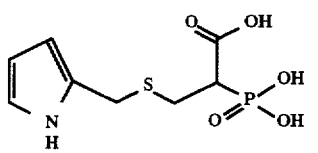
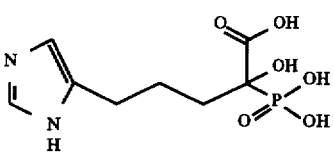
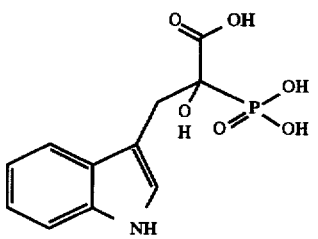
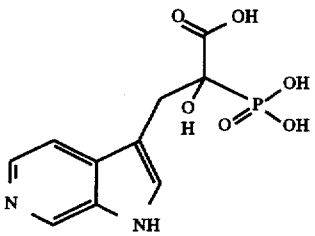
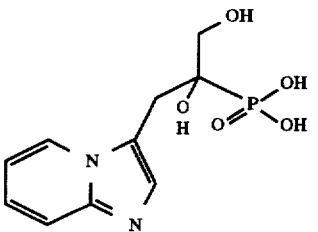
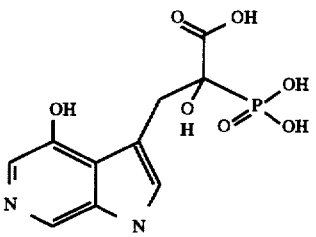
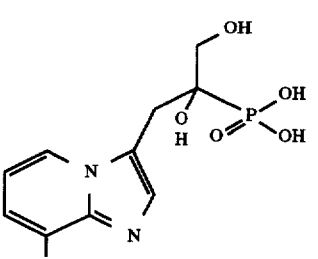
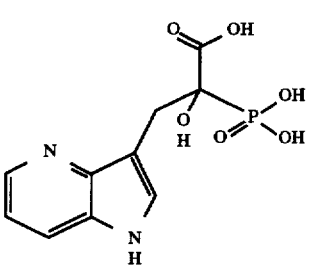
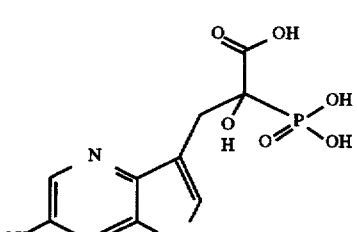
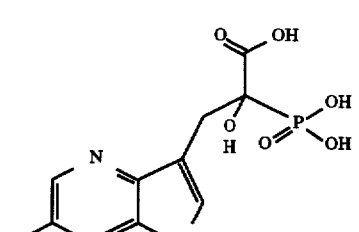

-continued
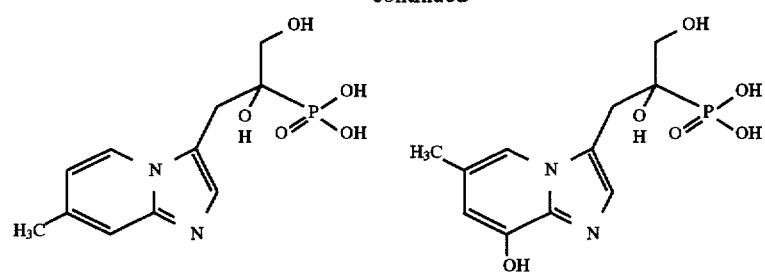
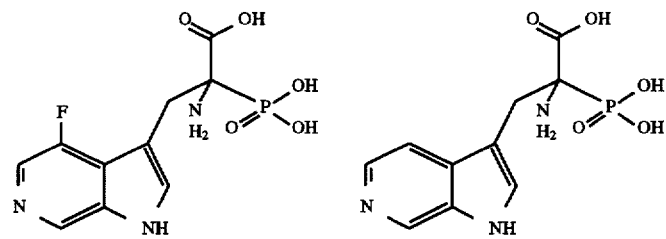
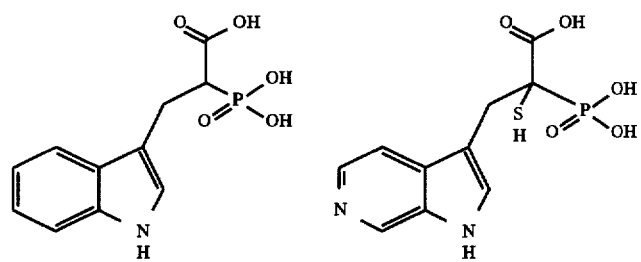
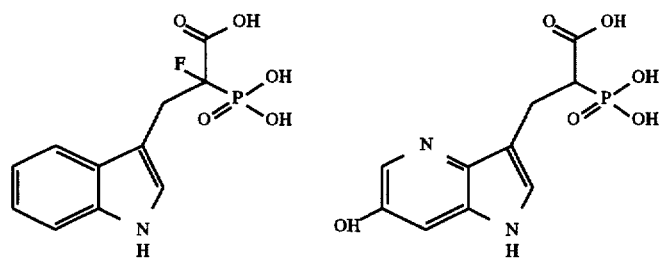
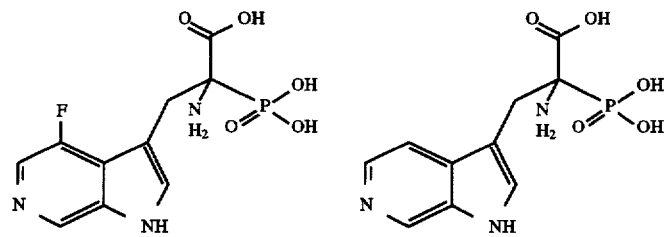
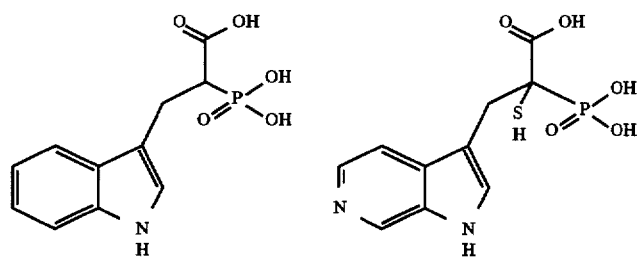

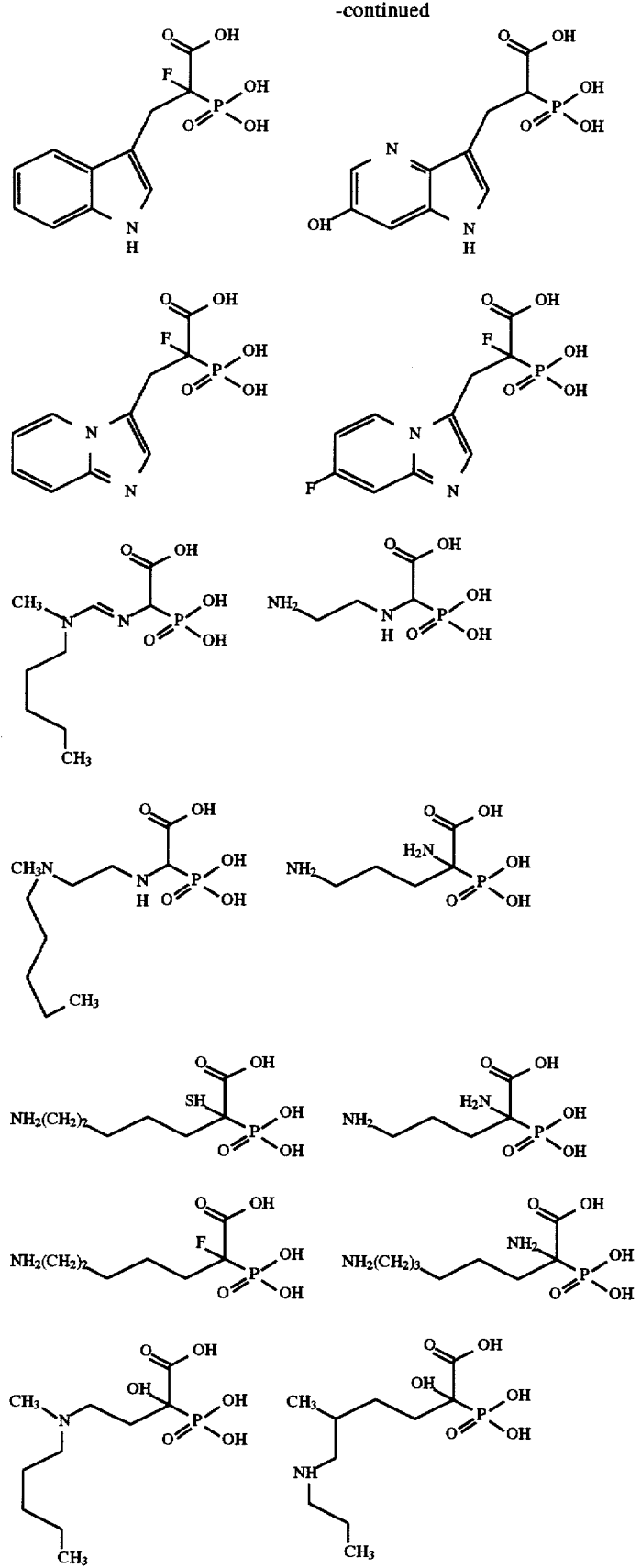

-continued
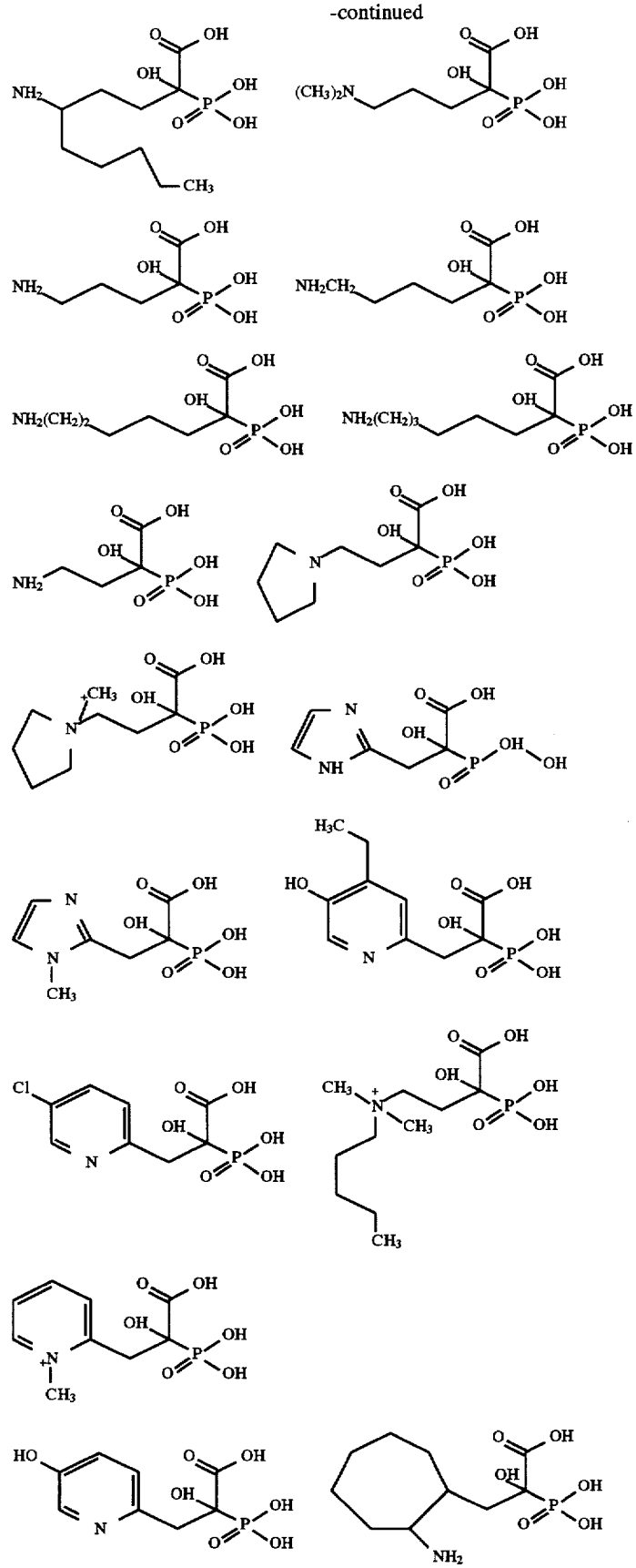

-continued
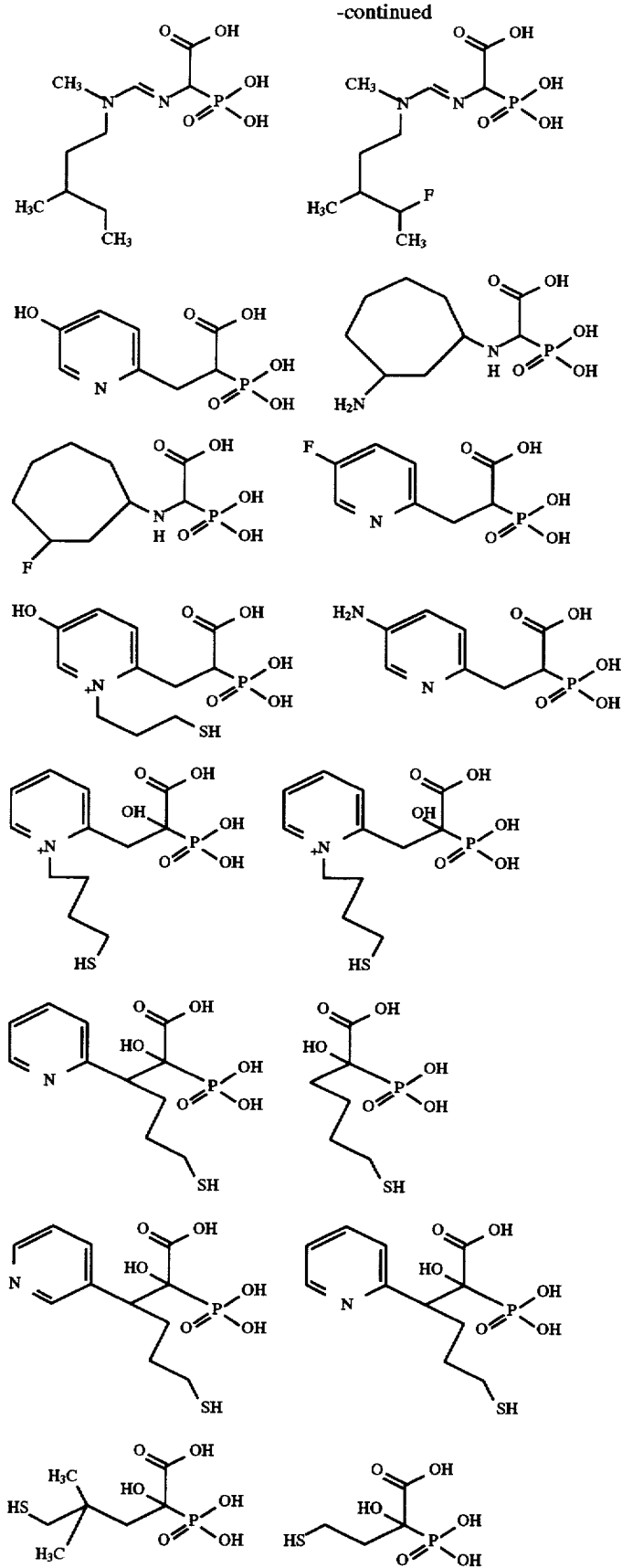

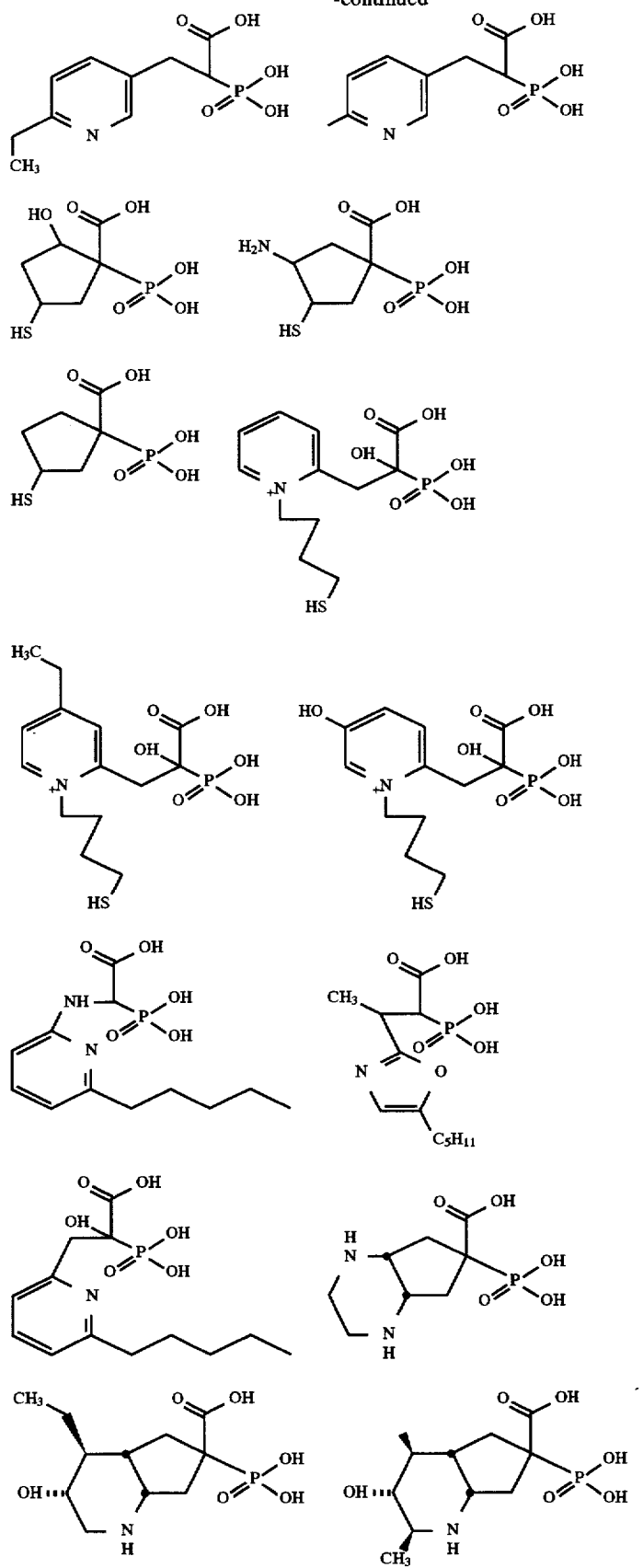

-continued
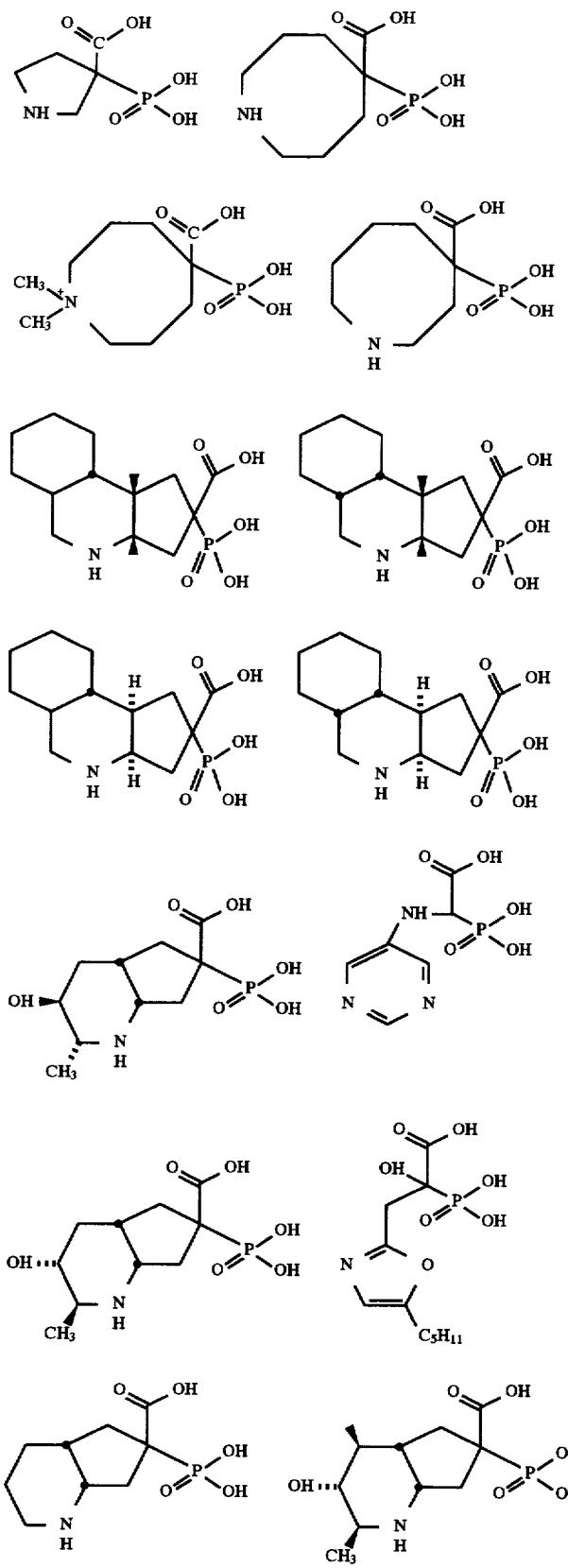

-continued
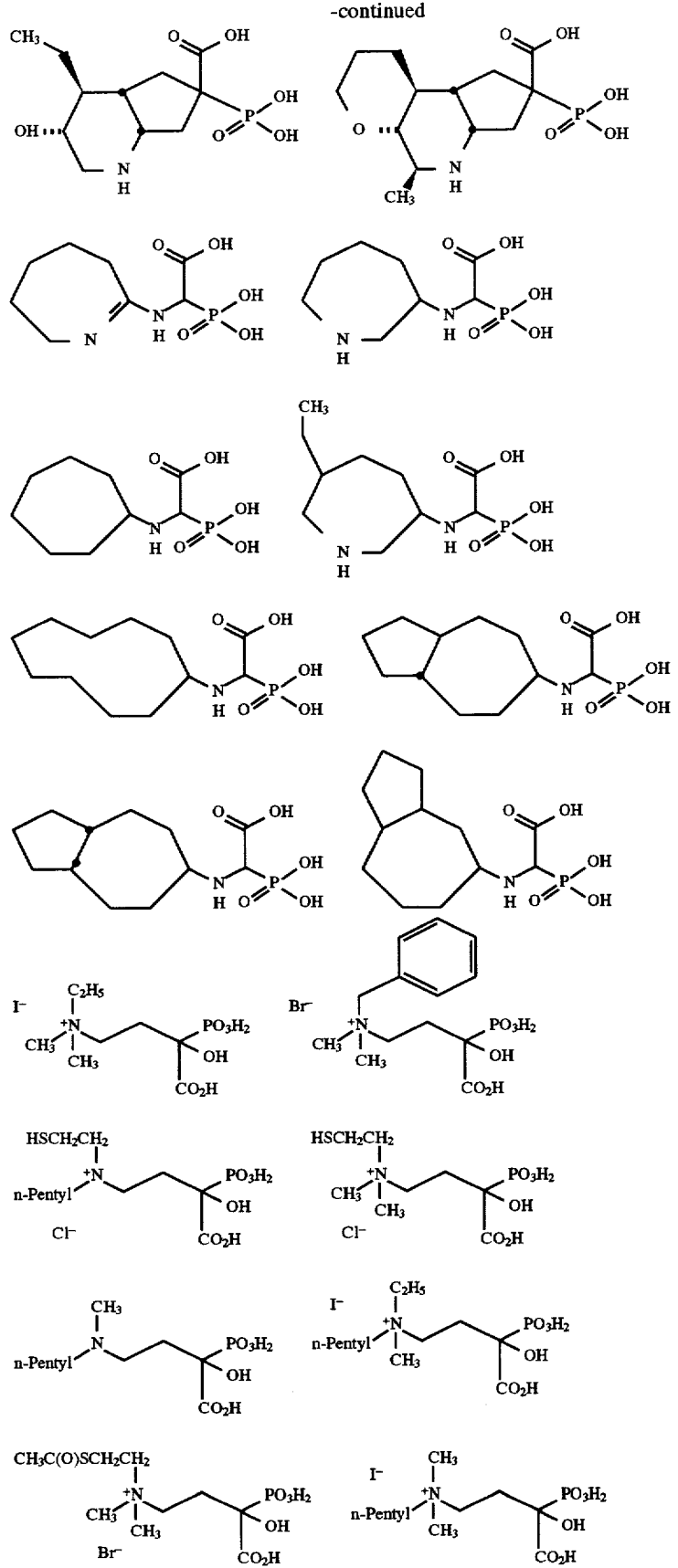

-continued
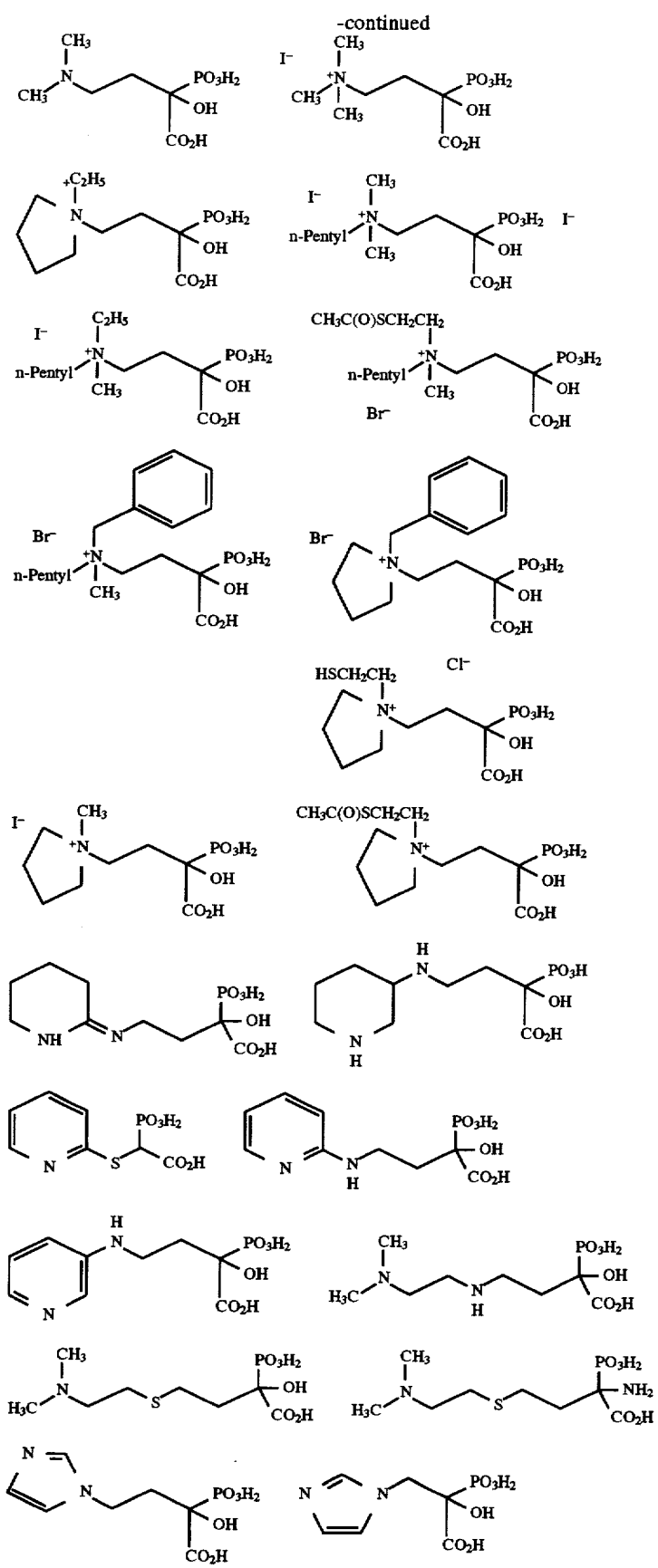

-continued
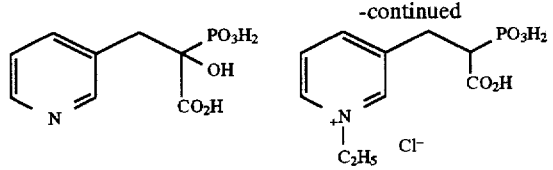
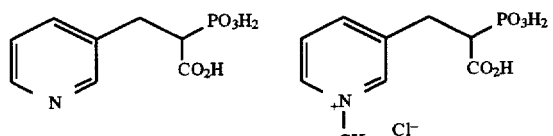
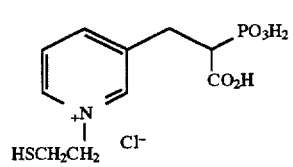
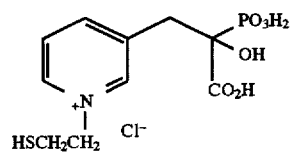
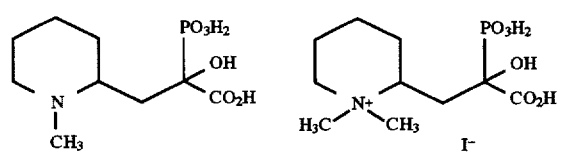
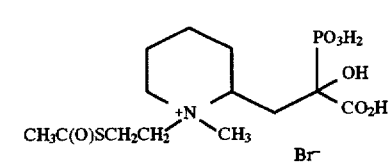
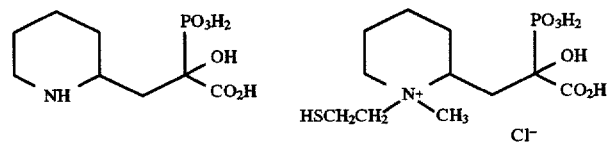
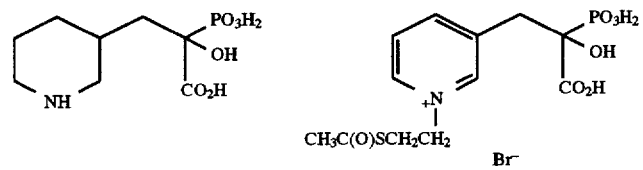
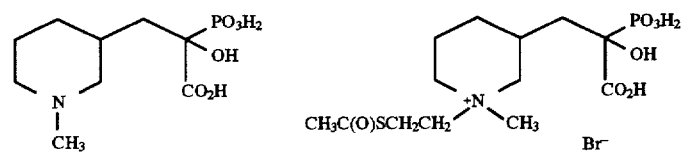
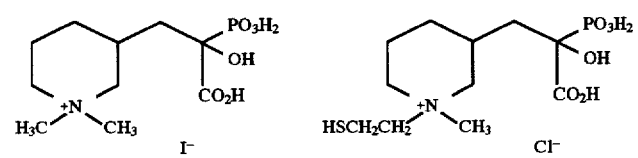

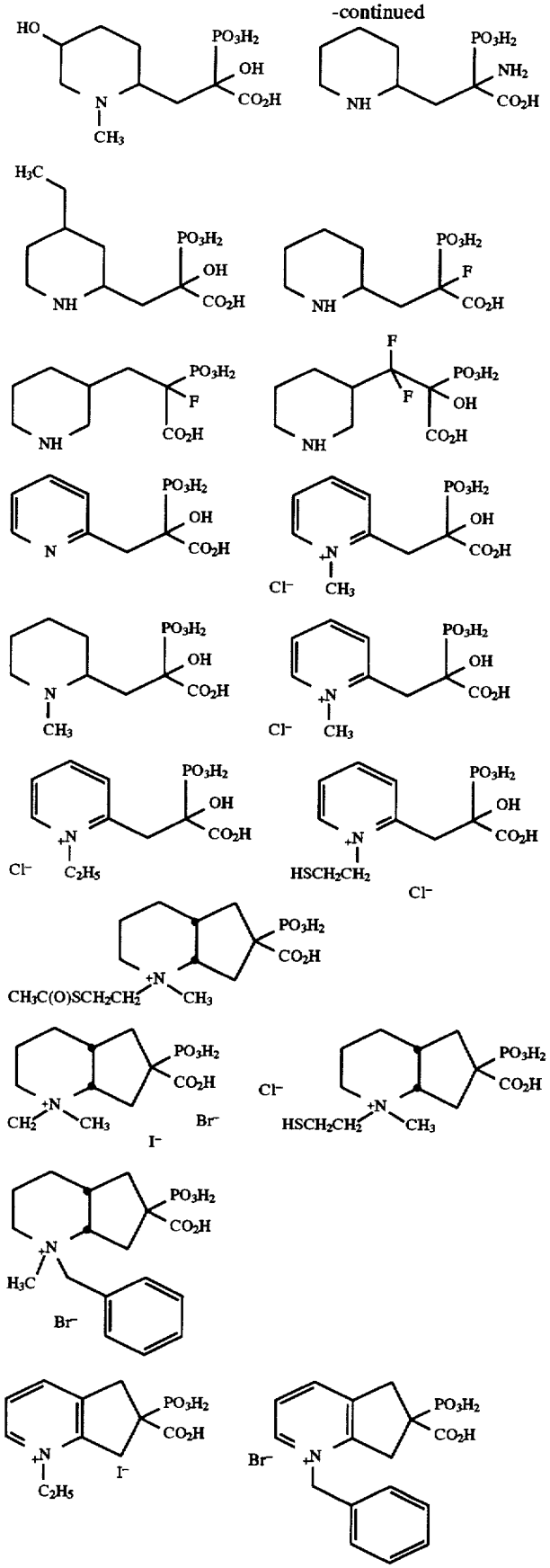

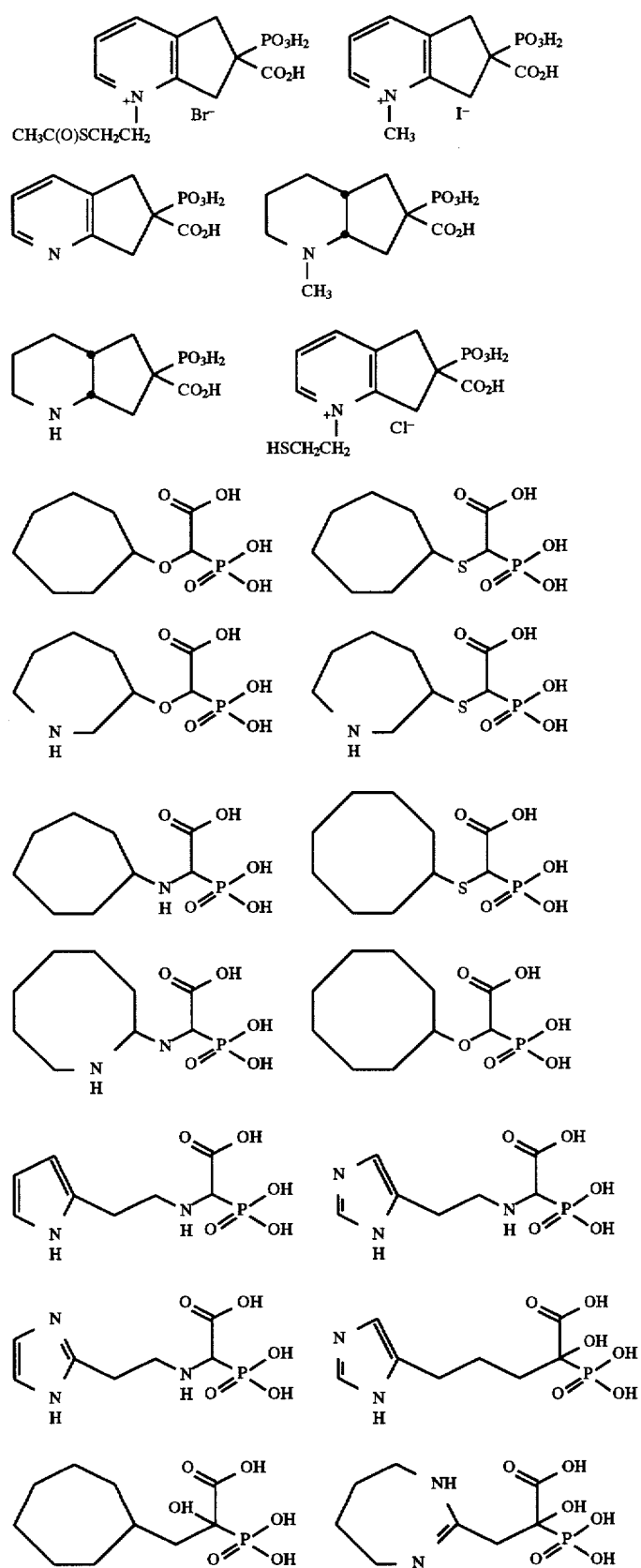

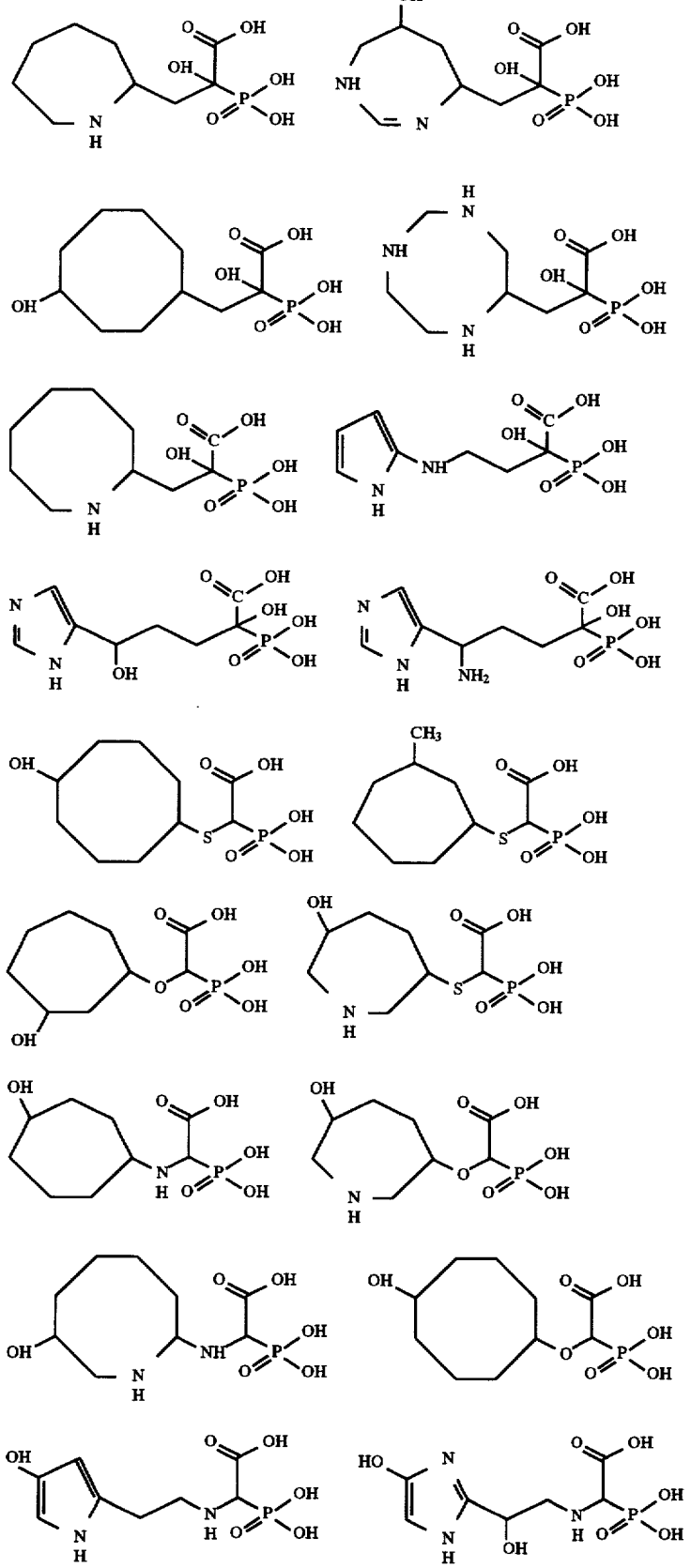

-continued

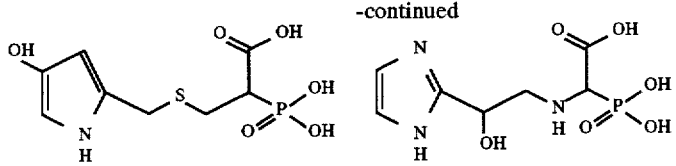

and the pharmaceutically-acceptable salts thereof. The term "pharmaceutically-acceptable salts", as used herein, means salts of the phosphonocarboxylate compounds which have the same general pharmacological properties as the acid form from which they are derived, and which are acceptable from a toxicity viewpoint. Pharmaceutically acceptable salts include alkali metals (e.g., sodium and potassium), alkaline earth metals (e.g., calcium and magnesium), non-toxic heavy metals (e.g., stannous and indium), and ammonium and low molecular weight substituted ammonium (e.g., mono-, di- and triethanolamine) salts. Preferred compounds are the sodium, potassium, and ammonium salts.

In order to determine and assess pharmacological activity, testing of the phosphonocarboxylate compounds in animals is carried out using various assays known to those skilled in the art. Thus, the in vivo bone antiresorptive activity may be conveniently demonstrated using an assay designed to test the ability of these compounds to inhibit the resorption of bone, which bone resorption is characteristic of abnormal calcium and phosphate metabolism. One such test known to those skilled in the art is the Schenk model. Another useful art-known test is the adjuvant arthritis test. Also useful is the in vitro hydroxyapatite crystal growth inhibition test. These and other appropriate tests for pharmacological activity are disclosed and/or referred to in Shinoda et al., *Calcified Tissue Internationals* 35, pp 87–99 (1983); Schenk et al., *Calcified Tissue Research*, 11, pp 196–214 (1973); Russell et al., *Calcified Tissue Research*, 6, pp 183–196 (1970); Muhlbauer and Fleisch, *Mineral Electrolyte Metab.*, 5, pp 296–303 (1981); Nancoflas et al., *Oral Biol.*, 15, 731 (1970); U.S. Pat. No. 3,683,080, to Francis, issued Aug. 8, 1972; U.S. Pat. No. 4,134,969, to Schmidt-Dunker, issued Jan. 16, 1979; and EPO Patent Application Publication No. 189,662, published Aug. 6, 1986; the disclosures of all these articles and patent specifications being incorporated herein by reference in their entirety. Certain of these tests for pharmacological activity are also described in more detail in the Examples provided hereinafter.

In addition to being useful for treating or preventing pathological conditions characterized by abnormal calcium or phosphate metabolism, the compounds of the present invention may have other uses. For example, the compounds of the present invention are believed to be useful as bone scanning agents after labeling with 99m-technetium. In addition, the compounds of the present invention are useful as sequestering agents for polyvalent metal ions, particularly di-(e.g. calcium and magnesium) and trivalent (e.g. indium) metal ions. Thus, the compounds of the present invention are useful as builders in detergents and cleansers, or for treating water. They are also useful as stabilizers for compounds. In addition, they may be useful in preventing the formation of tartar (i.e., calculus) and/or plaque on teeth. Finally, the compounds of the present invention may be useful as herbicides which are non-toxic to animals.

The phosphonocarboxylate compounds of the present invention are prepared from commercially-available materials according to non-limiting Examples 1 to 65.

Compositions Containing Novel
Phosphonocarboxylate Compounds

The phosphonocarboxylate compounds of the present invention may be administered to humans or other mammals by a variety of routes, including, but not limited to, oral dosage forms and injections (intravenous, intramuscular, intraperitoneal and subcutaneous). Numerous other dosage forms containing the novel phosphonocarboxylate compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the phosphonocarboxylate compound active ingredient, or mixtures thereof, and pharmaceutically-acceptable excipients.

The phrase "safe and effective amount", as used herein, means an amount of a compound or composition great enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular phosphonocarboxylate compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

Compounds of the present invention may comprise from about 0.1% to about 99.9% by weight of the pharmaceutical compositions of the present invention. Preferably the compounds of the present invention comprise from about 20% to about 80% by weight of the pharmaceutical compositions of the present invention.

Accordingly, the pharmaceutical compositions of the present invention include from 15–95% of a phosphonocarboxylate compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Suitable pharmaceutical compositions are described herein in Examples 66–68. It is well within the capabilities of one skilled in the art to vary the non-limiting examples described herein to achieve a broad range of pharmaceutical compositions.

The choice of a pharmaceutically-acceptable excipient to be used in conjunction with the phosphonate compounds of the present invention is basically determined by the way the phosphonate compound is to be administered. If the compound is to be injected, the preferred pharmaceutical carrier is sterile physiological saline, the pH of which has been adjusted to about 7.4. Suitable pharmaceutically-acceptable carriers for topical application include those suited for use in creams, gels, tapes and the like.

The pharmaceutically-acceptable carrier employed in conjunction with the phosphonocarboxylate compounds of the present invention is used at a concentration sufficient to provide a practical size to dosage relationship. The pharmaceutically-acceptable carriers, in total, may comprise from 0.1% to 99.9% by weight of the pharmaceutical compositions of the present invention, and preferably from 20% to 80%.

The preferred mode of administering the phosphonocarboxylate compound of the present invention is orally. The preferred unit dosage form is therefore tablets, capsules and the like, comprising a safe and effective amount of the phosphonate compound of the present invention. Preferably, the compositions comprise from about 1 mg P to about 600 mg P of a phosphonocarboxylate compound of the present invention. Pharmaceutically-acceptable carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

The rate of systemic delivery can be satisfactorily controlled by one skilled in the art, by manipulating any one or more of the following:

(a) the active ingredient;

(b) the pharmaceutically-acceptable excipients; so long as the variants do not interfere in the activity of the particular active ingredient selected;

(c) the type of the excipient, and the concomitant desirable thickness and permeability (swelling properties) of said excipients;

(d) the time-dependent conditions of the excipient itself and/or within the excipients;

(e) the particle size of the granulated active ingredient; and (f) the pH-dependent conditions of the excipients.

In particular, the solubility, acidity, and susceptibility to hydrolysis of the different phosphonocarboxylate active ingredients, such as acid addition salts, salts formed with the carboxylic group, e.g., alkali metal salts, alkaline earth metal salts, etc., and esters, e.g., alkyl, alkenyl, aryl, aralkyl, may be used as guidelines for the proper choice. In addition, suitable pH-conditions might be established within the oral dosage forms by adding a suitable buffer to the active ingredient in accordance with the desired release pattern.

As stated hereinabove, pharnaceutically-acceptable excipients include, but are not limited to, resins, fillers, binders, lubricants, solvents, glidants, disintegrants co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and anunonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof boric acid and the salts thereof, sorbic acid and the salts thereof chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropyl methylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% is glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

The term "mg P", as used herein, means the weight of the phosphorus atom present in an amount of a phosphonocarboxylate compound of the present invention. This unit is used to standardize the amount of the phosphonocarboxylate compounds of the present invention to be used in the pharmaceutical compositions and methods of the present inventions. For example, 2-hydroxy-2-phosphono-3-(3-pyridyl)propionic acid has a molecular weight of 247 g/mole, of which 12.5% (31 g/mole) is due to the phosphorus atom present in this molecule. One milligram of this compound is therefore calculated to have 0.125 mg P. Thus, to prepare a pharmaceutical composition containing 0.125 mg P of this compound, the composition should contain 1 mg of the compound; and to dose 0.125 mg P/kg of this compound to a 50 kg patient, the patient would be dosed with 50 mg of this compound.

Method for Treating or Preventing Diseases Characterized by Abnormal Calcium and Phosphate Metabolism Another aspect of the present invention is methods for treating or preventing diseases characterized by abnormal calcium and phosphate metabolism. Such methods comprise administering to a human or lower animal in need of such treatment a safe and effective amount of a phosphonocarboxylate compound of the present invention.

The preferred mode of administration is oral, but other known methods of administration are contemplated as well, e.g., dermato mucosally (for example, dermally, rectally and the like) and parenterally (for example, by subcutaneous injection, intramuscular injection, intra-articular injection, intravenous injection and the like). Inhalation is also included. Thus, specific modes of administration include, without limitation, oral, transdermal, mucosal, sublingual, intramuscular, intravenous, intraperitoneal, and sub cutaneous administration, as well as topical application.

The term "abnormal calcium and phosphate metabolism", as used herein, means (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, heterotopic ossification, and osteolytic bone metastases. The second category includes, but is not limited to, myositis ossificans progressive, calcinosis universalis, and such afflictions as arthritis, osteoarthritis, neuritis, bursitis, tendonitis and other inflammatory conditions which predispose involved tissue to deposition of calcium phosphates.

The term "rheumatoid arthritis" as used herein, means a chronic systemic and articular inflammatory disorder of unknown etiology. It is characterized by destruction of articular cartilage, ligaments, tendons, and bone.

The term "osteoarthritis" as used herein, means a non-inflammatory disorder of the movable joints. It is characterized by deterioration and abrasion of the articular cartilage; and new bone formation at the joint surface.

The terms "person at risk" and "person in need of such treatment", as used herein, mean any human or lower animal which suffers a significant risk of abnormal calcium and phosphate metabolism if left untreated, and any human or lower animal diagnosed as being afflicted with abnormal calcium and phosphate metabolism. For example, post-menopausal women; persons undergoing certain steroid therapy; persons on certain anticonvulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteopetrosis as a side effect; persons diagnosed as suffering from myositis ossificans progressiva or calcinosis universalis; and persons afflicted with arthritis, osteoarthritis, neuritis, bursitis, tendonitis and other inflammatory conditions which predispose involved tissue to deposition of calcium phosphate.

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of phosphonocarboxylate compounds of the present invention will vary with the particular condition being treated, the age and physical condition of the patient being treated, the severity of the condition, the duration of the treatment, the nature of concurrent therapy, the specific diphosphonate employed, the particular pharmaceutically-acceptable carrier utilized, and like factors within the knowledge and expertise of the attending physician. However, single dosages can range from 0.01 mg P to 3500 mg P, or from 0.0002 to 70 mg P/kg of body weight (based on a body weight of 50 kg). Preferred single dosages are from 1 mg P to 600 mg P, or from 0.02 to 12 mg P/kg of body weight (based on a body weight of 50 kg).

Up to four single dosages per day may be administered. Daily dosages greater than 500 mg P/kg are not required to produce the desired effect and may produce undesirable side effects. The higher dosages within this range are, of course, required in the case of oral administration because of limited absorption.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE 1

Synthesis of 4-(N,N-Dimethylamino)-2-hydroxy-2-phosphonobutanoic Acid

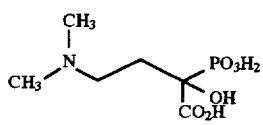

I. Synthesis of Ethyl 2-oxo-3-butenoate

A solution of 41 g (0.30 mole) of ethyl oxalyl chloride in 500 ml of anhydrous diethyl ether is stirred under nitrogen atmosphere in a −78° bath. To this is added dropwise over 1–2 hours 100 ml (0.10 mole) of a solution of vinylmagnesium bromide (1.0 molar, in tetrahydrofuran). The reaction mixture is stirred for 30 min. longer at −78°, and then is allowed to warm to 0° over about 2 hours. The reaction mixture is concentrated on a rotary evaporator under vacuum to get rid of excess ethyl oxalyl chloride. The residue is resuspended in ether, and the resulting mixture is stirred in an ice bath. To it is slowly added a solution of 2 g (0.01 mole) of triethylamine in 10 ml ethanol.

The mixture is allowed to warm to room temperature, and is filtered. The filter cake is washed well with ether. The filtrate is evaporated down, and the residue is partitioned between 200 ml of ether and 200 ml of water. The water layer is extracted with 100 ml more ether. The combined ether layers are washed twice with 100 ml of 1 N aqueous acetic acid, twice with 100 ml of 1 N aqueous NaHCO$_3$, and once with 100 ml of saturated NaCl solution. The organic layer is dried with Na$_2$SO$_4$ and is evaporated dry on a rotary evaporator to yield the crude product. This is purified by flash chromatography on silica gel to afford ethyl 2-oxo-3-butenoate as an oil.

II. Synthesis of Ethyl 4-(N,N-Dimethylamino)-2-oxobutanoate

To a stirred solution of 12.8 g (0.10 mole) of ethyl 2-oxo-3-butenoate in 200 ml of anhydrous ether under a nitrogen atmosphere (in an ice bath) is added over about 1 hr. a cold solution of 4.5 g (0.10 mole) of dimethylamine in 200 ml of anhydrous ether. The reaction is stirred at 0° for several hours, and then at 20°–25° for one day. The solvent is removed, and the resulting crude product is purified by flash chromatography on silica gel using chloroform/methanol as eluant.

III. Synthesis of Ethyl 2-Diethoxyphosphinyl-4-(N,N-dimethylamino)-2-hydroxybutanoate A mixture of 8.05 g (0.05 mole) of ethyl 4-(N,N-dimethylamino)-2-oxobutanoate in 31 g (0.225 mole) of diethyl phosphite is stirred at 20°–30° for 3–5 days. The excess diethyl phosphite is removed on a rotary evaporator under high vacuum at a bath temperature of 50°–70° to yield the crude product as a viscous oil. This is purified by chromatography on silica gel using chloroform/methanol as eluant.

IV. Synthesis of 4-(N,N-Dimethylamino)-2-hydroxy-2-phosphonobutanoic acid

Hydrolysis of the above triethyl ester (3.2 g) is accomplished by refluxing it in 6 N HCl for 18 hours. The aqueous HCl is removed under vacuum, and the resulting residue is dissolved in water, treated with activated charcoal, and filtered. The filtrate is concentrated to a few ml, and ethanol is added to precipitate the product. This is collected by filtration and dried in a desiccator to provide 4-(N,N-dimethylamino)-2-hydroxy-2-phosphonobutanoate.

EXAMPLE 2

Synthesis of N-(3-Carboxy-3-hydroxy-3-phosphonopropyl-N,N,N-trimethylammonium Iodide

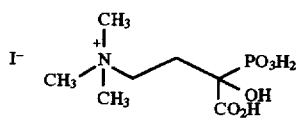

A solution of 2.27 g (0.01 mole) of 4-(N,N-dimethylamino)-2-hydroxy-2-phosphonobutanoic acid (prepared as described in Example 1) in 20 ml water and 30 ml ethanol is adjusted to pH 7.0 by addition of 1N aqueous NaOH. To this is added 7.1 g (0.05 mole) of methyl iodide, and the reaction is stirred at 30°–50° for one day. The reaction is evaporated to dryness under reduced pressure. The resulting residue is dissolved in distilled water, and is treated with cation exchange resin in H+ form. The resin is filtered off, the aqueous solution is concentrated to a few ml, and acetone is added dropwise to precipitate the product. This is purified by recrystallization from water/acetone to give N-(3-carboxy-3-hydroxy-3-phosphonopropyl)-N,N,N-trimethylammonium iodide.

EXAMPLE 3

Synthesis of N-(3-Carboxy-3-hydroxy-3-phosphonopropyl)-N,N-dimethyl-N-thylammonium Iodide

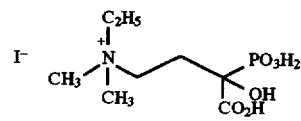

A solution of 2.27 g (0.01 mole) of 4-(N,N-dimethylamino)-2-hydroxy-2-phosphonobutanoic acid (prepared as described in Example 1) in 20 ml water and 40 ml ethanol is adjusted to pH 7.0 by addition of 1N aqueous NaOH. To this is added 6.24 g (0.04 mole) of ethyl iodide, and the reaction is stirred at 30°–50° for one day. The reaction is evaporated to dryness under reduced pressure. The resulting residue is dissolved in distilled water, and is treated with cation exchange resin in H+ form. The resin is filtered off, the aqueous solution is concentrated to a few ml, and acetone is added dropwise to precipitate the product. This is purified by recrystallization from water/acetone to give N-(3-carboxy-3-hydroxy-3-phosphonopropyl)-N,N-dimethyl-N-ethylammonium iodide.

EXAMPLE 4

Synthesis of N-(3-Carboxy-3-hydroxy-3-phosphonopropyl)-N,N-dimethyl-N-(phenylmethyl) ammonium Bromide

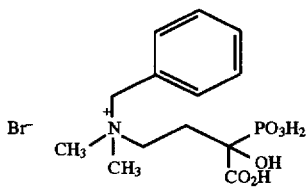

A solution of 2.27 g (0.01 mole) of 4-(N,N-dimethylamino)-2-hydroxy-2-phosphonobutanoic acid (prepared as described in Method 1) in 10 ml water and 40 ml ethanol is adjusted to pH 7.0 by addition of 1N aqueous NaOH. To this is added 5.13 g (0.03 mole) of benzyl bromide, and the reaction is heated at about 50° for one day. The reaction is evaporated to dryness under reduced pressure. The resulting residue is slurried in water and the mixture is extracted several times with CHCl₃. The aqueous solution is evaporated a little to get rid of traces of chloroform, and is treated with cation ion exchange resin in H+ form. The resin is filtered off, the aqueous solution is concentrated to a few ml, and ethanol is added dropwise to precipitate the product. This is purified by recrystallization from water/ethanol to give N-(3-carboxy-3-hydroxy-3-phosphonopropyl)-N,N-dimethyl-N-(phenylmethyl) ammonium bromide.

EXAMPLE 5

Synthesis of N-(2-(Acetylthio)ethyl)-N-(3-carboxy-3-hydroxy-3-phosphonopropyl)-N,N-dimethylammonium Bromide

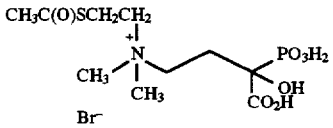

A solution of 2.27 g (0.01 mole) of 4-(N,N-dimethylamino)-2-hydroxy-2-phosphonobutanoic acid (prepared as described in Method 1) in 20 ml water and 40 ml ethanol is adjusted to pH 7.0 by addition of 1N aqueous NaOH. To this is added 9.16 g (0.05 mole) of S-acetyl-2-bromoethanethiol, and the reaction is heated at 40°–80° for several hours. The reaction is evaporated to dryness under reduced pressure. The resulting residue is triturated with acetone several times (acetone extracts are discarded). The remaining solid is dissolved in distilled water, and is treated with cation exchange resin in H+ form. The resin is filtered off, the aqueous solution is concentrated to a few ml, and acetone is added dropwise to precipitate the product. This is purified by recrystallization from water/acetone to give N-(2-(acetylthio)ethyl)-N-(3-carboxy-3-hydroxy-3-phosphonopropyl)-N,N-dimethylammonium bromide.

EXAMPLE 6

Synthesis of N-(3-carboxy-3-hydroxy-3-phosphonopropyl)-N,N-dimethyl-N-(2-thioethyl) ammonium Chloride

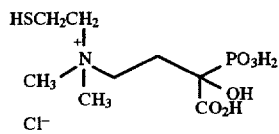

A solution of 1 g of N-(2-(acetylthio)ethyl)-N-(3-carboxy-3-hydroxy-3-phosphonopropyl)-N,N-dimethylammonium bromide in 50 ml of water is treated with anion exchange resin in chloride form. The solution is concentrated to 20 ml, and 20 ml of 12 N HCl is added. The solution is heated at reflux under a nitrogen atmosphere for 12 hours, and is then evaporated dry. The residue is dissolved in 50 ml of fresh 6 N HCl and is again evaporated to dryness. It is then taken up in a few ml of water and is reprecipitated with ethanol to yield N-(3-carboxy-3-hydroxy-3-phosphonopropyl)-N,N-dimethyl-N-(2-thioethyl)ammonium chloride.

All of these operations are carried out under N2 atmosphere using deoxygenated solvents to minimize disulfide formation.

EXAMPLE 7

Synthesis of 2-Hydroxy4-((N-methyl-N-pentyl) amino)-2-phosphonobutanoic Acid

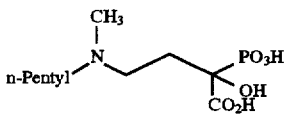

I. Synthesis of Ethyl 4-((-Methyl-N-pentyl)amino)-2-oxobutanoate

A solution of 10.1 g (0.10 mole) of N-methyl-N-pentylamine and 12.8 g (0.10 mole) of ethyl 2-oxo-3-butenoate (prepared as in Example 1) in 50 ml of toluene under a nitrogen atmosphere is stirred at 30°–50° for several hours. The solvent is removed, and the resulting crude product is purified by flash chromatography on silica gel.

II. Synthesis of Ethyl 2-Diethoxyphosphinyl-2-Hydroxy-4-((N-methyl-N-pentyl)amino)butanoate A mixture of 10.9 g (0.05 mole) of ethyl 4-((N-methyl-N-pentyl)amino)-2-oxobutanoate in 31 g (0.225 mole) of diethyl phosphite is stirred at 20°–30° for 5 days. The excess diethyl phosphite is removed on a rotary evaporator under high vacuum at a bath temperature of 50°–70° to yield the crude product as an oil. This is purified by chromatography on silica gel using chloroform/methanol as eluant.

III. Synthesis of 2-Hydroxy4-((N-methyl-N-pentyl) amino)-2-phosphonobutanoic acid Hydrolysis of the above triethyl ester (3.2 g) is accomplished by refluxing it in 6 N HCl for 18 hours. The aqueous HCl is removed under vacuum, and the resulting residue is dissolved in water, treated with activated charcoal, and filtered. The filtrate is concentrated to a few ml, and ethanol is added to precipitate the product. This is collected by filtration and dried in a desiccator to provide 2-hydroxy-4-(N-methyl-N-pentylamino)-2-phosphonobutanoate.

EXAMPLE 8

Synthesis of N-(3-Carboxy-3-hydroxy-3-phosphonopropyl)-N,N-dimethyl-N-pentylammonium Iodide

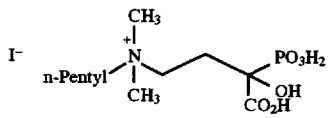

This compound is made by the method of Example 2, starting with 2-hydroxy-4-(N-methyl-N-pentylamino)-2-phosphonobutyric acid.

EXAMPLE 9

Synthesis of N-(3-Carboxy-3-hydroxy-3-phosphonopropyl)-N-ethyl-N-methyl-N-pentylammonium Iodide

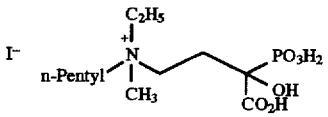

This compound is made by the method of Example 3, starting with 2-hydroxy-4-(N-methyl-N-pentylamino)-2-phosphonobutyric acid.

EXAMPLE 10

Synthesis of N-(3-Carboxy-3-hydroxy-3-phosphonopropyl)-N-methyl-N-pentyl-N-henylmethyl)ammonium Bromide

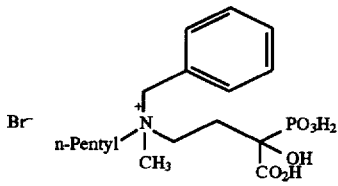

This compound is made by the method of Example 4, starting with 2-hydroxy-4-(N-methyl-N-pentylamino)-2-phosphonobutyric acid.

EXAMPLE 11

Synthesis of N-(2-Acetylthioethyl)-N-(3-Carboxy-3-hydroxy-3-phosphonopropyl)-N-methyl-N-pentylammonium Bromide

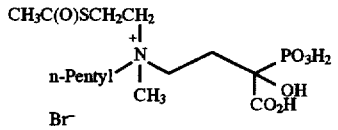

This compound is made by the method of Example 5, starting with 2-hydroxy-4-(N-methyl-N-pentylamino)-2-phosphonobutyric acid.

EXAMPLE 12

Synthesis of N-(3-Carboxy-3-hydroxy-3-phosphonopropyl)-N-methyl-N-pentyl-N-(2-thioethyl)ammonium Chloride

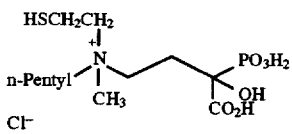

This compound is made by the method of Example 6, starting with N-(2-(acetylthio)ethyl)-N-(3-carboxy-3-hydroxy-3-phosphonopropyl)-N-methyl-N-pentylanunonium bromide.

EXAMPLE 13

Synthesis of 2-Hydroxy-4-(1-imidazolyl)-2-phosphonobutanoic Acid

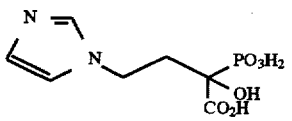

I. Synthesis of Ethyl 4-(1-Imidazolyl)-2-oxobutanoate

A mixture of 6.8 g (0.10 mole) of imidazole and 12.8 g (0.10 mole) of ethyl 2-oxo-3-butenoate (prepared as in Example 1) in 50 ml of tetrahydrofuran under a nitrogen atmosphere is stirred at 50°–80° for several hours. The solvent is removed, and the resulting crude product is purified by flash chromatography on silica gel.

II. Synthesis of Ethyl 2-Diethoxyphosphinyl-2-hydroxy-4-(1-midazolyl)butanoate

A mixture of 9.81 g (0.05 mole) of ethyl 4-(1-imidazolyl)-2-oxobutanoate in 31 g (0.225 mole) of diethyl phosphite is stirred at 20°–30° for about 4 days. The excess diethyl phosphite is removed on a rotary evaporator under high vacuum at a bath temperature of 50°–70° to yield the crude product. This is purified by chromatography on silica gel using chloroform/methanol as eluant.

III. Synthesis of 2-Hydroxy4-(1-imidazolyl)-2-phosphonobutanoic acid

Hydrolysis of the above triethyl ester (5 g) is accomplished by refluxing it in 100 ml of 6 N HCl for 18 hours. The aqueous HCl is removed under vacuum, and the resulting residue is dissolved in water, treated with activated charcoal, and filtered. The filtrate is concentrated to a few ml, and acetone is added to precipitate the product. This is collected by filtration recrystallized from water/ethanol to give the purified product, which is dried in a desiccator to provide 2-hydroxy4-(1-imidazolyl)-2-phosphonobutanoic acid.

EXAMPLE 14

Synthesis of 2-Hydroxy-2-phosphono-4-(1-pyrrolidinyl)butanoic Acid

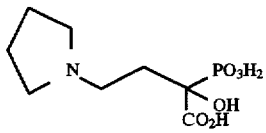

I. Synthesis of Ethyl 2-Oxo-4-(1-pyrrolidinyl)propanoate

A solution of 7.1 g (0.10 mole) of pyrrolidine and 12.8 g (0.10 mole) of ethyl 2-oxo-3-butenoate (prepared by the method in Example 1) in 50 ml of toluene is stirred at 30°–40° for one day under a nitrogen atmosphere. The solvent is removed, and the resulting crude product is purified by flash chromatography on silica gel.

II. Synthesis of Ethyl 2-Diethoxyphosphinyl-2-hydroxy-4-(1-pyrrolidinyl)butanoate A mixture of 9.96 g (0.05 mole) of ethyl 2-oxo-4-(1-pyrrolidinyl)butanoate in 31 g (0.225 mole) of diethyl phosphite is stirred at 20°–30° for 3–6 days. The excess diethyl phosphite is removed on a rotary evaporator under high vacuum at a bath temperature of 50°–70° to yield the crude product as a viscous oil. This is purified by chromatography on silica gel using chloroform/methanol as eluant.

III. Synthesis of 2-Hydroxy-2-phosphono4-(1-pyrrolidinyl)butanoic acid

Hydrolysis of the above triethyl ester (3.2 g) is accomplished by refluxing it in 6 N HCl for 18 hours. The aqueous HCl is removed under vacuum, and the resulting residue is dissolved in water, treated with activated charcoal, and filtered. The filtrate is concentrated to a few ml, and ethanol is added to precipitate the product. This is collected by filtration and dried in a desiccator to provide 2-hydroxy-2-phosphono4-(1-pyrrolidinyl)butanoic acid.

EXAMPLE 15

Synthesis of N-(3-Carboxy-3-hydroxy-3-phosphonopropyl)-N-methylpyrrolidinium Iodide

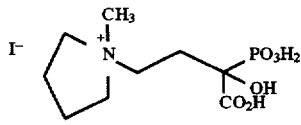

This compound is made by the method of Example 2, starting with 2-hydroxy-2-phosphono-4-(1-pyrrolidinyl)butanoic acid.

EXAMPLE 16

Synthesis of N-(3-Carboxy-3-hydroxy-3-phosphonopropyl)-N-ethylpyrrolidinium Iodide

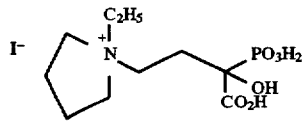

This compound is made by the method of Example 3, starting with 2-hydroxy-2-phosphono-4-(1-pyrrolidinyl)butanoic acid.

EXAMPLE 17

Synthesis of N-(3-Carboxy-3-hydroxy-3-phosphonopropyl)-N-(phenylmethyl)pyrrolidinium Bromide

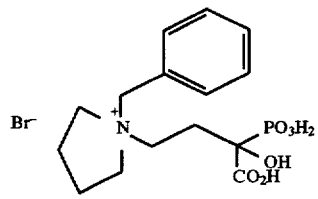

This compound is made by the method of Example 4, starting with 2-hydroxy-2-phosphono-4-(1-pyrrolidinyl)butanoic acid.

EXAMPLE 18

Synthesis of N-(2-(Acetylthio)ethyl)-N-(3-Carboxy-3-hydroxy-3-phosphonopropyl)pyrrolidinium Bromide

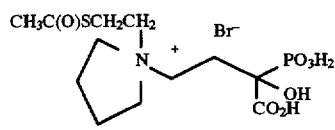

This compound is made by the method of Example 5, starting with 2-hydroxy-2-phosphono-4-(1-pyrrolidinyl)butanoic acid.

EXAMPLE 19

Synthesis of N-(3-Carboxy-3-hydroxy-3-phosphonopropyl)-1-N-(2-thioethyl)pyrrolidinium Chloride

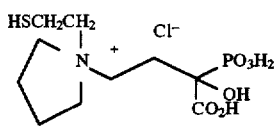

This compound is made by the method of Example 6, starting with N-(2-(acetylthio)ethyl)-N-(3-carboxy-3-hydroxy-3-hosphonopropyl)pyrrolidinium bromide.

EXAMPLE 20

Synthesis of 4-Amino-2-hydroxy-2-phosphonobutanoic Acid

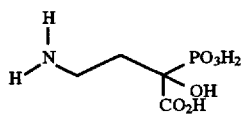

Method 1:

I. Synthesis of Ethyl 2-Oxo-4-phthalimidobutanoate

To a solution of 12.8 g (0.10 mole) of ethyl 2-oxo-3-butenoic acid (prepared as in Example 1)) in 75 ml of anhydrous ethanol is added phthalimide (14.7g, 0.10 mole)

and potassium phthalimide (0.92 g. 0.005 mole). The mixture is heated at 50°–80° for about a day. It is cooled in an ice bath. and is quenched with 20 ml of 0.5 N HCl. The THF is removed under vacuum, and the residue is partitioned between water and $CH_2Cl_2$. The water layer is extracted further with $CH_2Cl_2$, and the combined extracts are washed with aqueous 5% $NaHCO_3$ solution and dried with $MgSO_4$. The crude product, obtained after removal of the solvent, is chromatographed on silica gel to afford the desired ester.

II. Synthesis of Ethyl 2-Diethoxyphosphinyl-2-hydroxy-4-phthalimidobutanoate

A mixture of 13.76 g (0.05 mole) of ethyl 2-oxo-4-phthalimidobutanoate in 31 g (0.225 mole) of diethyl phosphite is stirred at 20°–30° for several days. The excess diethyl phosphite is removed on a rotary evaporator under vacuum at a bath temperature of 50°–70° to give the crude product. This is purified by chromatography on silica gel using chloroform/methanol as eluant.

III. Synthesis of 4-Amino-2-hydroxy-2-phosphonobutanoic Acid

The above triester (5.0 g) is suspended in 100 ml of 12 N HCl and the reaction mixture is heated under reflux for 1–2 days. The reaction is cooled to ambient temperature, and phthalic acid is removed by filtration. The filtrate is evaporated dry in vacuum, and the residue is suspended in water and washed with chloroform to further remove phthalic acid. The water layer is concentrated to 5–10 ml, and ethanol is added dropwise with stirring to precipitate the desired product, which is collected by filtration. Recrystallization of this solid from water/ethanol affords pure 4-amino-2-hydroxy-2-phosphonobutanoic acid.

EXAMPLE 21

Synthesis of 5-Amino-2-hydroxy-2-phosphonopentanoic Acid

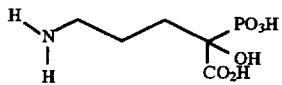

Method 1:

I. Synthesis of Ethyl 2-Diethoxyphosphinyloxiranecarboxylate

To a solution of 2.36 g (0.01 mole) of ethyl 2-diethoxyphosphinylpropenoate (J. Org. Chem., 43, 1259 (1978)) in 150 ml of methylene chloride is added 50 ml of 0.5 N aqueous $NaHCO_3$ solution. The mixture is stirred rapidly at ambient temperature, while meta-chloroperbenzoic acid (0.01 mole) is slowly added. After stirring for about 6 hours longer, the methylene chloride layer is separated off and is washed with 0.5 N NaOH solution and then with water. It is dried with $Na_2SO_4$ and is evaporated to dryness to give ethyl 2-diethoxyphosphinyloxiranecarboxylate as an oil.

II. Synthesis of Ethyl 4-Cyano-2-diethoxyphosphinyl-2-hydroxybutanoate

Under a nitrogen atmosphere in dry glassware, a solution of 4.1 g (0.10 mole) of acetonitrile in about 30 ml of anhydrous tetrahydrofuran is stirred at −78° in a Dry Ice/acetone bath. To this is slowly added, via syringe, a cold solution of 0.10 mole of lithium diisopropylamide in tetrahydrofuran. The reaction mixture is stirred for 30–60 minutes at −78°, and to it is then added rapidly 2.52 g (0.10 mole) of ethyl 2-diethoxyphosphinyloxiranecarboxylate. The reaction is stirred at −78° for about 30 minutes, and then is quenched by addition of 0.1 N ethanolic HCl. The mixture is warmed to ambient temperature, and the solvent is removed under vacuum. The resulting residue is partitioned between water and $CH_2Cl_2$, and the water layer is further extracted with $CH_2Cl_2$. The combined organic layers are washed with $NaHCO_3$ solution, then with water, dried ($MgSO_4$) and the solvent is removed to give the cyanotriester as an oil which is purified by flash chromatography on silica gel.

III. Synthesis of 4-Cyano-2-hydroxy-2-phosphonobutanoic Acid

A solution of 2.77 g (0.01 mole) of ethyl 4-cyano-2-diethoxyphosphinyl-2-hydroxybutanoate in 30 ml of $CHCl_3$ is treated with 10.7 g (0.07 mole) of trimethylsilyl bromide. The solution is stirred at 50° for about one day. It's cooled to room temperature, and water is added. The mixture is stirred for about 30 minutes. The layers are separated, and the water layer is washed several times with $CHCl_3$. The water layer is evaporated to dryness under vacuum, and the residue is triturated with acetone to convert it to a solid (filter to collect it), which is 4-cyano-2-hydroxy-2-phosphonobutanoic acid.

IV. Synthesis of 5-Amino-2-hydroxy-2-phosphonopentanoic Acid

The hydrogenation of 4-cyano-2-hydroxy-2-phosphonobutanoic acid is carried out using the hydrogenation technique of Freifelder (J. Am. Chem. Soc., 8, 2386 (1960)). The cyano compound (2.09 g; 0.01 mole) is placed in 20 ml of 10% methanolic ammonia. Rhodium on alumina (5%) catalyst (0.5 g) is added, and the mixture is hydrogenated at 40 PSI on a Parr apparatus for several hours (until uptake of hydrogen is complete). The catalyst is filtered off, and the filtrate is evaporated dry. The residue treated with cation exchange resin in H+ form to convert the material to acid form. The solution containing it is evaporated to dryness under vacuum. The product is purified by dissolving the residue in water, adding ethanol to give a precipitate, and collecting the solids by filtration. Further purification is accomplished by again recrystallizing from water/ethanol.

Method 2:

I. Synthesis of Ethyl 4-Cyano-2-oxo-butanoate

To a solution of 12.8 g (0.10 mole) of ethyl 2-oxo-3-butenoic acid (prepared as in Example 1) in 100 ml of ethanol and 50 ml of water is added 6.5 g (0.10 mole) of potassium cyanide. The mixture is stirred at 30°–50° for about one hour, during which time a solution of 6.0 g (0.10 mole) of acetic acid in 20 ml of ethanol is slowly dripped in. After addition is complete, the mixture is cooled to room temperature and the solvent is removed under vacuum. The residue is partitioned between water and $CH_2Cl_2$, the layers separated, and the water extracted further with $CH_2Cl_2$. The combined organic layers are dried ($Na_2SO_4$) and the solvent is removed to give the crude product. This is purified by flash chromatography on silica gel to give ethyl 4-cyano-2-oxo-butanoate as an oil.

II. Synthesis of Ethyl 2-Diethoxyphosphinyl4-cyano-2-hydroxybutanoate

A mixture of 7.75 g (0.05 mole) of ethyl 4-cyano-2-oxo-butanoate in 31 g (0.225 mole) of diethyl phosphite is stirred at 20°–30° for 3–4 days. The excess diethyl phosphite is removed on a rotary evaporator under high vacuum at a bath temperature of 50°–700 to yield the crude product as an oil. This is purified by chromatography on silica gel.

III. Synthesis of 4-Cyano-2-hydroxy-2-phosphonobutanoic Acid

A solution of 2.77 g (0.01 mole) of ethyl 4-cyano-2-diethoxyphosphinyl-2-hydroxybutanoate in 30 ml of $CHCl_3$ is treated with 10.7 g (0.07 mole) of trimethylsilyl bromide. The solution is stirred at 50° for about one day. It's cooled to room temperature, and water is added. The mixture is stirred for about 30 minutes. The layers are separated, and the water layer is washed several times with CHCl$_3$. The water layer is evaporated to dryness under vacuum, and the residue is triturated with acetone to convert it to a solid (filter to collect it), which is 4-cyano-2-hydroxy-2-phosphonobutanoic acid.

IV. Synthesis of 5-Amino-2-hydroxy-2-phosphonopentanoic Acid

The hydrogenation of 4-cyano-2-hydroxy-2-phosphonobutanoic acid is carried out using the hydrogenation technique of Freifelder (J. Am. Chem. Soc., 82 2386 (1960)). The cyano compound (2.09 g; 0.01 mole) is placed in 20 ml of 10% methanolic ammonia. Rhodium on alumina (5%) catalyst (0.5 g) is added, and the mixture is hydrogenated at 40 PSI on a Parr apparatus for several hours (until uptake of hydrogen is complete). The catalyst is filtered off and the filtrate is evaporated dry. The residue treated with cation exchange resin in H+ form to convert the material to acid form. The solution containing it is evaporated to dryness under vacuum. The product is purified by dissolving the residue in water, adding ethanol to give a precipitate, and collecting the solids by filtration. Further purification is accomplished by again recrystallizing from water/ethanol.

EXAMPLE 22

Synthesis of 2-Hydroxy-3-(1-Imidazolyl)-2-phosphonopropanoic Acid

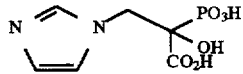

I. Synthesis of Ethyl 2-Oxo-3-(1-imidazolyl)propanoate

A mixture of 19.5 g (0.10 mole) of ethyl bromopyruvate and 13.8 g (0.20 mole) of imidazole in about 200 ml of dry tetrahydrofuran is heated at reflux for 15 hours. The solvent is removed on a rotary evaporator, and the residue is treated with 200 ml of 1 N aqueous sodium bicarbonate solution. The mixture is extracted several times with chloroform, and the extracts are combined and dried (MgSO$_4$) to afford the crude product. This is purified by flash-chromatography on silica gel, using methylene chloride/ethanol nixture as eluant.

II. Synthesis of Triethyl 2-Hydroxy-3-(1-imidazolyl)-2-phosphonopropanoate

A suspension of 14.62 g (0.10 mole) of ethyl 2-oxo-3-(1-imidazolyl)propanoate in 62 g (0.45 mole) of diethyl phosphite is stirred at 20°-30° for 3-7 days. The excess diethyl phosphite is removed on a rotary evaporator under high vacuum at a bath temperature of 50°-70°. The resulting viscous residue is purified by chromatography on silica gel using chloroform/methanol as eluant.

III. Synthesis of 2-Hydroxy-3-(1-imidazolyl)-2-phosphonopropanoic Acid

The above triethyl ester (0.02 mole) is hydrolyzed in refluxing 6 N HCl (100 ml) for 18 hours. The reaction mixture is evaporated to dryness under vacuum. The resulting residue is treated with activated charcoal, filtered, and the filtrate is evaporated to near dryness. Addition of ethanol causes precipitation of the product, which is collected by filtration.

EXAMPLE 23

Synthesis of 2-Phosphono-3-(3-pyridyl)propanoic Acid

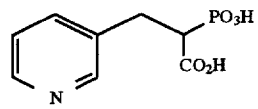

I. Synthesis of Methyl 2-dimethoxyhosphinyl-3-(3-pyridyl)propanoate

Solution A is prepared by adding 2.00 g (0.050 mole) of NaH (60% in mineral oil) slowly to a solution of 8.09 ml (0.050 mole) of trimethyl phosphonoacetate in 50 ml of anhydrous dimethylsulfoxide (DMSO) to minimize foaming. The reaction mixture is a light yellow solution. (All of the above is done in oven-dried glassware at ambient temperature under a nitrogen atmosphere.)

To a mixture of 8.20 g (0.050 mole) of 3-picolyl chloride hydrochloride in 50 ml of anhydrous DMSO under nitrogen is slowly added (over 5 minutes to minimize foaming) 2.0 g (0.050 mole) of NaH (60% in mineral oil). The reaction is stirred for 75 minutes. To this mixture is then added Solution A over a 40 minute period. The resulting solution is stirred at ambient temperature for 18 hours. The solvent is removed under vacuum to yield a sticky, reddish-brown residue. This is taken up in 100 ml of saturated aqueous NH$_4$Cl solution, and is extracted with 3×100 ml of CH$_2$Cl$_2$. The combined extracts are dried with MgSO$_4$ and are evaporated in vacuo to afford 11.3 g of oil. Mineral oil is extracted from this with 3×100 ml of hexane, leaving 9.6 g of red-brown material. This is purified by preparative HPLC, using acetone as eluant on a silica gel column, affording 2.5 g of trimethyl 2-phosphono-3-(3-pyridyl)propanoate.

II. Synthesis of 2-Phosphono-3-(3-pyridyl)propanoic Acid

The triester is hydrolyzed by refluxing it (2.0 g) with 50 ml of 6 N HCl for 3-6 hours. The water and HCl are removed under vacuum. The resulting residue is redissolved in water and evaporated again to dryness to complete the removal of HCl. It is once more dissolved in a few ml H$_2$0, and ethanol is slowly added, causing the desired product to precipitate.

EXAMPLE 24

Synthesis of 3-(2-Carboxy-2-phosphonoethyl)-1-methylpyridinium Chloride

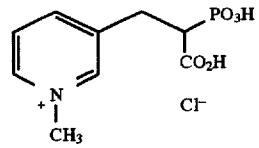

A solution of 2.5 g (0.009 mole) of methyl 2-dimethoxyphosphinyl-3-(3-pyridyl)propanoate (prepared as in Example 23) and 2.25 ml (0.020 mole) of methyl iodide in 5 ml of anhydrous tetrahydrofuran is stirred at ambient temperature for 18 hours. A gum forms during this time. The solvent is poured off, and the gum is washed twice with 10 ml portions of ether.

The ester groups are hydrolyzed by dissolving the gum in 25 ml of 6 N HCl, and refluxing the resulting solution for 3 hours. The solution is cooled, and is extracted several times with chloroform to remove I₂. The aqueous layer is evaporated under vacuum to give a brownish gum. This is dissolved in 20–25 ml of hot, absolute ethanol. The solution is cooled, and 10–15 ml of dry acetone is added. Upon stirring this solution for several hours a solid forms. This is collected by filtration and washed with acetone and then with ether to give 2.0 g of pale yellowish solid. This is further purified by stirring it with 10 ml of anhydrous ethanol for 2–3 hrs, then filtering and washing with a few ml ethanol, then with acetone, and finally with ether. There is obtained 1.82 g (71% yield) of 3-(2-carboxy-2-phosphonoethyl)-1-methylpyridinium chloride.

EXAMPLE 25

Synthesis of 3-(2-Carboxy-2-phosphonoethyl)-1-ethylpyridinium Chloride

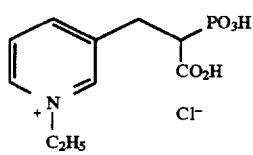

A solution of 2.5 g (0.009 mole) of methyl 2-dimethoxyphosphinyl-3-(3-pyridyl)propanoate (prepared as in Example 23) and 3.12 g (0.020 mole) of ethyl iodide in 5 ml of anhydrous tetrahydrofuran is stirred at ambient temperature for 18 hours. A gum forms during this time. The solvent is poured off, and the gum is washed twice with 10 ml portions of ether.

The ester groups are hydrolyzed by dissolving the gum in 25 ml of 6 N HCl, and refluxing the resulting solution for 3 hours. The solution is cooled, and is extracted several times with chloroform to remove I₂. The aqueous layer is evaporated under vacuum to give a gum. This is dissolved in 20–25 ml of hot, absolute ethanol and is treated with activated charcoal and filtered. The filtrate is cooled, and 10–15 ml of dry acetone is added. Upon stirring this solution for several hours a solid forms. This is collected by filtration and is recrystallized once more from water/ethanol/acetone to yield 3-(2-carboxy-2-phosphonoethyl)-1-ethylpyridinium chloride.

EXAMPLE 26

Synthesis of 3-(2-Carboxy-2-phosphonoethyl)-1-(2-thioethyl)pyridinium Chloride

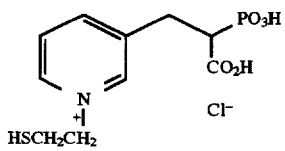

A solution of 2.5 g (0.009 mole) of methyl 2-dimethoxyphosphinyl-3-(3-pyridyl)propanoate (prepared as in Example 23) and 3.66 g (0.020 mole) of S-acetyl-2-bromoethanethiol in 5 ml of anhydrous tetrahydrofuran is stirred at ambient temperature for 2–3 days. A gum forms during this time. The solvent is poured off, and the gum is washed twice with 10 ml portions of ether.

The ester groups are hydrolyzed by dissolving the gum in 50 ml of 6 N HCl, and refluxing the resulting solution for 24 hours under a nitrogen atmosphere. The solution is cooled, and is extracted several times with chloroform. The aqueous layer is evaporated under vacuum, and the resulting residue is dissolved in 20–25 ml of hot, absolute ethanol and is treated with activated charcoal and filtered. The filtrate is concentrated, and several ml of dry acetone are added. Upon stirring this solution for several hours a solid forms. This is collected by filtration and is recrystallized once more from water/ethanol/acetone to yield 3-(2-carboxy-2-phosphonoethyl)-1-(2-thioethyl)pyridinium chloride.

EXAMPLE 27

Synthesis of 2-Hydroxy-2-phosphono-3-(3-pyridyl)propanoic Acid

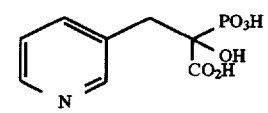

I. Synthesis of Ethyl 2-Dimethoxyphosphinyl-2-hydroxy-3-(3-pyridyl)propanoate

A suspension of 11.64 g (0.060 mole) of ethyl 2-oxo-3-(3-pyridyl)propanoate (synthesized as in Liebig's Annalen der Chemie, 703, 37–43 (1967)) in 30.13 g (0.274 mole) of dimethylphosphite is stirred at 20°–30° for 3 days. The excess dimethylphosphite is removed on a rotary evaporator under high vacuum at a bath temperature of about 55° to afford 21.1 g of viscous orange oil. This is purified by flash chromatography on silica gel using chloroform/methanol (20/1) as eluant. About 6–8 g of pure product is obtained as an oil.

II. Synthesis of 2-Hydroxy-2-phosphono-3-(3-pyridyl)propanoic Acid

About 6 g of the above ester is dissolved in 50 ml of 12 N HCl, and the solution is heated at reflux for 5 hours. The solution is concentrated on a rotary evaporator to yield a viscous oil. This is dissolved in about 5 ml water, and the flask is scratched with a glass rod causing a solid to form. The solid is collected by filtration and washed with a few ml water. After drying at 76° under high vacuum overnight there is obtained about 2.7 g of pure 2-hydroxy-2-phosphono-3-(3-pyridyl)propanoic acid as a white solid.

EXAMPLE 28

Synthesis of 342-Carboxy-2-hydroxy-2-phosphonoethyl)-1-methylpyridinium Chloride

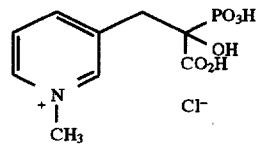

This compound is prepared according to the method given in Example 24, starting with ethyl 2-dimethoxyphosphinyl-2-hydroxy-3-(3-pyridyl)propanoate.

EXAMPLE 29

Synthesis of 3-(2-Carboxy-2-hydroxy-2-phosphonoethyl)-1-ethylpyridinium Chloride

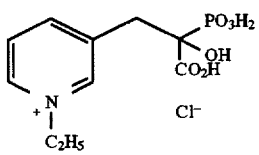

This compound is prepared according to the method given in Example 25, starting with ethyl 2-dimethoxyphosphinyl-2-hydroxy-3-(3-pyridyl)propanoate.

EXAMPLE 30

Synthesis of 3-(2-Carboxy-2-hydroxy-2-phosphonoethyl)-1-(2-thioethyl)pyridinium Chloride

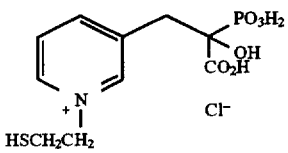

This compound is prepared according to the method given in Example 26, starting with ethyl 2-dimethoxyphosphinyl-2-hydroxy-3-(3-pyridyl)propanoate.

EXAMPLE 31

Synthesis of Dihydro-6-phosphone-1-pyrindine-6-carboxylic Acid

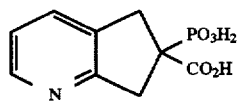

To 70 ml of anhydrous dimethylsulfoxide (DMSO), stirred under nitrogen atmosphere in an ice bath, is added 1.6 g of 60% NaH in mineral oil (0.04 mole). When this is dissolved, there is added dropwise to the solution (still stirred at 0°) a solution of triethyl phosphonoacetate (4.48 g, 0.02 mole) of DMSO. The reaction mixture is stirred at room temperature for one hour. To it is then added dropwise a solution of 3.48 g (0.02 mole) of 2,3-bis(chloromethyl) pyridine (see D. Tsuda, et al., Chem. Pharm. Bull. 1, 142 (1953)) in 15 ml of DMSO. The mixture is stirred at room temperature for one hour, and then at 800 for 1–3 hours. The DMSO is removed under vacuum, and the residue is purified by flash chromatography on silica gel using 5–15% ethanol in methylene chloride gradient eluant.

The above ester is hydrolyzed by refluxing it in 6 N HCl for 20 hours. Upon concentration of the reaction solution and cooling it in ice a precipitate forms. This is recrystallized from water to afford dihydro-6-phosphono-1-pyrindine-6-carboxylic acid.

EXAMPLE 32

Synthesis of Dihydro-6-carboxy-1-methyl-6-phosphono-1-pyrindinium Iodide

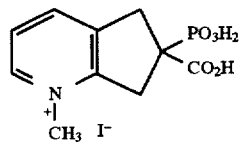

This compound is made by the method of Example 2, starting with dihydro-6-phosphono-1-pyrindine-6-carboxylic acid.

EXAMPLE 33

Synthesis of Dihydro-6-carboxy-1-ethyl-6-phosphono 1-pyridinium Iodide

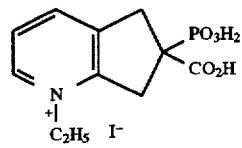

This compound is made by the method of Example 3, starting with dihydro-6-phosphono-1-pyridine-6-carboxylic acid.

EXAMPLE 34

Synthesis of Dihydro-6-carboxy-1-phenylmethyl-6-phosphono-1-pyrindinium Bromide

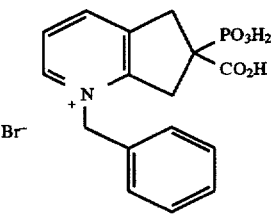

This compound is made by the method of Example 4, starting with dihydro-6-phosphono-1-pyridine-6-carboxylic acid.

EXAMPLE 35

Synthesis of Dihydro-1-(2-(acetylthio)ethyl)-6-carboxy-6-phosphono-1-pyrindinium Bromide

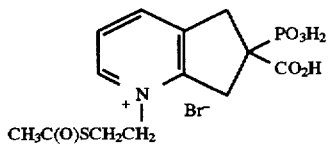

This compound is made by the method of Example 5, starting with dihydro-6-phosphono-1-pyrindine-6-carboxylic acid.

EXAMPLE 36

Synthesis of Dihydro-6-carboxy-6-phosphono-1-(2-thioethyl)-1-pyrindinium Chloride

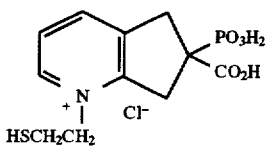

A solution of 3.0 g of dihydro-1-(2-acetylthioethyl)-6-carboxy-6-phosphono-1-pyrindinium bromide (Example 35) in water is passed through a column of anion exchange resin in chloride form. The eluate is concentrated to about 10 ml, and an equal volume of 12 N HCl is added. The solution is placed under a nitrogen atmosphere, and is heated at reflux for 12 hours. The solution is concentrated to dryness, and the residue is recrystallized from water/ethanol (minimizing exposure to air with a nitrogen atmosphere) to yield dihydro-6-carboxy-6-phosphono-1-(2-thioethyl)-1-pyrindinium chloride.

EXAMPLE 37

Synthesis of Octahydro-6-phosphono-1-pyrindine-6-carboxylic Acid

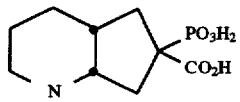

1.0 g of dihydro-6-phosphono-1-pyrindine-6-carboxylic acid hydrochloride (Example 31) in 50 ml of $H_2O$ with 0.5 g of $PtO_2$ is hydrogenated on a Parr apparatus at 40 PSI and 50° for 3 days. The catalyst is filtered off, and the filtrate is taken to dryness under vacuum. The resulting solid is taken up in the minimum amount of water, and precipitated by slow addition of ethanol to give octahydro-6-phosphono-1-pyrindine-6-carboxylic acid.

EXAMPLE 38

Synthesis of Octahydro-1-methyl-6-phosphono-1-pyrindine-6-carboxylic Acid

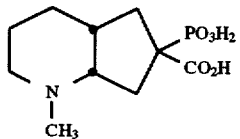

A suspension of 2.0 g of dihydro-6-carboxy-1-methyl-6-phosphono-1-pyrindinium iodide (Example 32) and 1.0 g of $PtO_2$ in 50 ml of water is hydrogenated at 40 PSI and 50° for 2 days on a Parr apparatus. After the catalyst is removed by filtration, the filtrate is evaporated to dryness. The residue is recrystallized from water/acetone to yield octahydro-1-methyl-6-phosphono-1-pyrindine-6-carboxylic acid.

EXAMPLE 39

Synthesis of Octahydro-6-carboxy-1,1-dimethyl-6-phosphono-1-pyrindinium Iodide

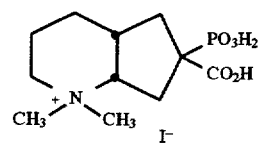

This compound is made by the method of Example 2, starting with octahydro-1-methyl-6-phosphono-1-pyrindine-6-carboxylic acid.

EXAMPLE 40

Synthesis of Octahydro-6-carboxy-1-methyl-6-phosphono-1-phenylmethyl-1-pyrindinium Bromide

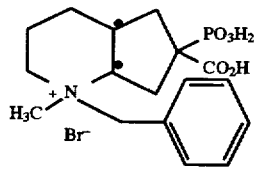

This compound is made by the method of Example 4, starting with octahydro-1-methyl-6-phosphono-1-pyrindine-6-carboxylic acid.

EXAMPLE 41

Synthesis of Octahydro-1-(2-(acetylthio)ethyl)-6-carboxy-1-methyl-6-phosphono-pyrindinium Bromide

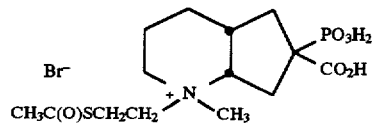

This compound is made by the method of Example 5, starting with octahydro-1-methyl-6-phosphono-1-pyrindine-6-carboxylic acid.

EXAMPLE 42

Synthesis of Octahydro-6-carboxy-1-methyl-6-phosphono-1-(2-thioethyl)pyrindinium Chloride

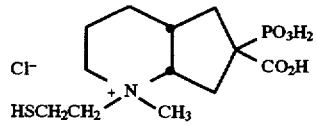

This compound is made by the method of Example 36, starting with octahydro-1-(2-(acetylthio)ethyl)-6-carboxy-1-methyl-6-phosphono-pyrindinium bromide.

EXAMPLE 43

Synthesis of 2-Phosphono-2-(2-pyridinylthio)acetic Acid

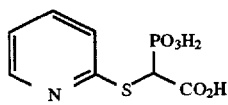

I. Synthesis of Ethyl 2-(Diethoxyphosphinyl)-2-(2-pyridinylthio)acetate.

A suspension of 0.24 g (0.01 mole) of sodium hydride in 50 ml of anhydrous toluene is stirred in an ice bath under a dry nitrogen atmosphere. To this is added dropwise 2.24 g (0.01 mole) of triethyl phosphonoacetate over 15 minutes. The reaction is removed from the ice bath and is stirred at room temperature for 1 hour. It is again cooled in ice, and to it is added rapidly a solution of 2,2'-dipyridyl disulfide (2.20 g; 0.01 mole) in 30 ml of toluene. The reaction is stirred at Oo for 1 hour, and then a second portion of NaH (0.24 g; 0.01 mole) is added. The reaction is allowed to warm to room temperature, and is stirred for another 18 hours. It is filtered, and the filtrate is evaporated under vacuum to yield an oil which is purified by flash-chromatography on silica gel to give the triester.

II. Synthesis of 2-Phosphono-2-(2-pyridinylthio)acetic Acid.

The above triester (2.0 g) in 25 ml of 6 N HCl is heated at reflux for 12 hours. The solution is taken to dryness under vacuum on a rotary evaporator. The residue is redissolved in water and again evaporated to dryness to complete the removal of HCl. The residue is then taken up in water and reprecipitated by slow addition of ethanol, yielding 2-phosphono-2-(2-pyridinylthio)acetic acid.

EXAMPLE 44

Synthesis of 2-Hydroxy-2-phosphono-4-(2-pyridylamino)butanoic Acid

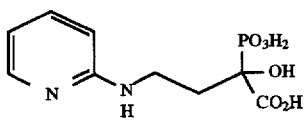

I. Synthesis of Ethyl 2-Oxo-4-(2-pyridylamino)butanoate

A solution of 9.4 g (0.10 mole) of 2-aminopyridine and 12.8 g (0.10 mole) of ethyl 2-oxo-3-butenoate (Example 1) in 50 ml of anhydrous tetrahydrofuran is stirred at 30°–60° for one day. The solvent is removed under vacuum, and the resulting crude product is purified by flash chromatography on silica gel.

II. Synthesis of Ethyl 2-Diethoxyphosphinyl-2-hydroxy-4-(2-pyridylamino)butanoate A mixture of 3.36 g (0.01 mole) of ethyl 2-oxo-4-(2-pyridylamino)butanoate in 6.9 g (0.05 mole) of diethyl phosphite is stirred at 20°–30° for 4 days. The excess diethyl phosphite is removed under vacuum on a rotary evaporator, and the crude product is purified by flash chromatography on silica gel using chloroform/ethanol as eluant.

III. Synthesis of 2-Hydroxy-2-phosphono-4-(2-pyridylamino)butanoic Acid

The above triester is hydrolyzed by refluxing it in 6 N HCl for one day. The aqueous HCl is removed under vacuum, and the residue is dissolved in water, treated with activated charcoal, and filtered. The filtrate is again evaporated dry. The residue is dissolved in a few ml of water, and ethanol is added to precipitate the product. This is further recrystallized from water/ethanol to give 2-hydroxy-2-phosphono-4-(2-pyridylamino)butanoic acid.

EXAMPLE 45

Synthesis of 2-Hydroxy-2-phosphono-4-((2-piperidinylidene)amino)butanoic Acid

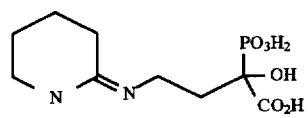

A mixture of 2-Hydroxy-2-phosphono-4-(2-pyridylamino)butanoic acid (1.5 g), 100 ml of distilled water, and 0.5 g of palladium on carbon catalyst is hydrogenated at 40 PSI on a Parr apparatus for 2 days. The catalyst is removed by filtration, and the filtrate is evaporated to dryness under vacuum. The resulting crude product is purified by recrystallization from water/ethanol to yield 2-hydroxy-2-phosphono-4-((2-piperidinylidene)amino) butanoic acid.

EXAMPLE 46

Synthesis of 2-Hydroxy-2-phosphono-4-(3-pyridylamino)butanoic Acid

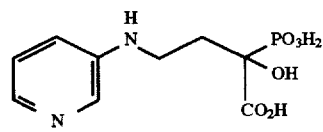

I. Synthesis of Ethyl 2-Oxo-4-(3-pyridylamino)butanoate

A solution of 9.4 g (0.10 mole) of 3-aminopyridine and 12.8 g (0.10 mole) of ethyl 2-oxo-3-butenoate (from Example 1) in 50 ml of anhydrous tetrahydrofuran is stirred at 30°–50° for one day. The solvent is removed under vacuum, and the resulting crude product is purified by flash chromatography on silica gel.

II. Synthesis of Ethyl 2-Diethoxyphosphinyl-2-hydroxy-4-(3-pyridylamino)butanoate A mixture of 3.36 g (0.01 mole) of ethyl 2-oxo-4-(3-pyridylamino)butanoate in 6.9 g (0.05 mole) of diethyl phosphite is stirred at 20°–30° for 4 days. The excess diethyl phosphite is removed under vacuum on a rotary evaporator, and the crude product is purified by flash chromatography on silica gel using chloroform/ethanol as eluant.

III. Synthesis of 2-Hydroxy-2-phosphono-4-(3-pyridylamino)butanoic Acid

The above triester is hydrolyzed by refluxing it in 6 N HCl for one day. The aqueous HCl is removed under vacuum, and the residue is dissolved in water, treated with activated charcoal, and filtered. The filtrate is again evaporated dry. The residue is redissolved in a few ml of water, and ethanol is added to precipitate the product. This is further recrystallized from water/ethanol to give 2-hydroxy-2-phosphono-4-(3-pyridylamino)butanoic acid.

EXAMPLE 47

Synthesis of 2-Hydroxy-2-phosphono-3-(3-piperidylamino)butanoic Acid

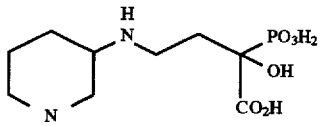

A mixture of 1 g of 2-hydroxy-2-phosphono-4-(3-pyridylamino)butanoic acid and 0.5 g of 10% Pd/C catalyst in 50 ml of distilled $H_2O$ is subjected to hydrogenation on a Parr apparatus at 40 PSI for 2 days. The catalyst is removed by filtration, and the filtrate is concentrated to a few mls. Ethanol is added slowly to effect precipitation of the product, which is purified further by recrystallization from water/ethanol.

EXAMPLE 48

Synthesis of 4-(2-(N,N-Dimethylamino)ethylamino)-2-Hydroxy-2-phosphonobutanoic Acid

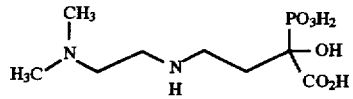

I. Synthesis of Ethyl 4-(2-(N,N-Dimethylamino)ethylamino)-2-Oxo-butanoate

A solution of 8.8 g (0.10 mole) of 2-(N,N-dimethylamino)ethylamine and 12.8 g (0.10 mole) of ethyl 2-oxo-3-butenoate (see Example 1) in 50 ml of anhydrous tetrahydrofuran is stirred at ambient temperature for one day. The solvent is removed under vacuum, and the resulting crude product is purified by flash chromatography on silica gel.

II. Synthesis of Ethyl 2-Diethoxyphosphinyl-4-(2-(N,N-dimethylamino)ethylamino)-2-hydroxybutanoate A mixture of 2.15g (0.01 mole) of ethyl 4-(2-(N,N-dimethylamino)ethylamino)-2-oxobutanoate in 6.9 g (0.05 mole) of diethyl phosphite is stirred at 20°–30° for 4 days. The excess diethyl phosphite is removed under vacuum on a rotary evaporator, and the crude product is purified by flash chromatography on silica gel using chloroform/ethanol as eluant.

III. Synthesis of 4-(2-(N,N-Dimethylamino)ethylanino)-2-Hydroxy-2-phosphonobutanoic Acid The above triester is hydrolyzed by refluxing it in 6 N HCl for one day. The aqueous HCl is removed under vacuum, and the residue is dissolved in water, treated with activated charcoal, and filtered. The filtrate is again evaporated dry. The residue is dissolved in a few ml of water, and ethanol is added to precipitate the product. This is further recrystallized from water/ethanol to give 4-(2-(N,N-dimethylamino)ethylamino)-2-hydroxy-2-phosphonobutanoic acid.

EXAMPLE 49

Synthesis of 4-(2-(N,N-Dimethylamino)ethylthio)-2-Hydroxy-2-phosphono-butanoic Acid

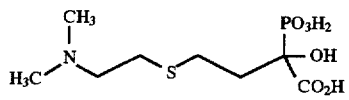

I. Synthesis of Ethyl 4-(2-(N,N-Dimethylamino)ethylthio)-2-oxobutanoate

A solution of 10.5 g (0.10 mole) of 2-(N,N-dimethyl)ethylmercaptan and 12.8 g (0.10 mole) of ethyl 2-oxo-3-butenoate (see Example 1) in 50 ml of anhydrous tetrahydrofuran is stirred at ambient temperature for one day. The solvent is removed under vacuum, and the resulting crude product is purified by flash chromatography on silica gel.

II. Synthesis of Ethyl 2-Diethoxyphosphinyl-4-(2-(N,N-dimethylamino)ethylthio)-2-hydroxybutanoate A mixture of 2.33 g (0.01 mole) of ethyl 4-(2-(N,N-dimethylamino)ethylthio)-2-oxobutanoate in 6.9 g (0.05 mole) of diethyl phosphite was stirred at 20°–30° for 4 days. The excess diethyl phosphite is removed under vacuum on a rotary evaporator, and the crude product is purified by flash chromatography on silica gel using chlorofomi/ethanol as eluant.

III. Synthesis of 4-(2-(N,N-Dimethylamino)ethylthio)-2-hydroxy-2-phosphonobutanoic Acid The above triester is hydrolyzed by refluxing it in 6 N HCl for one day. The aqueous HCl is removed under vacuum, and the residue is dissolved in water, treated with activated charcoal, and filtered. The filtrate is again evaporated dry. The residue is redissolved in a few ml of water, and ethanol is added to precipitate the product. This is further recrystallized from water/ethanol to give 4-(2-(N,N-dimethylamino)ethylthio)-2-hydroxy- 2-phosphonobutanoic acid.

EXAMPLE 50

Synthesis of 2-Hydroxy-3-(imidazo[1,2-a]pyridin-3-yl)-2-phosphonopropanoic Acid

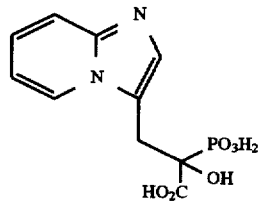

I. Synthesis of 3-(Imidazo[1,2-a]pyridine)carboxaldehyde

A solution of 1.75 g (0.01 mole) of 3-(N,N-dimethylaminomethyl)imidazo[1,2-a]pyridine (prepared as by Lombardino, *J. Org. Chem.* 30, 2403 (1965)) and 1.40 g (0.01 mole) of hexamethylenetetramine in 15 ml of 66% propanoic acid is added dropwise over 2–3 hours to a refluxing solution of 1.4 g of hexamethylenetetramine in 10 ml 66% propanoic acid. The reaction is heated at reflux a further 2 hours, and is then cooled to room temperature. Water is added, causing 3-(imidazo[1,2-a]pyridine) carboxaldehyde to precipitate.

II. Synthesis of Ethyl 2-Oxo-3-(imidazo[1,2-a]pyridin-3-yl)propanoate

To a stirred, ice-cooled suspension of 3.6 g (0.15 mole) of NaH in about 100 ml of anhydrous ether is added a mixture of 12.85 g (0.088 mole) of 3-(imidazo[1,2-a]pyridine) carboxaldehyde and 23.4 g (0.178 mole) of N,N-dimethylglycine ethyl ester in 50 ml of ether. This is added over about one hour. The reaction mixture is stirred for about 18 hours, while it warms to room temperature during that time. It is then cooled in ice, and about 50 ml of saturated aqueous NH₄Cl is added. The layers are separated, and the water layer is extracted with ether. The combined organic layers are dried and distilled under high vacuum to give ethyl 2-(N,N-dimethylamino)-3-(imidazo[1,2-a]pyridine) propenoate. This is taken up in a mixture of ether (20 ml) and 1 N HCl (20 ml) and stirred rapidly. To this is added conc. HCl until the pH is 1 or less. The mixture is stirred 10 min. longer, and the ether layer is removed (discarded). The water is extracted further with ether until nothing more ends up in the ether. The water is then brought to about pH 7 with solid NaHCO₃. A solid precipitates, which is collected by filtration, washed with water, and dried to yield ethyl 2-oxo-3-(imidazo[1,2-a]pyridin-3-yl)propanoate.

III. Synthesis of Ethyl 2-Dimethoxyphosphinyl-2-hydroxy-3-(imidazo[1,2-a]pyridin-3-yl)propanoate A suspension of ethyl 2-oxo-3-(imidazo[1,2-a]pyridin-3-yl)propanoate (2.32 g; 0.01 mole) in 5.5 g (0.05 mole) of dimethylphosphite is stirred at ambient temperature for 3 days. The excess dimethylphosphite is removed under high vacuum on a rotary evaporator at a bath temperature of about 55° to give the crude product. This is purified by flash chromatography on silica gel to afford ethyl 2-dimethoxyphosphinyl-2-hydroxy-3-(imidazo[1,2-a]pyridin-3-yl)propanoate.

IV. Synthesis of 2-Hydroxy-3-(imidazo[0.2-a]pyridin-3-yl)-2-phosphonopropanoic Acid The above ester (1.5 g) is hydrolyzed by dissolving it in 20 ml of 12 N HCl and heating the solution at reflux for 6 hours. The solution is taken to dryness on a rotary evaporator. Distilled water (20 ml) is added, and the solution is again evaporated dry. The residue is recrystallized from the minimum required amount of hot water, providing 2-hydroxy-3-(imidazo[1,2-a]pyridin-3-yl)-2-phosphonopropanoic acid.

EXAMPLE 51

Synthesis of 2-Hydroxy-2-phosphono-3-(2-pyridinyl)propanoic Acid

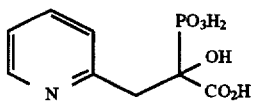

I. Synthesis of Ethyl 2-Dimethoxyphosphinyl-2-hydroxy-3-(2-pyridyl)propanoate

A suspension of 11.64 g (0.060 mole) of ethyl 2-oxo-3-(2-pyridinyl)propanoate (synthesized from pyridine 2-carboxaldehyde by chemistry analogous to that for pyridine 3-carboxaldehyde in Liebig's Annalen der Chemie, 703 37–43 (1967)) in 30.13 g (0.274 mole) of dimethylphosphite is stirred at 20°–30° for 3 days. The excess dimethylphosphite is removed on a rotary evaporator under high vacuum at a bath temperature of about 55° to afford crude product. This is purified by flash chromatography on silica gel using chloroform/methanol (20/1) as eluant.

II. Synthesis of 2-Hydroxy-2-phosphono-3-(2-pyridyl)propanoic Acid

About 6 g of the above ester is dissolved in 50 ml of 12 N HCl, and the solution is heated at reflux for 5 hours. The solution is concentrated on a rotary evaporator to yield a viscous oil. This is dissolved in about 5 ml water, and the flask is scratched with a glass rod causing a solid to form. The solid is collected by filtration and washed with a few ml water. This is dried in a desiccator to yield 2-hydroxy-2-phosphono-3-(2-pyridyl)propanoic acid.

EXAMPLE 52

Synthesis of 2-(2-Carboxy-2-hydroxy-2-phosphonoethyl)-1-methylpyridinium Chloride

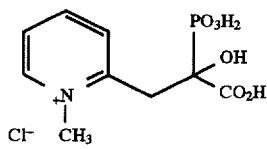

This compound is prepared according to the method given in Example 24, starting with ethyl 2-dimethoxyphosphinyl-2-hydroxy-3-(2-pyridinyl)propanoate (from Example 51).

EXAMPLE 53

Synthesis of 2-(2-Carboxy-2-hydroxy-2-phosphonoethyl)-1-ethylpyridinium Chloride

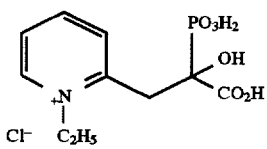

This compound is prepared according to the method given in Example 25, starting with ethyl 2-dimethoxyphosphinyl-2-hydroxy-3-( 2-pyridinyl)propanoate (from Example 51).

EXAMPLE 54

Synthesis of 2-(2-Carboxy-2-hydroxy-2-phosphonoethyl)-1-(2-thioethyl)pyridinium Chloride

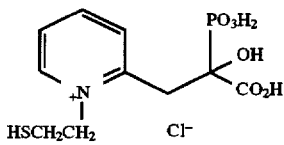

This compound is prepared according to the method given in Example 26, starting with ethyl 2-dimethoxyphosphinyl-2-hydroxy-3-(2-pyridinyl)propanoate (from Example 51).

EXAMPLE 55

Synthesis of 2-Hydroxy-3-(1-methyl-2-piperidinyl)-2-phosphonopropanoic Acid

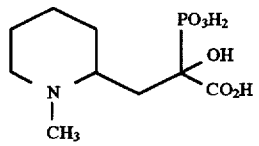

A mixture of 1 g of 1-methyl-2-(2-carboxy-2-hydroxy-2-phosphonoethyl)pyridinium iodide and 0.5 g of palladium on charcoal catalyst in 50 ml of distilled water is hydrogenated on a Parr apparatus at 40 PSI for about 2 days. The catalyst is removed by filtration, and the filtrate is evaporated to dryness. The residue is triturated with ethanol to give a solid which is collected by filtration. It is recrystallized from water/ethanol to afford 2-hydroxy-3-(1-methyl-2-piperidinyl)-2-phosphonopropanoic acid.

EXAMPLE 56

Synthesis of N,N-Dimethyl-2-(2-carboxy-2-hydroxy-2-phosphonoethyl)piperidinium Iodide

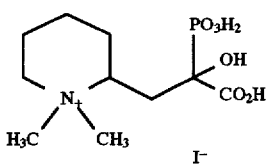

This is prepared by the method used in Example 2, starting with 2-hydroxy-3-(1-methyl-2-piperidinyl)-2-phosphonopropanoic acid.

EXAMPLE 57

Synthesis of N-Ethyl-N-methyl-2-(2-carboxy-2-hydroxy-2-phosphonoethyl)piperidinium Iodide

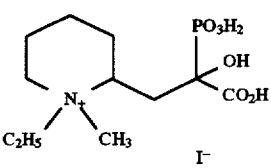

This is prepared by the method used in Example 3, starting with 2-hydroxy-3-(1-methyl-2-piperidinyl)-2-phosphonopropanoic acid.

EXAMPLE 58

Synthesis of N-[2-(Acetylthio)ethyl]-N-methyl-2-(2-carboxy-2-hydroxy-2-phosphonoethyl)piperidinium Bromide

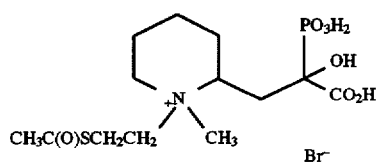

This is prepared by the method used in Example 5, starting with 2-hydroxy-3-(1-methyl-2-piperidinyl)-2-phosphonopropanoic acid.

EXAMPLE 59

Synthesis of N-Methyl-N-(2-thioethyl)-2-(2-carboxy-2-hydroxy-2-phosphonoethyl)piperidinium Chloride

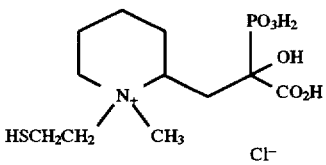

This is prepared by the method used in Example 6, starting with N-[2-(acetylthio)ethyl]-N-methyl-2-(2-carboxy-2-hydroxy-2-phosphonoethyl)piperidinium bromide.

EXAMPLE 60

Synthesis of 2-Hydroxy-3-(2-piperidinyl)-2-phosphonopropanoic Acid

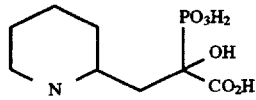

A mixture of 1 g of 2-hydroxy-2-phosphono-3-(2-pyridinyl)propanoic acid and 0.5 g of palladium on charcoal catalyst in 50 ml of distilled water is hydrogenated on a Parr apparatus at 40 PSI for about 2 days. The catalyst is removed by filtration, and the filtrate is concentrated to a few mls. Ethanol is added slowly to precipitate a solid, which is recrystallized from water/ethanol to afford 2-hydroxy-3-(2-piperidinyl)-2-phosphonopropanoic acid.

EXAMPLE 61

Synthesis of 2-Hydroxy-3-(3-piperidinyl)-2-phosphonopropanoic Acid

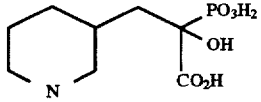

This compound is prepared by the method of Example 60, starting with 2-hydroxy-2-phosphono-3-(3-pyridinyl)propanoic acid.

EXAMPLE 62

Synthesis of 2-Hydroxy-3-(1-methyl-3-piperidinyl)-2-phosphonopropanoic Acid

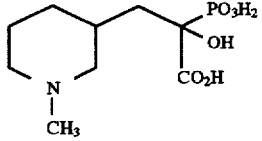

This compound is prepared by the method of Example 55, starting with 3-(2-carboxy-2-hydroxy-2-phosphonoethyl)-1-methylpyridinium chloride.

EXAMPLE 63

Synthesis of N,N-Dimethyl-3-(2-carboxy-2-hydroxy-2-phosphonoethyl)piperidinium Iodide

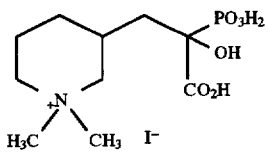

This is prepared by the method used in Example 2, starting with 2-hydroxy-3-(1-methyl-3-piperidinyl)-2-phosphonopropanoic acid.

EXAMPLE 64

Synthesis of N-(2-(Acetylthio)ethyl)-N-methyl-3-(2-carboxy-2-hydroxy-2-phosphonoethy)piperidinium Bromide

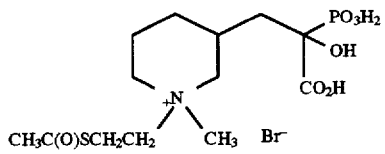

This is prepared by the method used in Example 5, starting with 2-hydroxy-3-(1-methyl-3-piperidinyl)-2-phosphonopropanoic acid.

EXAMPLE 65

Synthesis of N-Methyl-N-(2-thioethyl)-2-(2-carboxy-2-hydroxy-2-phosphonoethyl)piperidinium Chloride

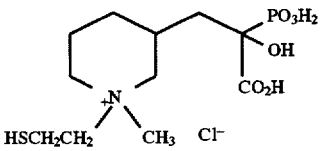

This is prepared by the method used in Example 6, starting with N-(2-(acetylthio)ethyl)-N-methyl-3-(2-carboxy-2-hydroxy-2-phosphonoethyl)piperidinium bromide.

EXAMPLE 66

Capsules are prepared having the following composition:

| Active Ingredient | Mg Per Capsule |
|---|---|
| 2-hydroxy-2-phosphono-3-(pyridyl)propanoic Acid | 350.0 |
| Excipients | |
| Lactose | 90.0 |
| Microcrystalline Cellulose | 60.0 |
| Magnesium Stearate | 1.0 |

The capsules having the above composition are prepared using conventional methods as described below:

The active ingredient is mixed with the microcrystalline cellulose in a turn shell blender for approximately ten (10) minutes.

The resulting mixture is passed through a hammer mill with an 80 mesh screen.

The mixture is put back into the twin shell blender along with the lactose and is then mixed for approximately fifteen (15) minutes.

The magnesium stearate is next added and blended for an additional five (5) minutes. The resulting blend is then compressed on a piston-activated capsule filler.

Any of the compounds prepared according to Examples 1 to 65 may be substituted for the active ingredient in the capsule prepared hereinabove.

EXAMPLE 67

Tablets are prepared having the following composition:

| Active Ingredient | Mg Per Tablet |
|---|---|
| 3-(2-carboxy-2-hydroxy-2 phosphonoethyl)-1-(2-thioethyl)-pyridinium chloride | 700.00 |
| Excipients | |
| Lactose (spray-dried) | 200.0 |
| Starch (1500) | 100.0 |
| Magnesium Stearate | 25.0 |

Tablets are prepared having the above composition using conventional methods as described below:

The active ingredient is ground in a ball mill for, approximately thirty (30) minutes. The milled active ingredient is then blended in a twinblade mixer with the spray-dried lactose for approximately twenty (20) minutes.

The starch is added to the mixture and is then mixed for an additional fifteen (15) minutes. The blend is compressed into tablets on a standard tablet press.

Any of the compounds prepared according to Examples 1 to 65 may be substituted for the active ingredient in the tablet prepared hereinabove.

EXAMPLE 68

Injectable solutions are prepared by conventional methods using 10.0 ml of physiological saline solution and 7.0 mg P of Example 30, adjusted to pH=7.4.

One injection, one time daily for 4 days, results in appreciable alleviation of hypercalcemia of malignancy in patients weighing approximately 70 kilograms.

Any of the compounds prepared according to Examples 1 to 65 may be substituted for the active ingredient in the injection prepared hereinabove.

EXAMPLE 69

A Caucasian male, weighing approximately 92 kilograms, seventy-two years of age, suffering from moderate to severe pain, and occasional swelling, of the right knee. After approximately one year of steadily increasing discomfort, he visits a physician who renders a clinical diagnosis of osteoarthritis of the right knee, which was subsequently verified by X-ray diagnosis.

After a period of ameliorative therapy of various NSAIDs, including aspirin, naprosen, and ketoprofen, his symptoms continue to worsen and his condition appears to degenerate. He returns to his physician who then prescribes the tablets prepared as described in Example 67 twice daily two hours before or after meals for a period of three months. His clinical symptoms of pain and swelling, particularly with extended walking, improved significantly after his 3 months of therapy. At the conclusion of three months at a dosage of 2 tablets per day, the therapy is continued at one-half the dosage originally prescribed (i.e. 1 tablets per day) indefinitely.

EXAMPLE 70

A black female, weighing approximately 65 kilograms, fifty-five years of age, presents with swelling and deformation of the finger joints of both hands, with partial loss of strength and/or dexterity of her fingers and hands. Upon visual and X-ray examination and various appropriate clinical tests approved by the American Rheumatological Association (ARA) she is diagnosed with rheumatoid arthritis.

After an unsuccessful analgesic and anti-inflammatory therapy, her physician prescribes the tablets prepared in Example 67, two times daily two hours before or after meals for a period of four months. After a month of therapy, her symptoms of knuckle swelling noticeably improves and her range of finger motion increases significantly; she continues therapy for the remainder of the four months, after which her physician continues the prescribed dose for an additional two months.

EXAMPLE 71

A female of Hispanic origin, twelve years of age, weighing approximately 37 kilograms, presents to the physician with idiopathic juvenile rheumatoid arthritis. Her symptoms include marked inflammation of multiple joints, complicated by heat and tenderness and indicating rapid and pathological degeneration of joint function.

Her physician refers her to a rheumatologist who immediately prescribes aggressive therapy by IV administration of the solution prepared as described in Example 68 over a period of three days, at the rate of 1 injection per day, administered over two hours. At the conclusion of the IV regimen, the physician prescribes the tablets prepared as described in Example 67, for a period of two months, during which she exhibits marked improvement with increased mobility and decreased pain. For the succeeding two months, the physician reduces her dose to ¾ of the original oral dose by prescribing 3 tablets over a period of two days, i.e. one 2-tablet day alternating with one 1-tablet day. At the conclusion of this regimen the dosage is again reduced to ¼ of the original dose by giving her the tablets prepared as described in Example 67, 1 tablet every day for an additional four months.

EXAMPLE 72

A 60-year-old Caucasian female weighing 62 kg, experiences severe back pain. Her physician, with the aid of a radiologist diagnoses her as having a crush fracture of the L1 vertebrae presumably due to osteoporotic bone loss. The patient is prescribed a three month, once-daily dosage regimen of a 700 mg tablet prepared accordinging to the procedure described in Example 67. The 700 mg tablet is taken either two hours before or two hours after any given meal. After three months, the dosage is reduced to a 350 mg capsule, prepared as described in Example 66, taken every other day for a period of three months. Her physician then puts her on a maintenance dosing regimen wherein she takes a 100 mg capsule every day for six months. After six months on the maintenance dosing regimen the patient is not experiencing any further back pain. Follow-up x-rays reveal no additional fractures.

EXAMPLE 73

A 75-year-old Oriental female weighing 53 kg suffers a fractured hip after a fall. She is hospitalized and diagnosed as having osteoporosis. A treatment regimen of calcitonin injections is prescribed. The calcitonin injections are painful to the patient and she is unable to comply with the calcitonin regimen. Her physician then switches her therapy to an oral phosphonate regimen. She is administered a 700 mg tablet prepared according to the procedure described in Example 67, twice daily for one month. At the end of this one month of therapy, she is given a 700 mg tablet, once daily for two months. At the end of this two month period, she is given a 100 mg capsule, prepared according to the procedure described in Example 16, daily for three months. A follow-up visit to her physician reveals no apparent decrease in mineral density of the forearm as determined by photonabsorptimetry.

EXAMPLE 74

A 85-year-old Native American male weighing 65 kg presents to his physician with severe back pain. X-rays reveal multiple minor vertebral body collapse resulting from significant bone loss due to osteoporosis. The patient is prescribed a two month regimen of a 700 mg tablet and a 350 mg capsule to be taken on the same day, eight hours apart, prepared according to the procedures described in Examples 67 and 66, respectively. After two months on this regimen, his dosage is reduced to 350 mg tablet once a day for two months. X-rays are taken and an additional crush fracture is noted. He is then put on a maintenance regimen of a 100 mg capsule, prepared according to the procedure described in Example 66, once a day for six months. At the end of this six months, no significant apparent decrease in bone density is observed.

What is claimed is:

1. A pharmaceutical composition comprising pharaceutically-acceptable carriers and a safe and effective amount of a phosphonocarboxylate, or a pharmaceutically-acceptable salts thereof, having a structure according to formula (I):

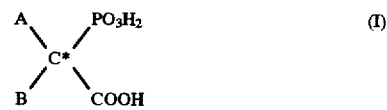

wherein
(A)
(1) A is selected from the group consisting of hydrogen; halogen; $SR^1$; $R^2SR^1$; amino; hydroxy; and substituted or unsubstituted $C_1-C_8$ alkyl;
(2) B is
  (a) $NH_2$;
  (b) a saturated or unsaturated $C_1-C_{15}$ alkyl chain substituted with one or more substituents selected from the group consisting of —$R^3N(R^4)_2$; —$R^3[-N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$;
  (c) a substituted or unsubstituted, saturated or unsaturated heteroalkyl chain having from 2 to 15 chain atoms, where one or more of said chain atoms is nitrogen;
  (d) a substituted or unsubstituted, saturated or unsaturated heteroalkyl chain having from 2 to 15 chain atoms, where one or more of said chain atoms is selected from S and O; and where said heteroalkyl chain is substituted with one or more substituents selected from the group consisting of —$R^3N(R^4)_2$; —$R^3[-N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$; or (e) $R^6$—L— where
  (i) L is selected from the group consisting of nil; N; —$N(R^5)_2^+$; S; O; a substituted or unsubstituted, saturated or unsaturated $C_1$–$C_{15}$ alkyl chain; and a substituted or unsubstituted, saturated or unsaturated heteroalkyl chain having from 2 to 15 chain atoms, where one or more of said chain atoms is N, S, or O; and
  (ii) $R^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein $R^6$ may be substituted with one or more substituents independently selected from the group consisting of hydrogen; —$R^3SR^1$; substituted or unsubstituted $C_1$–$C_8$ alkyl; —$R^3OR^4$; —$R^3CO_2R^4$; —$R^3O_2CR^4$; —$R^3N(R^4)_2$; $R^3$[—$N(R)_3$]$^+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; substituted or unsubstituted aryl; and hydroxy; and (3)
  (a) $R^1$ is independently selected from the group consisting of hydrogen; —$C(O)R^7$; —$C(S)R^7$; —$C(O)N(R^7)_2$; —$C(O)OR^7$; —$C(S)N(R^7)_2$; and —$C(S)OR^7$; where $R^7$ is hydrogen or substituted or unsubstituted $C_1$–$C_8$ alkyl;
  (b) $R^2$ is substituted or unsubstituted $C_1$–$C_8$ alkyl;
  (c) $R^3$ is selected from the group consisting of nil and substituted or unsubstituted $C_1$–$C_8$ alkyl;
  (d) $R^4$ is independently selected from the group consisting of hydrogen; substituted or unsubstituted $C_1$–$C_8$ alkyl; and —$R^2SR^1$; and
  (e) $R^5$ is independently selected from the group consisting of substituted or unsubstituted $C_1$–$C_{15}$ alkyl; substituted or unsubstituted phenyl; benzyl; and —$R^2SR^1$;

or (B) A and B are covalently linked together with C* to form a monocyclic or bicyclic ring having the following structure:

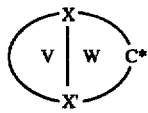

where
  (1) W is a substituted or unsubstituted, saturated or unsaturated carbocyclic ring comprising C*, X and X', said carbocyclic ring having a total of from 3 to 6 ring carbon atoms; or a substituted or unsubstituted, saturated or unsaturated heterocyclic ring comprising C*, X, and X', said heterocyclic ring having a total of from 4 to 6 ring atoms, where one or more of said ring atoms is N, O, or S;
  (2) V is nil; a substituted or unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and
  (3) X and X' are independently N or C;
  except that if neither V nor W is a nitrogen containing heterocycle, then at least one of V or W is substituted with one or more substituents selected from the group consisting of —$R^3N(R^4)_2$; $R^3$[—$N(R^5)_3$]$^+$; —$R^3N(R^4)C(O)R^4$; —$R^3N(R^4)C(S)R^4$; —$R^3N(R^4)C(N)R^4$; and —$R^3C(O)N(R^4)_2$.

2. A composition according to claim 1, wherein A is hydroxy; and wherein B is a substituted or unsubstituted, saturated or unsaturated heteroalkyl chain having from 2 to 15 chain atoms, where one or more of said chain atoms is nitrogen, or B is $R^6$—L—.

3. A composition according to claim 2 wherein B is $R^6$—L—.

4. A composition according to claim 3, wherein L is nil, N, $N(R^5)_2^+$, a $C_1$–$C_{15}$ alkyl chain, or a nitrogen containing heteroalkyl chain having from 2 to 15 chain atoms.

5. A composition according to claim 4, wherein L is a $C_1$–$C_{15}$ alkyl chain.

6. A composition according to claim 5, wherein said alkyl chain is substituted with one or more substituents selected from the group consisting of —$R^3SR^1$; hydrogen; substituted or unsubstituted $C_1$–$C_8$ alkyl; —$R^3OR^4$; and —$R^3CO_2R^4$.

7. A composition according to claim 4, wherein L is a nitrogen containing heteroalkyl chain.

8. A composition according to claim 7, wherein said heteroalkyl chain is substituted with one or more substituents selected from the group consisting of —$R^3SR^1$; hydrogen; —$R^3N(R^4)_2$; —$R^3[N(R^5)_3]^+$; and —$R^3N(R^4)C(O)R^4$.

9. A composition according to claim 3, wherein $R^6$ is a monocyclic heterocyclic moiety.

10. A composition according to claim 9, wherein $R^6$ is a six-membered heterocyclic ring moiety selected from the group consisting of pyridine, pyrimidine, piperidine, pyridinium, pyrimidinium, and piperidinium; or $R^6$ is a five-membered heterocyclic ring moiety selected from the group consisting of imidazol, pyrrole, pyrrolidine, imidazolium, pyrrolium, and pyrrolidinium.

11. A composition according to claim 3, wherein $R^6$ is a polycyclic heterocyclic moiety.

12. A composition according to claim 11, wherein $R^6$ is a six-membered ring fused to a five-membered ring selected from the group consisting of indol, indolium, pyrindine, imidazol-(1,2-a-)pyridine, imidazol-(1,2-a-)pyridinium, and pyrindinium; or a six-membered ring fused to a six-membered ring, where said polycyclic heterocycle is selected from the group consisting of quinoline, isoquinoline, tetrahydroquinoline, octahyrdroquinoline, quinolinium, isoquinolinium, tetrahydroquinolinium, and octahydroquinolinium.

13. A composition according to claim 3, wherein $R^6$ is a monocyclic carbocyclic moiety.

14. A composition according to claim 13, wherein $R^6$ is cycloheptyl or cyclohexyl.

15. A composition according to claim 3, wherein $R^6$ is substituted with one or more substituents selected from the group consisting of hydrogen; —$R^3SR^1$; —$R^3N(R^4)_2$; $R^3$[—$N(R^5)_3$]$^+$; and —$R^3N(R^4)C(O)R^4$.

16. A composition according to claim 2, wherein B is a heteroalkyl chain, where one or more chain atoms is nitrogen.

17. A composition according to claim 16, wherein said heteroalkyl chain is substituted with one or more substituents selected from the group consisting of —$R^3$ $SR^1$; hydrogen; substituted or unsubstituted $C_1$–$C_8$ alkyl; —$R^3OR^4$; —$R^3CO_2R^4$; —$R^3N(R^4)_2$; —$R^3[N(R^5)_3]^+$; and —$R^3N(R^4)C(O)R^4$.

18. A composition according to claim 2, wherein $R^4$ is hydrogen.

19. A composition according to claim 2, wherein $R^1$ is hydrogen; $—C(O)R^7$; $C(S)R^7$; or $C(O)N(R^7)_2$.

20. A composition according to claim 1, wherein A and B, together with $C^*$, form a bicyclic ring, where both and X and X' are carbon atoms.

21. A composition according to claim 20, wherein W is a five-membered carbocyclic ring comprising $C^*$, X and X'.

22. A composition according to claim 21, wherein V is a five-membered ring or a six-membered ring.

23. A composition according to claim 22, wherein V is a heterocycle containing at least one ring nitrogen atom.

24. A composition according to claim 20, wherein said bicyclic ring is substituted with one or more substituents selected from the group consisting of $—R^3SR^1$; hydrogen; substituted or unsubstituted $C_1-C_8$ alkyl; $—R^3OR^4$; $—R^3CO_2R^4$; $—R^3O_2CR^4$; $—R^3N(R^4)_2$; $—R^3[N(R^5)_3]^+$; $—R^3N(R^4)C(O)R^4$; $—R^3N(R^4)C(S)R^4$; $—R^3N(R^4)C(N)R^4$; and $—R^3C(O)N(R^4)_2$.

25. A composition according to claim 24, wherein said bicyclic ring is substituted with one or more of $—R^3SR^1$; hydrogen; $—R^3N(R^4)_2$; $—R^3CO_2R^4$; $—R^3[N(R^5)_3]^+$; or $—R^3N(R^4)C(O)R^4$; and $R^4$ is $R^3SR^1$ or hydrogen.

26. A composition according to claim 25, wherein $R^1$ is hydrogen; $—C(O)R^7$; $—C(S)R^7$; or $—C(O)N(R^7)_2$.

27. A pharmaceutical composition comprising pharmaceutically-acceptable carriers and a safe and effective amount of a phosphonocarboxylate, or a pharmaceutically-acceptable salts thereof, having a structure according to formula (II):

wherein
(A)
(1) A is hydroxy; and
(2) B is

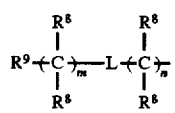

wherein
(a) m is an integer from 0 to 10; n is an integer from 0 to 10; and m+n is an integer from 0 to 10;
(b) $R^8$ is independently selected from the group consisting of nil; $—R^3SR^1$; hydrogen; substituted or unsubstituted $C_1-C_8$ alkyl; $—R^3OR^4$; $—R^3CO_2R^4$; $—R^3O_2CR^4$; $—R^3N(R^4)_2$; $—R^3[N(R^5)_3]^+$; $—R^3N(R^4)C(O)R^4$; $—R^3N(R^4)C(S)R^4$; $—R^3N(R^4)C(N)R^4$; $—R^3C(O)N(R^4)_2$; halogen; $—R^3C(O)R^4$; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings;
(c) $R^1$ is independently selected from the group consisting of hydrogen; $—C(O)R^7$; $—C(S)R^7$; $—C(O)N(R^7)_2$; $—C(O)OR^7$; $—C(S)N(R^7)_2$; and $—C(S)OR^7$; where $R^7$ is hydrogen or substituted or unsubstituted $C_1-C_8$ alkyl;

(d) $R^3$ is selected from the group consisting of nil and substituted or unsubstituted $C_1-C_8$ alkyl;
(e) $R^4$ is independently selected from the group consisting of hydrogen; substituted or unsubstituted $C_1-C_8$ alkyl; and $—R^2SR^1$;
(f) $R^5$ is independently selected from the group consisting of substituted or unsubstituted $C_1-C_{15}$ alkyl; substituted or unsubstituted phenyl; benzyl; and $—R^2SR^1$;
(g) L is selected from the group consisting of nil; $—N(R^8)—$; $[—N(R^5)_2—]^+$; $—S—$; $—O—$; and $—D—C(=E)—S—$, where D is selected from the group consisting of covalent bond, O, or S, and E is O or S; and wherein
  (i) when L is $—N(R^8)—$, or when L is $[—N(R^5)_2—]^+$ and m is an integer from 1 to 10, $R^9$ is independently selected from the group consisting of nil; hydrogen; substituted or unsubstituted $C_1-C_{35}$ alkyl; $R^2SR^1$; and $R^{10}$;
  (ii) when L is $[—N(R^5)_2—]^+$ and m=0, $R^9$ is selected from the group consisting of substituted or unsubstituted $C_1-C_{35}$ alkyl; $R^2SR^1$; and $R^{10}$; or
  (iii) when L is nil, $—S—$, $—O—$, or $—D—C(=E)—S$, $R^9$ is $R^{10}$;
(h) $R^{10}$ is a saturated, unsaturated, or aromatic monocyclic or polycylic carbocycle, or a saturated, unsaturated, or aromatic monocyclic or polycylic heterocycle containing one or more heteroatoms; where said carbocycle or heterocycle is substituted with one or more $R^{11}$ substituents; and
(i) each $R^{11}$ is independently selected from the group consisting of $—R^3SR^1$; hydrogen; substituted or unsubstituted $C_1-C_8$ alkyl; $—R^3OR^4$; $—R^3CO_2R^4$; $—R^3O_2CR^4$; $—R^3N(R^4)_2$; $—R^3[—N(R^5)_3]^+$; $—R^3N(R^4)C(O)R^4$; $—R^3N(R^4)C(S)R^4$; $—R^3N(R^4)C(N)R^4$; $—R^3C(O)N(R^4)_2$; halogen; $—R^3C(O)R^4$; hydroxy; substituted or unsubstituted arylalkyl; nitro; and unsubstituted or substituted aryl;

or
(B) A and B are covalently linked together with $C^*$ to form a monocyclic or bicyclic ring having the following structure:

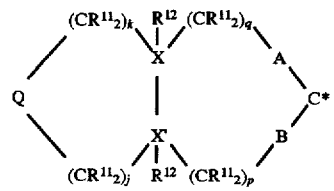

wherein
(a) A and B are independently selected from the group consisting of nil, $—O—$, $—S—$, and $—NR^{12}—$;
(b) Q is selected from the group consisting of nil; $—NR^{12}—$; and $[—N(R^{13})_2—]^+$;
(c) X and X' are independently selected from C or N;
(d) $R^{12}$ is independently selected from the group consisting of nil; $—R^3SR^1$; hydrogen; substituted or unsubstituted $C_1-C_8$ alkyl; $—R^3OR^4$; $—R^3CO_2R^4$; $—R^3O_2CR^4$; $—R^3N(R^4)_2$; $R^3[—N(R^5)_3]^+$; $—R^3N(R^4)C(O)R^4$; $—R^3C(O)N(R^4)_2$; halogen; $—R^3C(O)R^4$; hydroxy; substituted or unsubstituted arylalkyl; nitro; and unsubstituted or substituted aryl;
(e) $R^{13}$ is selected from the group consisting of nil; substituted or unsubstituted $C_1-C_{35}$ alkyl; substituted or unsubstituted phenyl; benzyl; and $—R^2SR^1$;

(f) when Q is other than nil, k and j and k+j are integers from 0 to 5; when Q is nil, k and j and k+j are integers from 0 to 6; and (g) p and q and p+q are independently integers from 0 to 3; except that if Q is nil, then at least one of $R^{11}$ or $R^{12}$ is selected from the group consisting of —$R^3N(R^4)_2$; $R^3[-N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$.

28. A method for treating or preventing pathological conditions associated with abnormal calcium and phosphate metabolism in humans or other mammals in need of such treatment, comprising administering to a human or other mammal a safe and effective amount of a phosphonocarboxylate containing composition of claim 1.

29. A method for treating or preventing pathological conditions associated with abnormal calcium and phosphate metabolism in humans or other mammals in need of such treatment, comprising administering to a human or other mammal a safe and effective amount of a phosphonocarboxylate containing composition of claim 2.

30. A method for treating or preventing pathological conditions associated with abnormal calcium and phosphate metabolism in humans or other mammals in need of such treatment, comprising administering to a human or other mammal a safe and effective amount of a phosphonocarboxylate containing composition of claim 20.

31. A method for treating or preventing pathological conditions associated with abnormal calcium and phosphate metabolism in humans or other mammals in need of such treatment, comprising administering to a human or other mammal a safe and effective amount of a phosphonocarboxylate containing composition of claim 27.

32. Phosphonocarboxylates and the pharmaceutically-acceptable salts thereof, having a structure according to formula (I):

wherein
(A)
(1) B is
(a) —$NH_2$;
(b) a saturated or unsaturated $C_1$–$C_{15}$ alkyl chain substituted with one or more substituents selected from the group consisting of —$R^3N(R^4)_2$; $R^3[-N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$;
(c) a substituted or unsubstituted, saturated or unsaturated heteroalkyl chain having from 2 to 15 chain atoms, where one or more of said chain atoms is nitrogen;
(d) a substituted or unsubstituted, saturated or unsaturated heteroalkyl chain having from 2 to 15 chain atoms, where one or more of said chain atoms is selected from S and O; and where said heteroalkyl chain is substituted with one or more substituents selected from the group consisting of —$R^3N(R^4)_2$; —$R^3[-N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$; or
(e) $R^6$—L— where
(i) L is selected from the group consisting of nil; N; —$N(R^5)_2^+$; S; O; a substituted or unsubstituted, saturated or unsaturated $C_1$–$C_{15}$ alkyl chain; and a substituted or unsubstituted, saturated or unsaturated heteroalkyl chain having from 2 to 15 chain atoms, where one or more of said chain atoms is N, S, or O; and (ii) $R^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein $R^6$ may be substituted with one or more substituents independently selected from the group consisting of hydrogen; —$R^3SR^1$; substituted or unsubstituted $C_1$–$C_8$ alkyl; —$R^3OR^4$; —$R^3CO_2R^4$; —$R^3O_2CR^4$; —$R^3N(R^4)_2$; $R^3[-N(R^5)_3]^+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; substituted or unsubstituted aryl; and hydroxy; and (2)
(a) when B is a pyridyl containing moiety, a quaternary nitrogen containing moiety, or a sulfur containing moiety, A is selected from the group consisting of hydrogen; halogen; $SR^1$; $R^2SR^1$; amino; hydroxy; and substituted or unsubstituted $C_1$–$C_8$ alkyl; or
(b) when B is other than a pyridyl containing moiety, a quaternary nitrogen containing moiety, or a sulfur containing moiety, A is selected from the group consisting of halogen; $SR^1$; $R^2SR^1$; amino; and hydroxy; and (3)
(a) $R^1$ is independently selected from the group consisting of hydrogen; —$C(O)R^7$; —$C(S)R^7$; —$C(O)N(R^7)_2$; —$C(O)OR^7$; —$C(S)N(R^7)_2$; and —$C(S)OR^7$; where $R^7$ is hydrogen or substituted or unsubstituted $C_1$–$C_8$ alkyl;
(b) $R^2$ is substituted or unsubstituted $C_1$–$C_8$ alkyl;
(c) $R^3$ is selected from the group consisting of nil and substituted or unsubstituted $C_1$–$C_8$ alkyl;
(d) $R^4$ is independently selected from the group consisting of hydrogen; substituted or unsubstituted $C_1$–$C_8$ alkyl; and —$R^2SR^1$; and
(e) $R^5$ is independently selected from the group consisting of substituted or unsubstituted $C_1$–$C_{15}$ alkyl; substituted or unsubstituted phenyl; benzyl; and —$R^2SR^1$;

or
(B) A and B are covalently linked together with C* to form a monocyclic or bicyclic ring having the following structure:

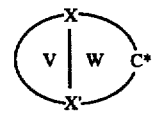

where
(1) W is a substituted or unsubstituted, saturated or unsaturated carbocyclic ring comprising C*, X, and X', said carbocyclic ring having a total of from 3 to 6 ring carbon atoms; or a substituted or unsubstituted, saturated or unsaturated heterocyclic ring comprising C*, X, and X', said heterocyclic ring having a total of from 4 to 6 ring atoms, where one or more of said ring atoms is N, O, or S;

(2) V is nil; a substituted or unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and (3) X and X' are independently N or C; except that if V is other than a nitrogen containing heterocycle, then at least one of V or W is substituted with one or more substituents selected from the group consisting of —$R^3N(R^4)_2$; $R^3[—N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$.

33. Phosphonocarboxylates and the pharmaceutically-acceptable salts thereof, having a general structure according to formula (I):

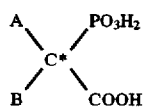

wherein
(A)
(1) A is hydroxy; and
(2) B is

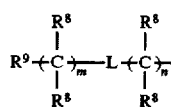

wherein
(a) m is an integer from 0 to 10; n is an integer from 0 to 10; and m+n is an integer from 0 to 10;
(b) $R^8$ is independently selected from the group consisting of nil; —$R^3SR^1$; hydrogen; substituted or unsubstituted $C_1$-$C_8$ alkyl; —$R^3OR^4$; —$R^3CO_2R^4$; —$R^3O_2CR^4$; —$R^3N(R^4)$; —$R^3[N(R^5)_3]^+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; nitro; hydroxy; substituted or unsubstituted saturated monocyclic or polycyclic carbocyclic rings; substituted or unsubstituted unsaturated monocyclic or polycyclic carbocyclic rings; substituted or unsubstituted saturated monocyclic or polycyclic heterocyclic rings; and substituted or unsubstituted unsaturated monocyclic or polycyclic heterocyclic rings;
(c) $R^1$ is independently selected from the group consisting of hydrogen; —C(O)$R^7$; —C(S)$R^7$; —C(O)N($R^7$)$_2$; —C(O)O$R^7$; —C(S)N($R^7$)$_2$; and —C(S)O$R^7$; where $R^7$ is hydrogen or substituted or unsubstituted $C_1$-$C_8$ alkyl;
(d) $R^3$ is selected from the group consisting of nil and substituted or unsubstituted $C_1$-$C_8$ alkyl;
(e) $R^4$ is independently selected from the group consisting of hydrogen; substituted or unsubstituted $C_1$-$C_8$ alkyl; and —$R^2SR^1$;
(f) $R^5$ is independently selected from the group consisting of substituted or unsubstituted $C_1$-$C_{15}$ alkyl; substituted or unsubstituted phenyl; benzyl; and —$R^2SR^1$;
(g) L is selected from the group consisting of nil; —N($R^8$)—; [—N($R^5$)$_2$—]$^+$; —S—; —O—; and —D—C(=E)—S—, where D is selected from the group consisting of covalent bond, O, or S, and E is O or S; and wherein
   (i) when L is —N($R^8$)—, or when L is [—N($R^5$)$_2$—]$^+$ and m is an integer from 1 to 10, $R^9$ is independently selected from the group consisting of nil; hydrogen; substituted or unsubstituted $C_1$-$C_{15}$ alkyl; $R^2SR^1$; and $R^{10}$;
   (ii) when L is [—N($R^5$)$_2$—]$^+$ and m=0, $R^9$ is selected from the group consisting of substituted or unsubstituted $C_1$-$C_{35}$ alkyl; $R^2SR^1$; and $R^{10}$; or
   (iii) when L is nil, —S—, —O—, or —D—C(=E)—S, $R^9$ is $R^{10}$;

(h) $R^{10}$ is a saturated, unsaturated, or aromatic monocyclic or polycylic carbocycle, or a saturated, unsaturated, or aromatic monocyclic or polycylic heterocycle comprising T and containing one or more heteroatoms; where said carbocycle or heterocycle is substituted with one or more $R^{11}$ substituents; and (i) each $R^{11}$ is independently selected from the group consisting of —$R^3SR^1$; hydrogen; substituted or unsubstituted $C_1$-$C_8$ alkyl; —$R^3OR^4$; —$R^3CO_2R^4$; —$R^3O_2CR^4$; —$R^3N(R^4)_2$; $R^3[—N(R^5)_3]^+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; hydroxy; substituted or unsubstituted arylalkyl; nitro; and unsubstituted or substituted aryl;

or
(B) A and B are covalently linked together with C* to form a monocyclic or bicyclic ring having the following structure:

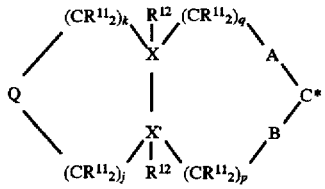

wherein
(a) A and B are independently selected from the group consisting of nil, —O—, —S—, and —$NR^{12}$—;
(b) Q is selected from the group consisting of nil; —$NR^{12}$—; and [—N($R^{13}$)$_2$—]$^+$;
(c) X and X' are independently selected from C or N;
(d) $R^{12}$ is independently selected from the group consisting of nil; —$R^3SR^1$; hydrogen; substituted or unsubstituted $C_1$-$C_8$ alkyl; —$R^3OR^4$; —$R^3CO_2R^4$; —$R^3O_2CR^4$; —$R^3N(R^4)_2$; $R^3[—N(R^5)_3]^+$; —$R^3N(R^4)C(O)R^4$; —$R^3C(O)N(R^4)_2$; halogen; —$R^3C(O)R^4$; hydroxy; substituted or unsubstituted arylalkyl; nitro; and unsubstituted or substituted aryl;
(e) $R^{13}$ is selected from the group consisting of nil; substituted or unsubstituted $C_1$-$C_{15}$ alkyl; substituted or unsubstituted phenyl; benzyl; and —$R^2SR^1$;
(f) when Q is other than nil, k and j and k+j are integers from 0 to 5; when Q is nil, k and j and k+j are integers from 0 to 6; and
(g) p and q and p+q are independently integers from 0 to 3; except that if Q is nil, then at least one of $R^{11}$ or $R^{12}$ is selected from the group consisting of —$R^3N(R^4)_2$; —$R^3[—N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$.

34. A pharmaceutical composition comprising pharmaceutically-acceptable carriers and a safe and effective amount of a phosphonocarboxylate, or a pharmaceutically-acceptable salt thereof, having a structure according to formula (I):

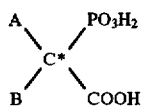

wherein (A)
(1) A is selected from the group consisting of hydrogen; halogen; $SR^1$, $R^2SR^1$; amino; hydroxy; and substituted or unsubstituted $C_1$-$C_8$ alkyl;

(2) B is
(a) $NH_2$;
(b) a saturated or unsaturated $C_1$-$C_{15}$ alkyl chain substituted with one or more substituents selected from the group consisting of —$R^3N(R^4)_2$; —$R^3[$—$N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$; and wherein said alkyl chain may also be substituted with one or more substituents selected from the group consisting of alkyl, alkenyl, alkoxy, hydroxy, oxo, thioxo, cyano, halo, thio, aryl, cycloalkyl, heteroalkyl, heterocycloalkyl, imino, hydroxyalkyl, aryloxy, arylalkyl, and alkynyl;
(c) a substituted or unsubstituted, saturated or unsaturated heteroalkyl chain having from 2 to 15 chain atoms, where one or more of said chain atoms is nitrogen; and where said heteroalkyl may be substituted with one or more substituents selected from the group consisting of —$R^3N(R^4)_2$, —$R^3[$—$N(R^5)_3]^+$, —$R^3N(R^4)C(O)R^4$, —$R^3N(R^4)C(S)R^4$, —$R^3N(R^4)C(N)R^4$, —$R^3C(O)N(R^4)_2$, alkyl, alkenyl, alkoxy, hydroxy, oxo, thioxo, amino, aminoalkyl, cyano, quaternary amino, quaternary aminoalkyl, amidino, amidinoalkyl, halo, thio, thiol, aryl, cycloalkyl, heteroalkyl, heterocycloalkyl, imino, hydroxyalkyl, aryloxy, arylalkyl, and alkynyl;
(d) a substituted or unsubstituted, saturated or unsaturated heteroalkyl chain having from 2 to 15 chain atoms, where one or more of said chain atoms is selected from S and O; and where said heteroalkyl chain is substituted with one or more substituents selected from the group consisting of —$R^3N(R^4)_2$; —$R^3[$—$N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$; or
(e) $R^6$—L— where
  (i) L is selected from the group consisting of nil; N; —$N(R^5)_2{}^+$; S; O; a substituted or unsubstituted, saturated or unsaturated $C_1$-$C_{15}$ alkyl chain, where said alkyl chain may be substituted with one or more substituents selected from the group consisting of alkyl, alkenyl, alkoxy, hydroxy, oxo, thioxo, ammo, aminoalkyl, cyano, quaternary amino, quaternary aminoalkyl, amidino, amidinoalkyl, halo, thio, thiol, aryl, cycloalkyl, heteroalkyl, heterocycloalkyl, imino, hydroxyalkyl, aryloxy, arylalkyl, and alkynyl; and a substituted or unsubstituted, saturated or unsaturated heteroalkyl chain having from 2 to 15 chain atoms, where one or more of said chain atoms is N, S, or O; and
  (ii) $R^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein $R^6$ may be substituted with one or more substituents independently selected from the group consisting of hydrogen; —$R^3SR^1$; substituted or unsubstituted $C_1$-$C_8$ alkyl; —$R^3OR^4$; —$R^3CO_2R^4$; —$R^3O_2CR^4$; —$R^3N(R^4)_2$; $R^3[$—$N(R^5)_3]^+$; —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; substituted or unsubstituted aryl; and hydroxy; and (3)
(a) $R^1$ is independently selected from the group consisting of hydrogen; —$C(O)R^7$; —$C(S)R^7$; —$C(O)N(R^7)_2$; —$C(O)OR^7$; —$C(S)N(R^7)_2$; and —$C(S)OR^7$; where $R^7$ is hydrogen or substituted or unsubstituted $C_1$-$C_8$ alkyl;
(b) $R^2$ is substituted or unsubstituted $C_1$-$C_8$ alkyl;
(c) $R^3$ is selected from the group consisting of nil and substituted or unsubstituted $C_1$-$C_8$ alkyl;
(d) $R^4$ is independently selected from the group consisting of hydrogen; substituted or unsubstituted $C_1$-$C_8$ alkyl; and —$R^2SR^1$; and
(e) $R^5$ is independently selected from the group consisting of substituted or unsubstituted $C_1$-$C_{15}$ alkyl; substituted or unsubstituted phenyl; benzyl; and —$R^2SR^1$;

or (B) A and B are covalently linked together with C* to form a monocyclic or bicyclic ring having the following structure:

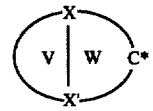

where
(1) W is a substituted or unsubstituted, saturated or unsaturated carbocyclic ring comprising C*, X, and X', said carbocyclic ring having a total of from 3 to 6 ring carbon atoms; or a substituted or unsubstituted, saturated or unsaturated heterocyclic ring comprising C*, X, and X', said heterocyclic ring having a total of from 4 to 6 ring atoms, where one or more of said ring atoms is N, O, or S;

(2) V is nil; a substituted or unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and (3) X and X' are independently N or C;
  except that if neither V nor W is a nitrogen containing heterocycle, then at least one of V or W is substituted with one or more substituents selected from the group consisting of —$R^3N(R^4)_2$; $R^3[$—$N(R)_3]^+$; —$R^3N(R^4)C(O)R^4$; —$R^3N(R^4)C(S)R^4$; —$R^3N(R^4)C(N)R^4$; and —$R^3C(O)N(R^4)_2$.

35. Phosphonocarboxylates and the pharmaceutically-acceptable salts thereof, having a structure according to formula (1):

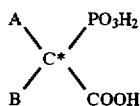

wherein
(A)
(1) B is
 (a) —NH$_2$;
 (b) a saturated or unsaturated C$_1$–C$_{15}$ alkyl chain substituted with one or more substituents selected from the group consisting of —R$^3$N(R$^4$)$_2$; R$^3$[—N(R)$_3$]$^+$; —R$^3$N(R$^4$)C(O)R$^4$; —R$^3$N(R$^4$)C(S)R$^4$; —R$^3$N(R$^4$)CN)R$^4$; and —R$^3$C(O)N(R$^4$)$_2$;
 (c) a substituted or unsubstituted, saturated or unsaturated heteroalkyl chain having from 2 to 15 chain atoms, where one or more of said chain atoms is nitrogen;
 (d) a substituted or unsubstituted, saturated or unsaturated heteroalkyl chain having from 2 to 15 chain atoms, where one or more of said chain atoms is selected from S and O; and where said heteroalkyl chain is substituted with one or more substituents selected from the group consisting of —R$^3$N(R$^4$)$_2$; —R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; and —R$^3$C(O)N(R$^4$)$_2$; or
 (e) R$^6$—L— where
  (i) L is selected from the group consisting of nil; N; —N(R$^5$)$_2$$^+$; S; O; a substituted or unsubstituted, saturated or unsaturated C$_1$–C$_{15}$ alkyl chain, where said alkyl chain may be substituted with one or more substituents selected from the group consisting of alkyl, alkenyl, alkoxy hydroxy, oxo, thioxo, amino, aminoalkyl, cyano, quaternary amino, quaternary aminoalkyl, amidino, amidinoalkyl, halo, thio, thiol, aryl, cycloalkyl, heteroalkyl, heterocycloalkyl, imino, hydroxyalkyl, aryloxy, arylalkyl, and alkynyl; and a substituted or unsubstituted, saturated or unsaturated heteroalkyl chain having from 2 to 15 chain atoms, where one or more of said chain atoms is N, S, or O; and
  (ii) R$^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein R$^6$ may be substituted with one or more substituents independently selected from the group consisting of hydrogen; —R$^3$SR$^1$; substituted or unsubstituted C$_1$–C$_8$ alkyl; —R$^3$OR$^4$; —R$^3$CO$_2$R$^4$; —R$^3$O$_2$CR$^4$; —R$^3$N(R$^4$)$_2$; R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; —R$^3$C(O)N(R$^4$)$_2$; halogen; —R$^3$C(O)R$^4$; arylalkyl; nitro; substituted or unsubstituted aryl; and hydroxy; and (2)
 (a) when B is a pyridyl containing moiety, a quaternary nitrogen containing moiety, or a sulfur containing moiety, A is selected from the group consisting of hydrogen; halogen; SR$^1$; R$^2$SR$^1$; amino; hydroxy; and substituted or unsubstituted C$_1$–C$_8$ alkyl; or
 (b) when B is other than a pyridyl containing moiety, a quaternary nitrogen containing moiety, or a sulfur containing moiety, A is selected from the group consisting of halogen; SR$^1$; R$^2$SR$^1$; amino; and hydroxy; and (3)
 (a) R$^1$ is independently selected from the group consisting of hydrogen; —C(O)R$^7$; —C(S)R$^7$; —C(O)N(R$^7$)$_2$; —C(O)OR$^7$; —C(S)N(R$^7$)$_2$; and —C(S)OR$^7$; where R$^7$ is hydrogen or substituted or unsubstituted C$_1$–C$_8$ alkyl;
 (b) R$^2$ is substituted or unsubstituted C$_1$–C$_8$ alkyl;
 (c) R$^3$ is selected from the group consisting of nil and substituted or unsubstituted C$_1$–C$_8$ alkyl;
 (d) R$^4$ is independently selected from the group consisting of hydrogen; substituted or unsubstituted C$_1$–C$_8$ alkyl; and —R$^2$SR$^1$; and
 (e) R$^5$ is independently selected from the group consisting of substituted or unsubstituted C$_1$–C$_{15}$ alkyl; substituted or unsubstituted phenyl; benzyl; and —R$^2$SR$^1$;

or
(B) A and B are covalently linked together with C* to form a monocyclic or bicyclic ring having the following structure:

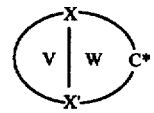

where
(1) W is a substituted or unsubstituted, saturated or unsaturated carbocyclic ring comprising C*, X, and X', said carbocyclic ring having a total of from 3 to 6 ring carbon atoms; or a substituted or unsubstituted, saturated or unsaturated heterocyclic ring comprising C*, X, and X', said heterocyclic ring having a total of from 4 to 6 ring atoms, where one or more of said ring atoms is N, O, or S;
(2) V is nil; a substituted or unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and
(3) X and X' are independently N or C; except that if V is other than a nitrogen containing heterocycle, then at least one of V or W is substituted with one or more substituents selected from the group consisting of —R$^3$N(R$^4$)$_2$; R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; and —R$^3$C(O)N(R$^4$)$_2$.

36. A pharmaceutical composition, according to claim 1, for the treatment of calcium-related metabolic disorders comprising pharmaceutically-acceptable carriers and an effective amount of an active wherein the active is a safe and effective calcium-regulating amount of phosphonocarboxylate, or a pharmaceutically-acceptable salt thereof, having a structure according to formula (I):

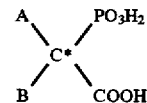

wherein
(A)
(1) A is selected from the group consisting of halogen; SR$^1$; R$^2$SR$^1$; amino; hydroxy; and substituted or unsubstituted C$_1$–C$_8$ alkyl;

(2) B is
(a) NH$_2$;
(b) a saturated or unsaturated C$_1$–C$_{15}$ alkyl chain substituted with one or more substituents selected from the group consisting of —R$^3$N(R$^4$)$_2$; —R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; and —R$^3$C(O)N(R$^4$)$_2$;
(c) a substituted or unsubstituted, saturated or unsaturated heteroalkyl chain having from 2 to 15 chain atoms, where one or more of said chain atoms is nitrogen;
(d) a substituted or unsubstituted, saturated or unsaturated heteroalkyl chain having from 2 to 15 chain atoms, where one or more of said chain atoms is selected from S and O; and where said heteroalkyl chain is substituted with one or more substituents selected from the group consisting of —R$^3$N(R$^4$)$_2$; —R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; and —R$^3$C(O)N(R$^4$)$_2$; or
(e) R$^6$—L— where
(i) L is selected from the group consisting of nil; N; —N(R$^5$)$_3$$^+$; S; O; a substituted or unsubstituted, saturated or unsaturated C$_1$–C$_{15}$ alkyl chain; and a substituted or unsubstituted, saturated or unsaturated heteroalkyl chain having from 2 to 15 chain atoms, where one or more of said chain atoms is N, S, or O; and
(ii) R$^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein R$^6$ may be substituted with one or more substituents independently selected from the group consisting of hydrogen; —R$^3$SR$^1$; substituted or unsubstituted C$_1$–C$_8$ alkyl; —R$^3$OR$^4$; —R$^3$CO$_2$R$^4$; —R$^3$O$_2$CR$^4$; —R$^3$N(R$^4$)$_2$; R$^3$[—N(R$^5$)$_3$]$^+$; R$^3$N(R$^4$)C(O)R$^4$; —R$^3$N(R$^4$)C(S)R$^4$; —R$^3$N(R$^4$)C(N)R$^4$; —R$^3$C(O)N(R$^4$)$_2$; halogen; —R$^3$C(O)R$^4$; arylalkyl; nitro; substituted or unsubstituted aryl; and hydroxy; and (3)
(a) R$^1$ is independently selected from the group consisting of hydrogen; —C(O)R$^7$; —C(S)R$^7$; —C(O)N(R$^7$)$_2$; —C(O)OR$^7$; —C(S)N(R$^7$)$_2$; and —C(S)OR$^7$; where R$^7$ is hydrogen or substituted or unsubstituted C$_1$–C$_8$ alkyl;
(b) R$^2$ is substituted or unsubstituted C$_1$–C$_8$ alkyl;
(c) R$^3$ is selected from the group consisting of nil and substituted or unsubstituted C$_1$–C$_8$ alkyl;
(d) R$^4$ is independently selected from the group consisting of hydrogen; substituted or unsubstituted C$_1$–C$_8$ alkyl; and —R$^2$SR$^1$; and
(e) R$^5$ is independently selected from the group consisting of substituted or unsubstituted C$_1$–C$_{15}$ alkyl; substituted or unsubstituted phenyl; benzyl; and —R$^2$SR$^1$;

or
(B) A and B are covalently linked together with C* to form a monocyclic or bicyclic ring having the following structure:

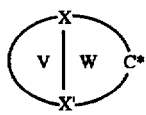

where
(1) W is a substituted or unsubstituted, saturated or unsaturated carbocyclic ring comprising C*, X, and X', said carbocyclic ring having a total of from 3 to 6 ring carbon atoms; or a substituted or unsubstituted, saturated or unsaturated heterocyclic ring comprising C*, X, and X', said heterocyclic ring having a total of from 4 to 6 ring atoms, where one or more of said ring atoms is N, O, or S;
(2) V is nil; a substituted or unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and
(3) X and X' are independently N or C;
except that if neither V nor W is a nitrogen containing heterocycle, then at least one of V or W is substituted with one or more substituents selected from the group consisting of —R$^3$N(R$^4$)$_2$; R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; and —R$^3$C(O)N(R$^4$)$_2$.

37. An oral pharmaceutical composition, according to claim 1, for the treatment of calcium-related disorders comprising pharmaceutically-acceptable carriers and an effective amount of an active wherein the active is a safe and effective calcium-regulating amount of a phosphonocarboxylate, or a pharmaceutically-acceptable salts thereof, having a structure according to formula (I):

$$\begin{array}{c} A \diagdown \diagup PO_3H_2 \\ C^* \\ \diagup \diagdown \\ B \qquad COOH \end{array}$$

wherein
(A)
(1) A is selected from the group consisting of halogen; SR$^1$; R$^2$SR$^1$; amino; hydroxy; and substituted or unsubstituted C$_1$–C$_8$ alkyl;
(2) B is
(a) NH$_2$;
(b) a saturated or unsaturated C$_1$–C$_{15}$ alkyl chain substituted with one or more substituents selected from the group consisting of —R$^3$N(R$^4$)$_2$; —R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; and —R$^3$C(O)N(R$^4$)$_2$;
(c) a substituted or unsubstituted, saturated or unsaturated heteroalkyl chain having from 2 to 15 chain atoms, where one or more of said chain atoms is nitrogen;
(d) a substituted or unsubstituted, saturated or unsaturated heteroalkyl chain having from 2 to 15 chain atoms, where one or more of said chain atoms is selected from S and O; and where said heteroalkyl chain is substituted with one or more substituents selected from the group consisting of —R$^3$N(R$^4$)$_2$; —R$^3$[—N(R$^5$)$_3$]$^+$; —R$^3$N(R$^4$)C(O)R$^4$; —R$^3$N(R$^4$)C(S)R$^4$; —R$^3$N(R$^4$)C(N)R$^4$; and —R$^3$C(O)N(R$^4$)$_2$; or
(e) R$^6$—L— where
(i) L is selected from the group consisting of nil; N; —N(R$^5$)$_3$$^+$; S; O; a substituted or unsubstituted, saturated or unsaturated C$_1$–C$_{15}$ alkyl chain; and a substituted or unsubstituted, saturated or unsaturated heteroalkyl chain having from 2 to 15 chain atoms, where one or more of said chain atoms is N, S, or O; and
(ii) R$^6$ is selected from the group consisting of saturated monocyclic or polycyclic carbocyclic rings; unsaturated monocyclic or polycyclic carbocyclic rings; saturated monocyclic or polycyclic heterocyclic rings; and unsaturated monocyclic or polycyclic heterocyclic rings; wherein $R^6$ may be substituted with one or more substituents independently selected from the group consisting of hydrogen; —$R^3SR^1$; substituted or unsubstituted $C_1$–$C_8$ alkyl; —$R^3OR^4$; —$R^3CO_2R^4$; —$R^3O_2CR^4$; —$R^3N(R^4)_2$; $R^3[$—$N(R^5)_3]^+$, —$R^3N(R^4)C(O)R^4$; —$R^3N(R^4)C(S)R^4$; —$R^3N(R^4)C(N)R^4$; —$R^3C(O)N(R^4)_2$; halogen; —$R^3C(O)R^4$; arylalkyl; nitro; substituted or unsubstituted aryl; and hydroxy; and (3)

(a) $R^1$ is independently selected from the group consisting of hydrogen; —$C(O)R^7$; —$C(S)R^7$; —$C(O)N(R^7)_2$; —$C(O)OR^7$; —$C(S)N(R^7)_2$; and —$C(S)OR^7$; where $R^7$ is hydrogen or substituted or unsubstituted $C_1$–$C_8$ alkyl;

(b) $R^2$ is substituted or unsubstituted $C_1$–$C_8$ alkyl;

(c) $R^3$ is selected from the group consisting of nil and substituted or unsubstituted $C_1$–$C_8$ alkyl;

(d) $R^4$ is independently selected from the group consisting of hydrogen; substituted or unsubstituted $C_1$–$C_8$ alkyl; and —$R^2SR^1$; and (e) $R^5$ is independently selected from the group consisting of substituted or unsubstituted $C_1$–$C_{15}$ alkyl; substituted or unsubstituted phenyl; benzyl; and —$R^2SR^1$;

or (B) A and B are covalently linked together with C* to form a monocyclic or bicyclic ring having the following structure:

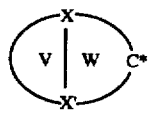

where (1) W is a substituted or unsubstituted, saturated or unsaturated carbocyclic ring comprising C*, X, and X', said carbocyclic ring having a total of from 3 to 6 ring carbon atoms; or a substituted or unsubstituted, saturated or unsaturated heterocyclic ring comprising C*, X, and X', said heterocyclic ring having a total of from 4 to 6 ring atoms, where one or more of said ring atoms is N, O, or S;

(2) V is nil; a substituted or unsubstituted, saturated or unsaturated carbocyclic ring comprising X and X', said carbocyclic ring having a total of from 3 to 8 ring carbon atoms; or a substituted or unsubstituted, saturated or unsaturated heterocyclic ring comprising X and X', said heterocyclic ring having a total of from 3 to 8 ring atoms, where one or more of said ring atoms is N, O, or S; and (3) X and X' are independently N or C;

except that if neither V nor W is a nitrogen containing heterocycle, then at least one of V or W is substituted with one or more substituents selected from the group consisting of —$R^3N(R^4)_2$; $R^3[$—$N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$.

38. A non-radioactive composition according to claim 36.

39. A compound according to claim 32 wherein A and B are covalently linked together with C* to form a compound of structure:

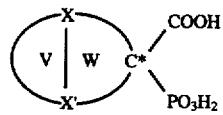

where (1) W is a substituted or unsubstituted, saturated or unsaturated carbocyclic ring comprising C*, X, and X', said carbocyclic ring having a total of from 5 to 6 ring carbon atoms; or a substituted or unsubstituted, saturated or unsaturated heterocyclic ring comprising C*, X, and X', said heterocyclic ring having a total of from 5 or 6 ring atoms, where one or more of said ring atoms is N, O, or S;

(2) V is nil; a substituted or unsubstituted, saturated or unsaturated carbocyclic ring comprising X and X', said carbocyclic ring having a total of from 5 to 7 ring carbon atoms; or a substituted or unsubstituted, saturated or unsaturated heterocyclic ring comprising X and X', said heterocyclic ring having a total of from 5 to 7 ring atoms, where one or more of said ring atoms is N.

40. The compound of claim 39 wherein V is a six membered ring, and W is a five membered ring.

41. A compound according to claim 32, having a structure according to formula (I):

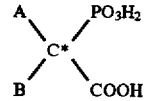

wherein (A)

(1) A is hydroxy;

(2) B is (a) $NH_2$;

(b) a substituted or unsubstituted, saturated or unsaturated heteroalkyl chain having from 2 to 15 chain atoms, where one or more of said chain atoms is nitrogen;

(d) a substituted or unsubstituted, saturated or unsaturated heteroalkyl chain having from 2 to 9 chain atoms, where one or more of said chain atoms is selected from S and O; and where said heteroalkyl chain is substituted with one or more substituents selected from the group consisting of —$R^3N(R^4)_2$; —$R^3[$—$N(R^5)_3]^+$; —$R^3N(R^4)C(O)R^4$; —$R^3N(R^4)C(S)R^4$; —$R^3N(R^4)C(N)R^4$; and —$R^3C(O)N(R^4)_2$; or (e) $R^6$—L—.

42. The compound of claim 33 of formula:

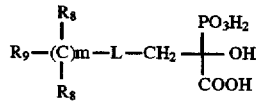

or a pharmaceutically acceptable salt thereof.

* * * * *